United States Patent
Weisbart et al.

(10) Patent No.: US 12,195,550 B2
(45) Date of Patent: *Jan. 14, 2025

(54) TARGETING INTRACELLULAR TARGET-BINDING DETERMINANTS WITH INTRACELLULAR ANTIBODIES

(71) Applicant: The United States of America as Represented by the Department of Veterans Affairs, Washington, DC (US)

(72) Inventors: Richard H. Weisbart, Sepulveda, CA (US); Robert N. Nishimura, Sepulveda, CA (US)

(73) Assignee: The United States of America as Represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/902,173

(22) Filed: Jun. 15, 2020

(65) Prior Publication Data

US 2022/0089771 A1   Mar. 24, 2022
US 2024/0052056 A9   Feb. 15, 2024

Related U.S. Application Data

(60) Continuation of application No. 15/042,106, filed on Feb. 11, 2016, now Pat. No. 10,683,363, which is a division of application No. 13/844,318, filed on Mar. 15, 2013, now Pat. No. 9,283,272.

(60) Provisional application No. 61/618,613, filed on Mar. 30, 2012.

(51) Int. Cl.
C07K 16/30 (2006.01)
A61K 39/00 (2006.01)
A61P 35/00 (2006.01)

(52) U.S. Cl.
CPC .......... *C07K 16/3053* (2013.01); *A61P 35/00* (2018.01); *A61K 2039/505* (2013.01); *C07K 2317/31* (2013.01); *C07K 2317/622* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,817,837 A | 6/1974 | Rubenstein et al. |
| 3,897,212 A | 7/1975 | Leon et al. |
| 4,134,792 A | 1/1979 | Boguslaski et al. |
| 4,174,384 A | 11/1979 | Ullman et al. |
| 4,220,722 A | 9/1980 | Rowley et al. |
| 4,275,149 A | 6/1981 | Litman et al. |
| 4,299,916 A | 11/1981 | Litman et al. |
| 4,623,627 A | 11/1986 | Huang et al. |
| 4,690,905 A | 9/1987 | Diamond et al. |
| 4,812,397 A | 3/1989 | Weisbart |
| 5,264,558 A | 11/1993 | Kim et al. |
| 5,959,084 A | 9/1999 | Ring |
| 6,485,977 B1 | 11/2002 | Colimer et al. |
| 7,189,396 B1 | 3/2007 | Weisbart |
| 7,700,544 B2 | 4/2010 | Kisilevsky et al. |
| 9,283,272 B2* | 3/2016 | Weisbart ................ C07K 16/42 |
| 9,701,740 B2 | 7/2017 | Hansen et al. |
| 10,683,363 B2* | 6/2020 | Weisbart ................ C07K 16/42 |
| 2005/0079184 A1 | 4/2005 | Chang |
| 2008/0292618 A1 | 11/2008 | Weisbart et al. |
| 2010/0143358 A1 | 6/2010 | Weisbart et al. |
| 2012/0070875 A1 | 3/2012 | Weisbart et al. |
| 2013/0266570 A1* | 10/2013 | Weisbart ................ C07K 16/42 435/375 |
| 2016/0237165 A1* | 8/2016 | Weisbart ................ C07K 16/42 |

FOREIGN PATENT DOCUMENTS

| | | |
|---|---|---|
| WO | WO 1997/32602 | 9/1997 |
| WO | WO 2010/138769 | 12/2010 |
| WO | WO 2012/135831 | 10/2012 |

OTHER PUBLICATIONS

Weisbart, R.H., et al. Construction and expression of a bispecific single-chain antibody that penetrates mutant p53 colon cancer cells and binds p53. international Journal of Oncology, 25:1113-1118,, 2004.

Weisbart, R.H. et al., A Cell-Penetrating Bispecific Antibody for Therapeutic Regulation of Intracellular Targets, Molecular Cancer Therapeutics, American Association for Cancer Research, May 9, 2012, p. 1-5.

U.S. Appl. No. 61/618,613, filed Mar. 30, 2012, Richard H. Weisbart.

(Continued)

*Primary Examiner* — Laura B Goddard
*Assistant Examiner* — Sarah A Alsomairy
(74) *Attorney, Agent, or Firm* — Ballard Spahr LLP

(57) ABSTRACT

The invention provides a method for inhibiting an intracellular target in a cell with a bispecific antibody comprising contacting the cell with a bispecific antibody having a first Fv fragment with a cell-penetrating determinant and a second Fv fragment with an intracellular target-binding determinant under suitable conditions so that the first Fv fragment causes the bispecific antibody to enter the cell and the second Fv fragment binds the intracellular target in the cell and thereby inhibiting the intracellular target.

2 Claims, 19 Drawing Sheets

Specification includes a Sequence Listing.

(56) References Cited

OTHER PUBLICATIONS

U.S. Appl. No. 15/042,106 (U.S. Pat. No. 10,683,363), filed Feb. 11, 2016 (Jun. 16, 2020), Richard H. Weisbart (US Department of Veterans Affairs).
U.S. Appl. No. 13/844,318 (U.S. Pat. No. 9,283,272), filed Mar. 15, 2013 (Oct. 10, 2013), Richard H. Weisbart.

* cited by examiner

Fig. 1A
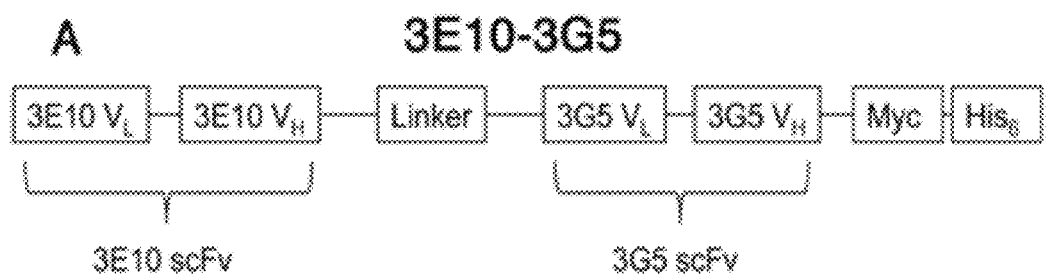
Fig. 1B
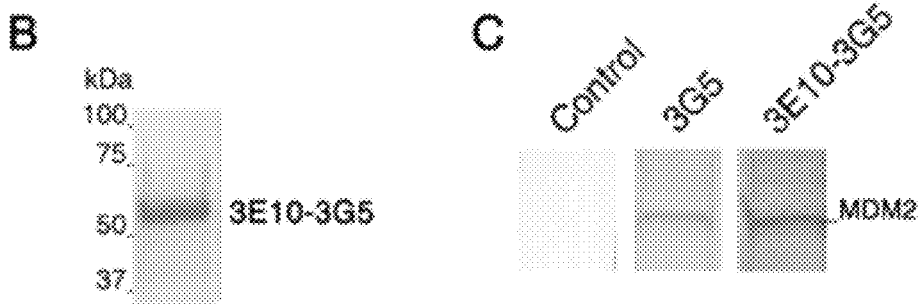
Fig. 1C
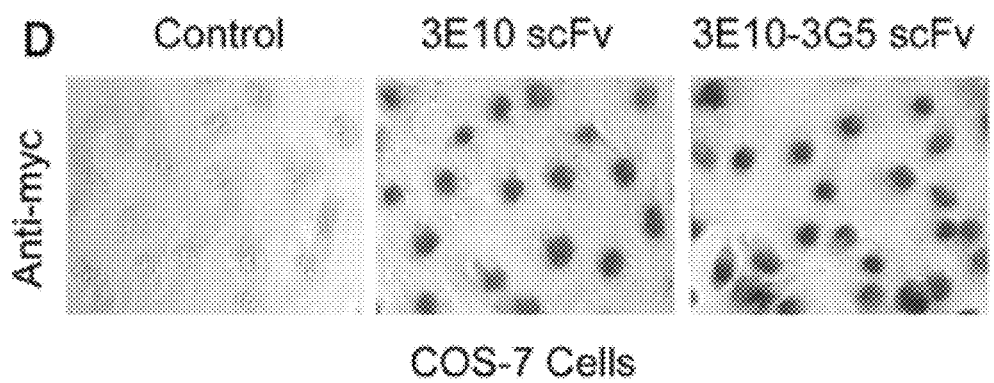
Fig. 1D

Fig. 2A
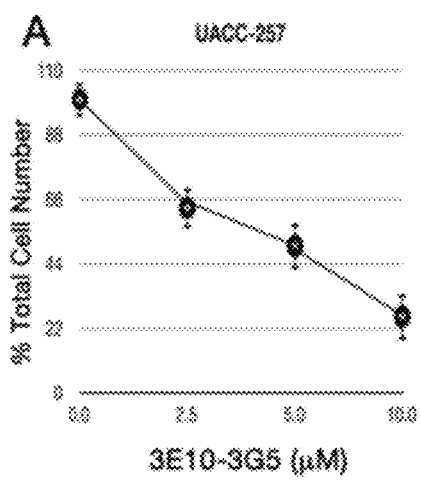
Fig. 2B
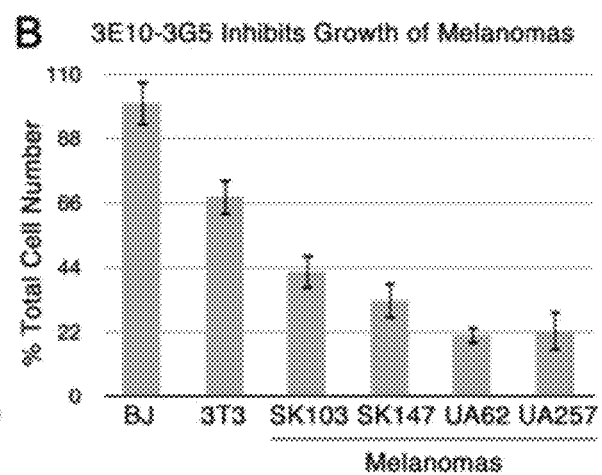
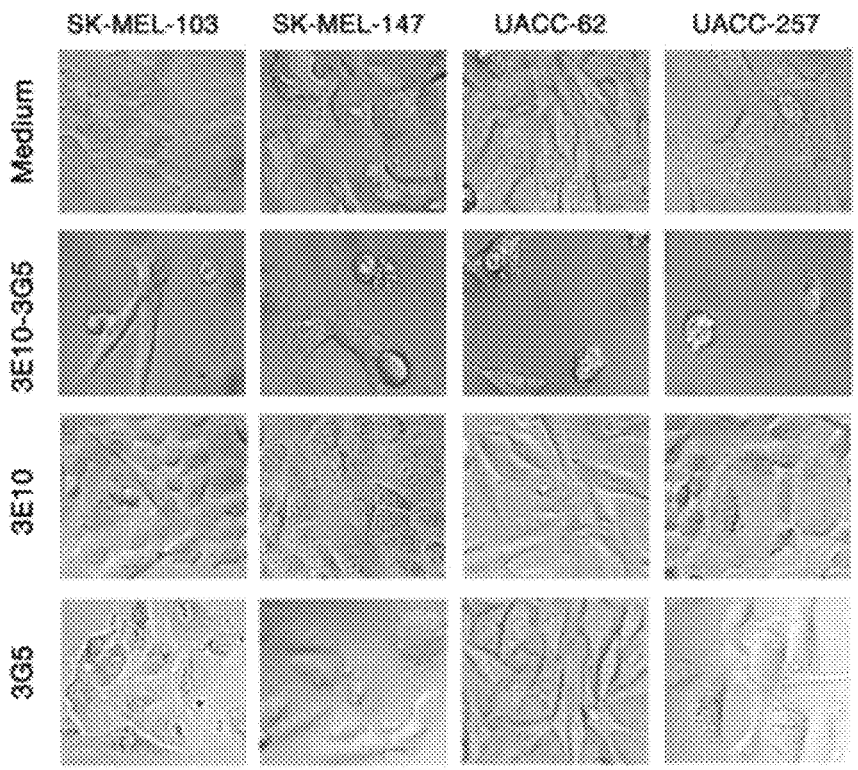
Fig. 2C

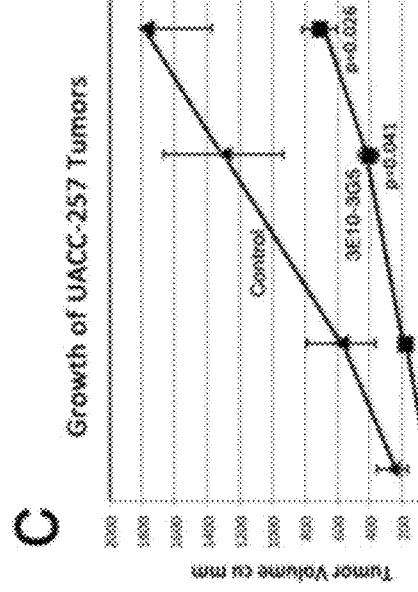
Fig. 3C
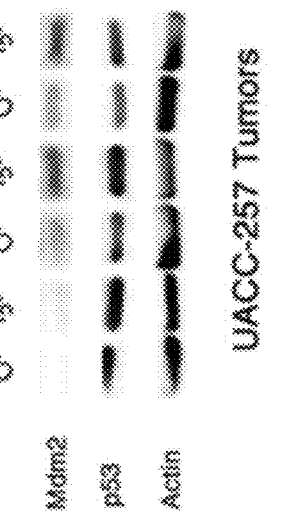
Fig. 3D
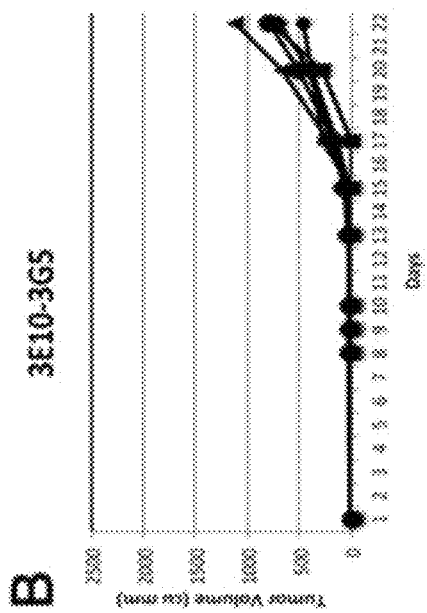
Fig. 3A
Fig. 3B

3E10-3G5 Bispecific scFv cloned between EcoRI and XbaI in pPicZαA pPicZαA α-factor signal sequence

```
ATG AGA TTT CCT TCA ATT TTT ACT GCT GTT TTA TTC GCA GCA TCC
 M   R   F   P   S   I   F   T   A   V   L   F   A   A   S

TCC GCA TTA GCT GCT CCA GTC AAC ACT ACA GAA GAT GAA ACG
 S   A   L   A   A   P   V   N   T   T   E   D   E   T

GCA CAA ATT CCG GCT GAA GCT GTC ATC GGT TAC TCA GAT TTA GAA
 A   Q   I   P   A   E   A   V   I   G   Y   S   D   L   E

GGG GAT TTC GAT GTT GCT GTT TTG CCA TTT TCC AAC AGC ACA AAT
 G   D   F   D   V   A   V   L   P   F   S   N   S   T   N

AAC GGG TTA TTG TTT ATA AAT ACT ACT ATT GCC AGC ATT GCT GCT
 N   G   L   L   F   I   N   T   T   I   A   S   I   A   A
```
                                    Kex2 signal cleavage → End signal seq →

```
AAA GAA GGG GTA TCT CTC GAG AAA AGA GAG GCT GAA GCT
 K   E   G   V   S   L   E   K   R   E   A   E   A
```
                                              ← Ste13 signal cleavage (AGIH Increases) Begin 3E10 →
solubility
```
GCA GGA ATT CAC GAC ATT GTC CTG ACA CAG TCT CCT GCT TCC TTA
 A   G   I   H   D   I   V   L   T   Q   S   P   A   S   L
```
    ───EcoRI───

Fig. 4

```
GCT GTA TCT CTG GGG CAG AGG GCC ACC ATC TCC TGC AGG GCC AGC
 A   V   S   L   G   Q   R   A   T   I   S   C   R   A   S

┌─────3E10 Vk CDR1─────
AAA AGT GTC AGT ACA TCT AGC TAT  AGT TAC ATG CAC  TGG TAC CAA
 K   S   V   S   T   S   S   Y   S   Y   M   H    W   Y   Q

──┐                                              ┌─3E10 Vk
CAG AAA CCA GGA CAG CCA CCC AAA CTC CTC ATC AAG  TAT GCA TCC
 Q   K   P   G   Q   P   P   K   L   L   I   K    Y   A   S

CDR2─┐
TAC CTA GAA TCT GGG GTT CCT GCC AGG TTC AGT GGC AGT GGG TCT
 Y   L   E   S   G   V   P   A   R   F   S   G   S   G   S

GGG ACA GAC TTC ACC CTC AAC ATC CAT CCT GTG GAG GAG GAT
 G   T   D   F   T   L   N   I   H   P   V   E   E   D

┌───────3E10 Vk CDR3───────┐
GCT GCA ACA TAT TAC TGT CAG CAC AGT AGG GAG TTT CCG TGG ACG
 A   A   T   Y   Y   C   Q   H   S   R   E   F   P   W   T

TTC GGT GGA GGC ACC AAG CTG GAA ATC AAA CGG GCT GAT GCT GCA
 F   G   G   G   T   K   L   E   I   K   R   A   D   A   A (GGGGS)₃ Linker
CCC GGG GGT GGC GGT TCT GGC GGT GGC GGA TCT GGA GGC GGT GGC
 P   G   G   G   G   S   G   G   G   G   S   G   G   G   G
```

Fig. 4, continued

```
TCT GAG GTG CAG CTG GTG GAG TCT GGG GGA GGC TTA GTG AAG CCT
 S   E   V   Q   L   V   E   S   G   G   G   L   V   K   P

GGA GGG TCC CGG AAA CTC TCC TGT GCA GCC TCT GGA TTC ACT TTC
 G   G   S   R   K   L   S   C   A   A   S   G   F   T   F

3E10 VH CDR1
AGT AAC TAT GGA ATG CAC TGG GTC CGT CAG GCT CCA GAG AAG GGG
 S   N   Y   G   M   H   W   V   R   Q   A   P   E   K   G
     N
(D31N mutation 3E10 VH enhances cell penetration)

3E10 VH CDR2
CTG GAG TGG GTT GCA TAC ATT AGT AGT GGC AGT AGT ACC ATC TAC
 L   E   W   V   A   Y   I   S   S   G   S   S   T   I   Y

TAT GCA GAC ACA GTG AAG GGC CGA TTC ACC ATC TCC AGA GAC AAT
 Y   A   D   T   V   K   G   R   F   T   I   S   R   D   N

GCC AAG AAC ACC CTG TTC CTG CAA ATG ACC AGT CTA AGG TCT GAG
 A   K   N   T   L   F   L   Q   M   T   S   L   R   S   E

3E10 VH CDR3
GAC ACA GCC ATG TAT TAC TGT GCA AGG CGG GGG TTA CTA CTT GAC
 D   T   A   M   Y   Y   C   A   R   R   G   L   L   L   D
```

Fig. 4, continued

```
                                                      End 3E10 →                    Swivel Sequence
TAC TGG GGC CAA GGC ACC ACT CTC ACA GTC TCC TCA GCT TCC ACC
 Y   W   G   Q   G   T   T   L   T   V   S   S   A   S   T Human CH1 Linker
AAG GGC CCA TCC GTC TTC CCC CTG GCG CCC CTG GAG TCT TCC GGA
 K   G   P   S   V   F   P   L   A   P   L   E   S   S   G → Begin 3G5
TCC GAC ATC CAG ATG ACT CAG TCT CCA GCC TCC CTA TCT GTA TCT
 S   D   I   Q   M   T   Q   S   P   A   S   L   S   V   S 3G5 Vk CDR1
GTG GGA GAA ACT GTC ACC ATC ACA TGT CGA GCA AGT GAG AAT ATT
 V   G   E   T   V   T   I   T   C   R   A   S   E   N   I 3G5 Vk CDR2
TAC AGT AAT TTA GCA TGG TAT CAG CAG AAA CAG GGA AAA TCT CCT
 Y   S   N   L   A   W   Y   Q   Q   K   Q   G   K   S   P CAG CTC CTG GTG TAT GGT GCA ACA AAC TTA GCA GAT GGT GTG CCA
 Q   L   L   V   Y   G   A   T   N   L   A   D   G   V   P TCA AGG TTC AGT GGC AGT GGG TCA GGC ACA CAG TAT TCC CTC AAG
 S   R   F   S   G   S   G   S   G   T   Q   Y   S   L   K ATC AAC AGC CTG CAG TCT GAA GAT TTT GGG AGT TAT TAC TGT CAA
 I   N   S   L   Q   S   E   D   F   G   S   Y   Y   C   Q
```

Fig. 4, continued

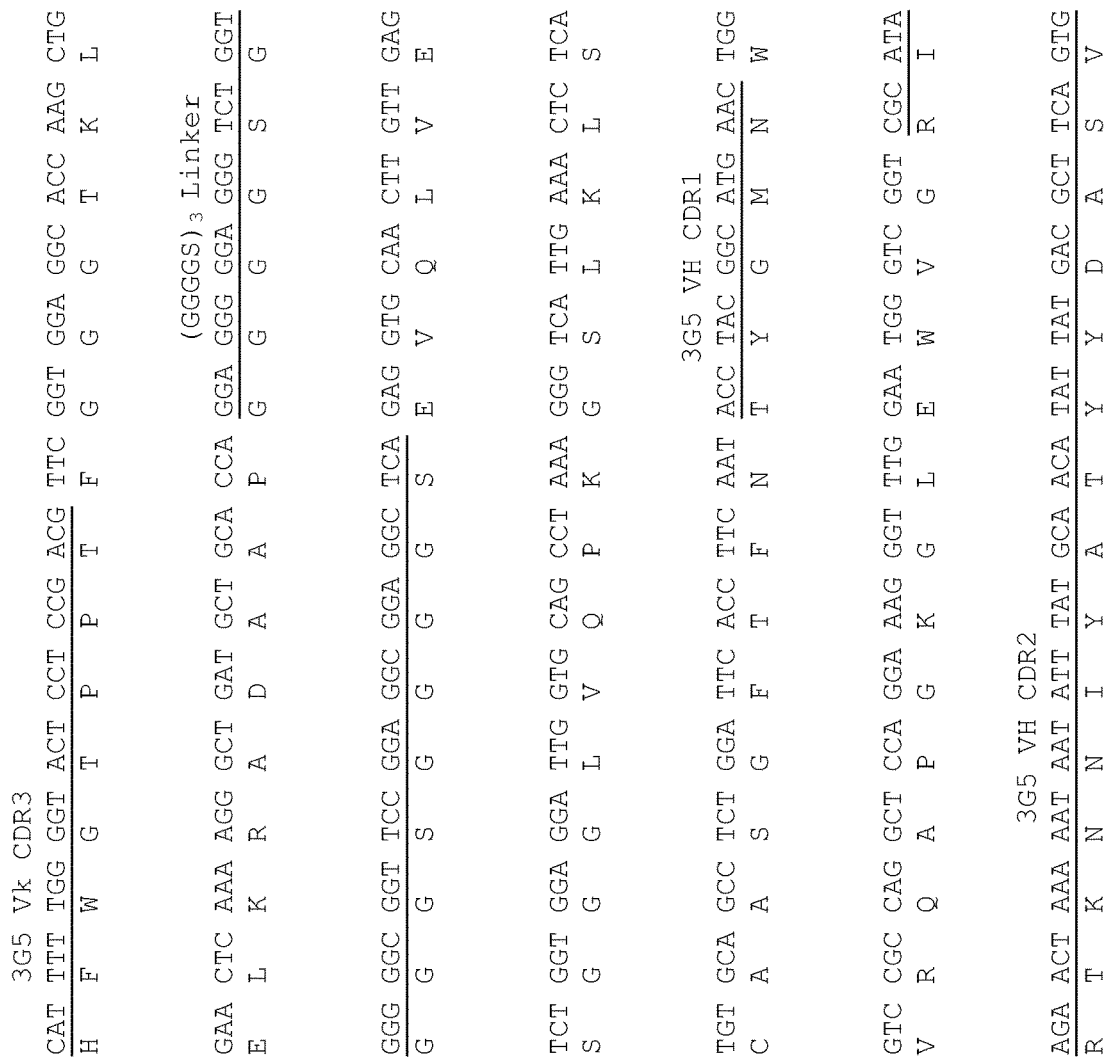
Fig. 4, continued

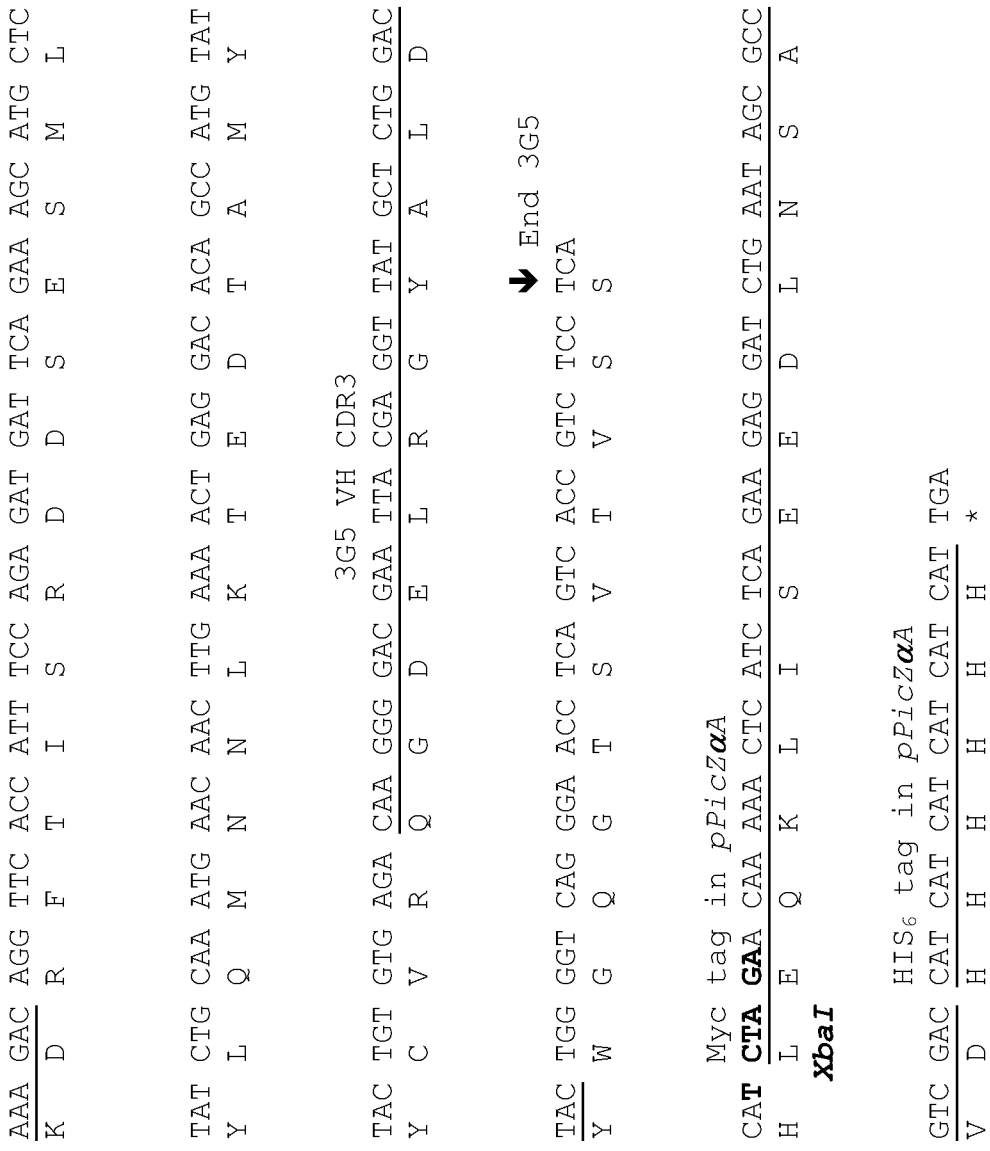
Fig. 4, continued

```
GCT GTA TCT CTG GGG CAG AGG GCC ACC ATC TCC TGC AGG GCC AGC
 A   V   S   L   G   Q   R   A   T   I   S   C   R   A   S

3E10 Vk CDR1
AAA AGT GTC AGT ACA TCT AGC TAT AGC ATG CAC TGG TAC CAA
 K   S   V   S   T   S   S   Y   S   M   H   W   Y   Q

3E10 Vk
CAG AAA CCA GGA CAG CCA CCC AAA CTC CTC ATC AAG TAT GCA TCC
 Q   K   P   G   Q   P   P   K   L   L   I   K   Y   A   S

CDR2
TAC CTA GAA TCT GGG GTT CCT GCC AGG TTC AGT GGC AGT GGG TCT
 Y   L   E   S   G   V   P   A   R   F   S   G   S   G   S

GGG ACA GAC TTC ACC CTC AAC ATC CAT CCT GTG GAG GAG GAG GAT
 G   T   D   F   T   L   N   I   H   P   V   E   E   E   D

3E10 Vk CDR3
GCT GCA ACA TAT TAC TGT CAG CAC AGT AGG GAG TTT CCG TGG ACG
 A   A   T   Y   Y   C   Q   H   S   R   E   F   P   W   T

TTC GGT GGA GGC ACC AAG CTG GAA ATC AAA CGG GCT GAT GCT GCA
 F   G   G   G   T   K   L   E   I   K   R   A   D   A   A (GGGGS)₃ Linker
CCC GGG GGT GGC GGT TCT GGC GGT GGC GGT TCT GGA GGC GGT GGC
 P   G   G   G   G   S   G   G   G   G   S   G   G   G   G
```

Fig. 5, continued

TCT GAG GTG CAG CTG GTG GAG TCT GGG GGA GGC TTA GTG AAG CCT
 S   E   V   Q   L   V   E   S   G   G   G   L   V   K   P

GGA GGG TCC CGG AAA CTC TCC TGT GCA GCC TCT GGA TTC ACT TTC
 G   G   S   R   K   L   S   C   A   A   S   G   F   T   F

<u>3E10 VH CDR1</u>
AGT AAC TAT GGA ATG CAC TGG GTC CGT CAG GCT CCA GAG AAG GGG
 S  <b>N</b>  Y   G   M   H   W   V   R   Q   A   P   E   K   G
(D31N mutation 3E10 VH enhances cell penetration)

<u>3E10 VH CDR2</u>
CTG GAG TGG GTT GCA TAC ATT AGT AGT GGC AGT AGT

```
                                    End 3E10 →
TAC TGG GGC CAA GGC ACC ACT CTC ACA GTC TCC TCA GCT TCC ACC
 Y   W   G   Q   G   T   T   L   T   V   S   S   A   S   T

Human CH1 Linker                   Swivel Sequence
AAG GGC CCA TCC GTC TTC CCC CTG GCG CCC CTG GAG TCT TCC GGA
 K   G   P   S   V   F   P   L   A   P   L   E   S   S   G → Begin PAb421
TCC GAT GTT GTG ATG ACC CAG ACT CCA CTC ACT TTG TCG GTT ACC
 S   D   V   V   M   T   Q   T   P   L   T   L   S   V   T PAb421 Vk CDR1
ATT GGA CAA CCA GCC TCC ATC TCT TGC AAG TCA AGT CAG AGC CTC
 I   G   Q   P   A   S   I   S   C   K   S   S   Q   S   L TTG GAT AGT GAT GGA AAG ACA TAC TTG AAT TGG TTG TTA CAG AGG
 L   D   S   D   G   K   T   Y   L   N   W   L   L   Q   R PAb421 Vk CDR2
CCA GGC CAG TCT CCA AAG CGC CTA ATC TAT CTG GTG TCT AAA CTG
 P   G   Q   S   P   K   R   L   I   Y   L   V   S   K   L GAC TCT GGA GTC CCT GAC AGG TTC ACT GGC AGT GGA TCA GGG ACA
 D   S   G   V   P   D   R   F   T   G   S   G   S   G   T GAT TTC ACA CTG AAA ATC AAC AGA GTG GAG GCT GAG GAT TTG GGA
 D   F   T   L   K   I   N   R   V   E   A   E   D   L   G
```

Fig. 5, continued

```
                    PAb421 Vk CDR3
GTT TAT TAT TGC TGG CAA GGT ACA CAT TCT CCG CTC ACG TTC GGT
 V   Y   Y   C   W   Q   G   T   H   S   P   L   T   F   G

GCT GGC ACC AAG CTG GAA ATT AAA CGG GCT GAC GCT GCA CCC GGG
 A   G   T   K   L   E   I   K   R   A   D   A   A   P   G (GGGGS)₃ Linker
GGA GGG GGA TCT GGT GGC GGA TCA GGT GGA TCT CAG
 G   G   G   S   G   G   G   S   G   G   S   Q GTG CAG CTG CAG CAG TCT GGG GCA GAG CTT GTG AGG TCA GGG GCC
 V   Q   L   Q   Q   S   G   A   E   L   V   R   S   G   A TCA GTC AAG TTG TCC TGC ACA GCT TCT GGC TTC AAC ATT AAA GAC
 S   V   K   L   S   C   T   A   S   G   F   N   I   K   D PAb421 VH CDR1
TAC TAT ATG CAC TGG GTG AAG CAG AGG CCT GAA CAG GGC CTG GAG
 Y   Y   M   H   W   V   K   Q   R   P   E   Q   G   L   E PAb421 VH CDR2
TGG ATT GGA TGG ATT GAT CCT GAG AAT GGT GAT ACT GAA TAT GCC
 W   I   G   W   I   D   P   E   N   G   D   T   E   Y   A CCG AAG TTC CAG GGC AAG GCC ACT ATG ACT GCA GAC ACA TCC TCC
 P   K   F   Q   G   K   A   T   M   T   A   D   T   S   S
```

Fig. 5, continued

```
GAT ACA GCC TAC CTG CAG CTC AGC AGC CTG GCA TCT GAG GAC ACT
 D   T   A   Y   L   Q   L   S   S   L   A   S   E   D   T

PAb421 VH CDR3
GCC GTC TAT TAT TGT AAT TTT TAC GGG GAT GCT TTG GAC TAC TGG
 A   V   Y   Y   C   N   F   Y   G   D   A   L   D   Y   W

End PAb421 →         XbaI
GGT CAA GGA ACC TCG GTC ACC GTC TCC TCT CAT CTA GAA CAA AAA
 G   Q   G   T   S   V   T   V   S   S   H   L   E   Q   K

Myc tag in pPicZαA                    HIS₆ tag in
CTC ATC TCA GAA GAG GAT CTG AAT AGC GCC GTC GAC CAT CAT CAT
 L   I   S   E   E   D   L   N   S   A   V   D   H   H   H pPicZαA
CAT CAT CAT TGA
 H   H   H   *
```

Fig. 5, continued

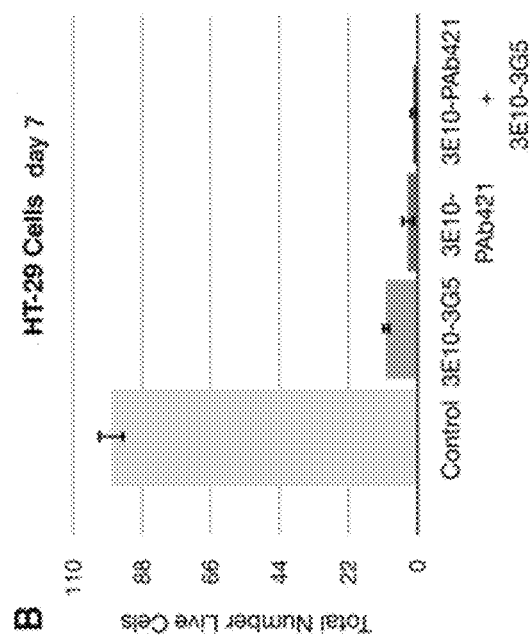
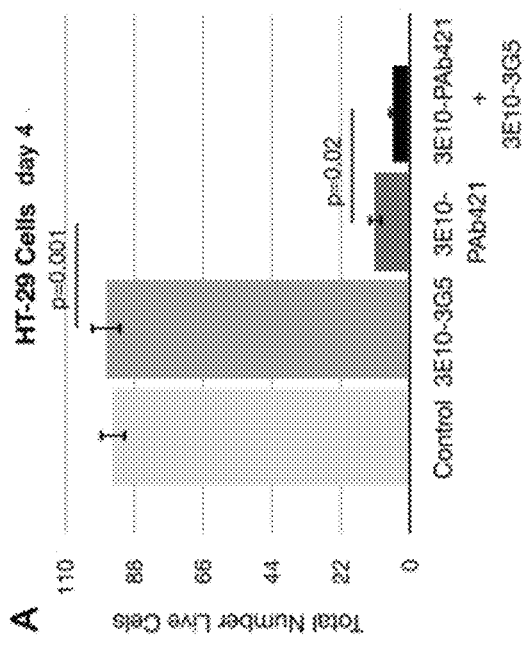
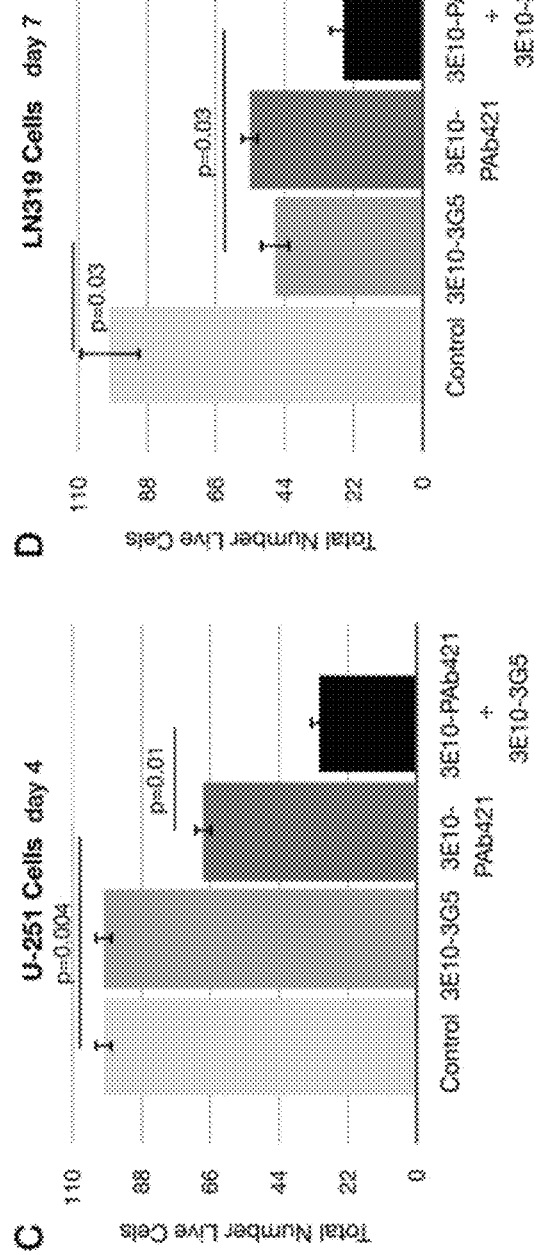
Fig. 7A
Fig. 7B
Fig. 7C
Fig. 7D

SEQUENCE LISTING

```
<160> NUMBER OF SEQ ID NOS: 42

<210> SEQ ID NO 1
<211> LENGTH: 1905
<212> TYPE: DNA
<213> ORGANISM: Artificial Sequence
<220> FEATURE:
<223> OTHER INFORMATION: Coding sequences for full length unprocessed
      bispecific scFv 3E10-3G5 chimeric antibody derived from Mus
      musculus, Homo sapiens, Saccharomyces cerevisiae, and synthetic
      sequence from no known organism
<220> FEATURE:
<221> NAME/KEY: CDS
<222> LOCATION: (1)..(1905)
<223> OTHER INFORMATION: Coding sequences for full length unprocessed
      bispecific scFv 3E10-3G5 chimeric antibody with secretory signal,
      protease cleavage sites, solubility enhancing peptide, and epitope
      tags produced using pPicZalpha A expression vector in Pichia
      pastoris
<220> FEATURE:
<221> NAME/KEY: misc_feature
```

```
<222> LOCATION: (1)..(3)
<223> OTHER INFORMATION: ATG, start site of translation provided by
      pPicZalpha A expression vector
<220> FEATURE:
<221> NAME/KEY: misc_feature
<222> LOCATION: (1)..(267)
<223> OTHER INFORMATION: Coding sequence for Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing alpha-factor
      secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing alpha-factor
      secretory signal
<220> FEATURE:
<221> NAME/KEY: misc_feature
<222> LOCATION: (265)..(270)
<223> OTHER INFORMATION: Ste13 signal cleavage site between Ala-Ala
      encoded by nucleotide positions 265-270 for removing alpha-factor
      secretory signal
<220> FEATURE:
<221> NAME/KEY: misc_feature
<222> LOCATION: (268)..(279)
<223> OTHER INFORMATION: Ala-Gly-Ile-His peptide coding sequence for
      increasing solubility of scFv bispecific antibody
<220> FEATURE:
<221> NAME/KEY: misc_feature
<222> LOCATION: (272)..(277)
<223> OTHER INFORMATION: EcoRI restriction enzyme site, recreated after
      insertion of 3E10-3G5 scFVc EcoRI-XbaI cDNA fragment into
      EcoRI-XbaI sites of pPicZalpha A expression vector
<220> FEATURE:
<221> NAME/KEY: misc_feature
<222> LOCATION: (280)..(1833)
<223> OTHER INFORMATION: 3E10-3G5 bispecific scFv antibody coding
      sequence with enhanced cell penetration mutation
<220> FEATURE:
<221> NAME/KEY: misc_feature
<222> LOCATION: (280)..(1023)
<223> OTHER INFORMATION: 3E10 Fv fragment coding sequence with enhanced
      cell penetration mutation
<220> FEATURE:
<221> NAME/KEY: misc_feature
<222> LOCATION: (280)..(630)
<223> OTHER INFORMATION: anti-DNA monoclonal antibody 3E10 kappa light
      (Vk) chain coding sequence from Mus musculus
<220> FEATURE:
<221> NAME/KEY: misc_feature
<222> LOCATION: (382)..(393)
<223> OTHER INFORMATION: 3E10 kappa light (Vk) chain complementarity
      determining region 1 (CDR1) coding sequence from Mus musculus
<220> FEATURE:
<221> NAME/KEY: misc_feature
<222> LOCATION: (442)..(459)
<223> OTHER INFORMATION: 3E10 kappa light (Vk) chain CDR2 coding
      sequence  from Mus musculus
<220> FEATURE:
<221> NAME/KEY: misc_feature
<222> LOCATION: (556)..(582)
<223> OTHER INFORMATION: 3E10 kappa light (Vk) chain CDR3 coding
      sequence  from Mus musculus
<220> FEATURE:
<221> NAME/KEY: misc_feature
<222> LOCATION: (631)..(675)
<223> OTHER INFORMATION: (GGGGS)3 peptide linker coding sequence
<220> FEATURE:
<221> NAME/KEY: misc_feature
<222> LOCATION: (676)..(1023)
<223> OTHER INFORMATION: anti-DNA monoclonal antibody 3E10 variable
      heavy (VH) chain coding sequence from Mus musculus with enhanced
      cell penetration mutation (D31N mutation at CDR1 of VH chain)
<220> FEATURE:
```

```
<221> NAME/KEY: misc_feature
<222> LOCATION: (766)..(780)
<223> OTHER INFORMATION: 3E10 variable heavy (VH) chain CDR1 coding
      sequence  from Mus musculus with D31N mutation for enhanced cell
      penetration
<220> FEATURE:
<221> NAME/KEY: misc_feature
<222> LOCATION: (766)..(768)
<223> OTHER INFORMATION: Asn amino acid coding sequence; D31N mutation
      in first amino acid of CDR1 of 3E10 variable heavy (VH) chain for
      enhanced cell penetration
<220> FEATURE:
<221> NAME/KEY: misc_feature
<222> LOCATION: (823)..(873)
<223> OTHER INFORMATION: 3E10 variable heavy (VH) chain CDR2 coding
      sequence  from Mus musculus
<220> FEATURE:
<221> NAME/KEY: misc_feature
<222> LOCATION: (970)..(990)
<223> OTHER INFORMATION: 3E10 variable heavy (VH) chain CDR3 coding
      sequence  from Mus musculus
<220> FEATURE:
<221> NAME/KEY: misc_feature
<222> LOCATION: (1024)..(1062)
<223> OTHER INFORMATION: Human constant heavy chain 1 (CH1) linker
      coding sequence
<220> FEATURE:
<221> NAME/KEY: misc_feature
<222> LOCATION: (1063)..(1080)
<223> OTHER INFORMATION: Swivel coding sequence
<220> FEATURE:
<221> NAME/KEY: misc_feature
<222> LOCATION: (1081)..(1833)
<223> OTHER INFORMATION: 3G5 Fv fragment coding sequence
<220> FEATURE:
<221> NAME/KEY: misc_feature
<222> LOCATION: (1081)..(1419)
<223> OTHER INFORMATION: anti-MDM2 monoclonal antibody 3G5 kappa light
      (Vk) chain coding sequence from Mus musculus
<220> FEATURE:
<221> NAME/KEY: misc_feature
<222> LOCATION: (1150)..(1182)
<223> OTHER INFORMATION: 3G5 kappa light (Vk) chain complementarity
      determining region 1 (CDR1) coding sequence from Mus musculus
<220> FEATURE:
<221> NAME/KEY: misc_feature
<222> LOCATION: (1228)..(1248)
<223> OTHER INFORMATION: 3G5 kappa light (Vk) chain CDR2 coding sequence
      from Mus musculus
<220> FEATURE:
<221> NAME/KEY: misc_feature
<222> LOCATION: (1345)..(1371)
<223> OTHER INFORMATION: 3G5 kappa light (Vk) chain CDR3 coding sequence
      from Mus musculus
<220> FEATURE:
<221> NAME/KEY: misc_feature
<222> LOCATION: (1420)..(1464)
<223> OTHER INFORMATION: (GGGGS)3 peptide linker coding sequence
<220> FEATURE:
<221> NAME/KEY: misc_feature
<222> LOCATION: (1465)..(1833)
<223> OTHER INFORMATION: anti-MDM2 monoclonal antibody 3G5 variable
      heavy (VH) chain coding sequence from Mus musculus
<220> FEATURE:
<221> NAME/KEY: misc_feature
<222> LOCATION: (1555)..(1569)
<223> OTHER INFORMATION: 3G5 variable heavy (VH) chain CDR1 coding
      sequence from Mus musculus
<220> FEATURE:
<221> NAME/KEY: misc_feature
<222> LOCATION: (1612)..(1668)
<223> OTHER INFORMATION: 3G5 variable heavy (VH) chain CDR2 coding
      sequence from Mus musculus
<220> FEATURE:
<221> NAME/KEY: misc_feature
<222> LOCATION: (1765)..(1800)
<223> OTHER INFORMATION: 3G5 variable heavy (VH) chain CDR3 coding
      sequence from Mus musculus
<220> FEATURE:
```

```
<221> NAME/KEY: misc_feature
<222> LOCATION: (1836)..(1841)
<223> OTHER INFORMATION: XbaI restriction enzyme site, recreated after
      insertion of 3E10-3G5 scFVc EcoRI-XbaI cDNA fragment into EcoRI-
      XbaI sites of pPicZalpha A expression vector
<220> FEATURE:
<221> NAME/KEY: misc_feature
<222> LOCATION: (1840)..(1869)
<223> OTHER INFORMATION: Myc epitope tag, EQKLISEEDL, coding sequence
      provided by pPicZalpha A expression vector
<220> FEATURE:
<221> NAME/KEY: misc_feature
<222> LOCATION: (1885)..(1902)
<223> OTHER INFORMATION: (His)6 epitope tag coding sequence, provided by
      pPicZalpha A expression vector
<220> FEATURE:
<221> NAME/KEY: misc_feature
<222> LOCATION: (1903)..(1905)
<223> OTHER INFORMATION: TGA, stop codon provided by pPicZ A expression
      vector
<300> PUBLICATION INFORMATION:
<301> AUTHORS: Weisbart RH, Gera JF, Chan G, Hansen JE, Li E, Cloninger
      C, Levine AJ, and Nishimura RN
<302> TITLE: A cell-penetrating bispecific antibody for therapeutic
      regulation of intracellular targets
<303> JOURNAL: Mol Cancer Ther.
<304> VOLUME: 11
<305> ISSUE: 10
<306> PAGES: 2169-73
<307> DATE: 2012-08-03
<313> RELEVANT RESIDUES IN SEQ ID NO: (1)..(1905)

<400> SEQUENCE: 1 atg aga ttt cct tca att ttt act gct gtt tta ttc gca gca tcc tcc        48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc       144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg       192
Asp Val Ala Val Leu Pro Phe Ser Asn Ser Thr Asn Asn Gly Leu Leu
50                  55                  60 ttt ata aat act act att gcc agc att gct gct aaa gaa gaa ggg gta       240
Phe Ile Asn Thr Thr Ile Ala Ser Ile Ala Ala Lys Glu Glu Gly Val
65                  70                  75                  80 tct ctc gag aaa aga gag gct gaa gct gca gga att cac gac att gtc       288
Ser Leu Glu Lys Arg Glu Ala Glu Ala Ala Gly Ile His Asp Ile Val
                85                  90                  95 ctg aca cag tct cct gct tcc tta gct gta tct ctg ggg cag agg gcc       336
Leu Thr Gln Ser Pro Ala Ser Leu Ala Val Ser Leu Gly Gln Arg Ala
            100                 105                 110 acc atc tcc tgc agg gcc agc aaa agt gtc agt aca tct agc tat agt       384
Thr Ile Ser Cys Arg Ala Ser Lys Ser Val Ser Thr Ser Ser Tyr Ser
        115                 120                 125 tac atg cac tgg tac caa cag aaa cca gga cag cca ccc aaa ctc ctc       432
Tyr Met His Trp Tyr Gln Gln Lys Pro Gly Gln Pro Pro Lys Leu Leu
    130                 135                 140 atc aag tat gca tcc tac cta gaa tct ggg gtt cct gcc agg ttc agt       480
Ile Lys Tyr Ala Ser Tyr Leu Glu Ser Gly Val Pro Ala Arg Phe Ser
145                 150                 155                 160 ggc agt ggg tct ggg aca gac ttc acc ctc aac atc cat cct gtg gag       528
Gly Ser Gly Ser Gly Thr Asp Phe Thr Leu Asn Ile His Pro Val Glu
                165                 170                 175 gag gag gat gct gca aca tat tac tgt cag cac agt agg gag ttt ccg       576
```

-continued

```
                Glu Glu Asp Ala Ala Thr Tyr Tyr Cys Gln His Ser Arg Glu Phe Pro
                            180                 185                 190 tgg acg ttc ggt gga ggc acc aag ctg gaa atc aaa cgg gct gat gct        624
Trp Thr Phe Gly Gly Gly Thr Lys Leu Glu Ile Lys Arg Ala Asp Ala
        195                 200                 205 gca ccc ggg ggt ggc ggt tct ggc ggt ggc ggt tct gga ggc ggt ggc        672
Ala Pro Gly Gly Gly Gly Ser Gly Gly Gly Gly Ser Gly Gly Gly Gly
210                 215                 220 tct gag gtg cag ctg gtg gag tct ggg gga ggc tta gtg aag cct gga        720
Ser Glu Val Gln Leu Val Glu Ser Gly Gly Gly Leu Val Lys Pro Gly
225                 230                 235                 240 ggg tcc cgg aaa ctc tcc tgt gca gcc tct gga ttc act ttc agt aac        768
Gly Ser Arg Lys Leu Ser Cys Ala Ala Ser Gly Phe Thr Phe Ser Asn
        245                 250                 255 tat gga atg cac tgg gtc cgt cag gct cca gag aag ggg ctg gag tgg        816
Tyr Gly Met His Trp Val Arg Gln Ala Pro Glu Lys Gly Leu Glu Trp
            260                 265                 270 gtt gca tac att agt agt ggc agt agt acc atc tac tat gca gac aca        864
Val Ala Tyr Ile Ser Ser Gly Ser Ser Thr Ile Tyr Tyr Ala Asp Thr
        275                 280                 285 gtg aag ggc cga ttc acc atc tcc aga gac aat gcc aag aac acc ctg        912
Val Lys Gly Arg Phe Thr Ile Ser Arg Asp Asn Ala Lys Asn Thr Leu
290                 295                 300 ttc ctg caa atg acc agt cta agg tct gag gac aca gcc atg tat tac        960
Phe Leu Gln Met Thr Ser Leu Arg Ser Glu Asp Thr Ala Met Tyr Tyr
305                 310                 315                 320 tgt gca agg cgg ggg tta cta ctt gac tac tgg ggc caa ggc acc act       1008
Cys Ala Arg Arg Gly Leu Leu Leu Asp Tyr Trp Gly Gln Gly Thr Thr
            325                 330                 335 ctc aca gtc tcc tca gct tcc acc aag ggc cca tcc gtc ttc ccc ctg       1056
Leu Thr Val Ser Ser Ala Ser Thr Lys Gly Pro Ser Val Phe Pro Leu
        340                 345                 350 gcg ccc ctg gag tct tcc gga tcc gac atc cag atg act cag tct cca       1104
Ala Pro Leu Glu Ser Ser Gly Ser Asp Ile Gln Met Thr Gln Ser Pro
            355                 360                 365 gcc tcc cta tct gta tct gtg gga gaa act gtc acc atc aca tgt cga       1152
Ala Ser Leu Ser Val Ser Val Gly Glu Thr Val Thr Ile Thr Cys Arg
370                 375                 380 gca agt gag aat att tac agt aat tta gca tgg tat cag cag aaa cag       1200
Ala Ser Glu Asn Ile Tyr Ser Asn Leu Ala Trp Tyr Gln Gln Lys Gln
385                 390                 395                 400 gga aaa tct cct cag ctc ctg gtg tat ggt gca aca aac tta gca gat       1248
Gly Lys Ser Pro Gln Leu Leu Val Tyr Gly Ala Thr Asn Leu Ala Asp
            405                 410                 415 ggt gtg cca tca agg ttc agt ggc agt gga tca gga aca cag tat tcc       1296
Gly Val Pro Ser Arg Phe Ser Gly Ser Gly Ser Gly Thr Gln Tyr Ser
        420                 425                 430 ctc aag atc aac agc ctg cag tct gaa gat ttt ggg agt tat tac tgt       1344
Leu Lys Ile Asn Ser Leu Gln Ser Glu Asp Phe Gly Ser Tyr Tyr Cys
            435                 440                 445 caa cat ttt tgg ggt act cct ccg acg ttc ggt gga ggc acc aag ctg       1392
Gln His Phe Trp Gly Thr Pro Pro Thr Phe Gly Gly Gly Thr Lys Leu
450                 455                 460 gaa ctc aaa agg gct gat gct gca cca gga ggg gga ggg tct ggt ggg       1440
Glu Leu Lys Arg Ala Asp Ala Ala Pro Gly Gly Gly Gly Ser Gly Gly
465                 470                 475                 480 ggc ggt tcc gga ggc gga ggc tca gag gtg caa ctt gtt gag tct ggt       1488
Gly Gly Ser Gly Gly Gly Gly Ser Glu Val Gln Leu Val Glu Ser Gly
        485                 490                 495
```

-continued

| | | |
|---|---|---|
| gga gga ttg gtg cag cct aaa ggg tca ttg aaa ctc tca tgt gca gcc<br>Gly Gly Leu Val Gln Pro Lys Gly Ser Leu Lys Leu Ser Cys Ala Ala<br>500 505 510 | 1536 |
| tct gga ttc acc ttc aat acc tac ggc atg aac tgg gtc cgc cag gct<br>Ser Gly Phe Thr Phe Asn Thr Tyr Gly Met Asn Trp Val Arg Gln Ala<br>515 520 525 | 1584 |
| cca gga aag ggt ttg gaa tgg gtc ggt cgc ata aga act aaa aat aat<br>Pro Gly Lys Gly Leu Glu Trp Val Gly Arg Ile Arg Thr Lys Asn Asn<br>530 535 540 | 1632 |
| att tat gca aca tat tat gac gct tca gtg aaa gac agg ttc acc att<br>Ile Tyr Ala Thr Tyr Tyr Asp Ala Ser Val Lys Asp Arg Phe Thr Ile<br>545 550 555 560 | 1680 |
| tcc aga gat gat tca gaa agc atg ctc tat ctg caa atg aac aac ttg<br>Ser Arg Asp Asp Ser Glu Ser Met Leu Tyr Leu Gln Met Asn Asn Leu<br>565 570 575 | 1728 |
| aaa act gag gac aca gcc atg tat tac tgt gtg aga caa ggg gac gaa<br>Lys Thr Glu Asp Thr Ala Met Tyr Tyr Cys Val Arg Gln Gly Asp Glu<br>580 585 590 | 1776 |
| tta cga ggt tat gct ctg gac tac tgg ggt cag gga acc tca gtc acc<br>Leu Arg Gly Tyr Ala Leu Asp Tyr Trp Gly Gln Gly Thr Ser Val Thr<br>595 600 605 | 1824 |
| gtc tcc tca cat cta gaa caa aaa ctc atc tca gaa gag gat ctg aat<br>Val Ser Ser His Leu Glu Gln Lys Leu Ile Ser Glu Glu Asp Leu Asn<br>610 615 620 | 1872 |
| agc gcc gtc gac cat cat cat cat cat cat tga<br>Ser Ala Val Asp His His His His His His<br>625 630 | 1905 |

<210> SEQ ID NO 2
<211> LENGTH: 634
<212> TYPE: PRT
<213> ORGANISM: Artificial Sequence
<220> FEATURE:
<223> OTHER INFORMATION: Synthetic Construct

<400> SEQUENCE: 2

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Gly Ile His Asp Ile Val
                85                  90                  95

Leu Thr Gln Ser Pro Ala Ser Leu Ala Val Ser Leu Gly Gln Arg Ala
            100                 105                 110

Thr Ile Ser Cys Arg Ala Ser Lys Ser Val Ser Thr Ser Ser Tyr Ser
        115                 120                 125

Tyr Met His Trp Tyr Gln Gln Lys Pro Gly Gln Pro Pro Lys Leu Leu
    130                 135                 140

Ile Lys Tyr Ala Ser Tyr Leu Glu Ser Gly Val Pro Ala Arg Phe Ser
145                 150                 155                 160

Gly Ser Gly Ser Gly Thr Asp Phe Thr Leu Asn Ile His Pro Val Glu
                165                 170                 175

-continued

```
Glu Glu Asp Ala Ala Thr Tyr Tyr Cys Gln His Ser Arg Glu Phe Pro
            180                 185                 190

Trp Thr Phe Gly Gly Gly Thr Lys Leu Glu Ile Lys Arg Ala Asp Ala
        195                 200                 205

Ala Pro Gly Gly Gly Gly Ser Gly Gly Gly Ser Gly Gly Gly Gly
    210                 215                 220

Ser Glu Val Gln Leu Val Glu Ser Gly Gly Leu Val Lys Pro Gly
225                 230                 235                 240

Gly Ser Arg Lys Leu Ser Cys Ala Ala Ser Gly Phe Thr Phe Ser Asn
                245                 250                 255

Tyr Gly Met His Trp Val Arg Gln Ala Pro Glu Lys Gly Leu Glu Trp
            260                 265                 270

Val Ala Tyr Ile Ser Ser Gly Ser Ser Thr Ile Tyr Tyr Ala Asp Thr
        275                 280                 285

Val Lys Gly Arg Phe Thr Ile Ser Arg Asp Asn Ala Lys Asn Thr Leu
    290                 295                 300

Phe Leu Gln Met Thr Ser Leu Arg Ser Glu Asp Thr Ala Met Tyr Tyr
305                 310                 315                 320

Cys Ala Arg Arg Gly Leu Leu Leu Asp Tyr Trp Gly Gln Gly Thr Thr
                325                 330                 335

Leu Thr Val Ser Ser Ala Ser Thr Lys Gly Pro Ser Val Phe Pro Leu
            340                 345                 350

Ala Pro Leu Glu Ser Ser Gly Ser Asp Ile Gln Met Thr Gln Ser Pro
        355                 360                 365

Ala Ser Leu Ser Val Ser Val Gly Glu Thr Val Thr Ile Thr Cys Arg
    370                 375                 380

Ala Ser Glu Asn Ile Tyr Ser Asn Leu Ala Trp Tyr Gln Gln Lys Gln
385                 390                 395                 400

Gly Lys Ser Pro Gln Leu Leu Val Tyr Gly Ala Thr Asn Leu Ala Asp
                405                 410                 415

Gly Val Pro Ser Arg Phe Ser Gly Ser Gly Ser Gly Thr Gln Tyr Ser
            420                 425                 430

Leu Lys Ile Asn Ser Leu Gln Ser Glu Asp Phe Gly Ser Tyr Tyr Cys
        435                 440                 445

Gln His Phe Trp Gly Thr Pro Pro Thr Phe Gly Gly Gly Thr Lys Leu
    450                 455                 460

Glu Leu Lys Arg Ala Asp Ala Ala Pro Gly Gly Gly Gly Ser Gly Gly
465                 470                 475                 480

Gly Gly Ser Gly Gly Gly Gly Ser Glu Val Gln Leu Val Glu Ser Gly
                485                 490                 495

Gly Gly Leu Val Gln Pro Lys Gly Ser Leu Lys Leu Ser Cys Ala Ala
            500                 505                 510

Ser Gly Phe Thr Phe Asn Thr Tyr Gly Met Asn Trp Val Arg Gln Ala
        515                 520                 525

Pro Gly Lys Gly Leu Glu Trp Val Gly Arg Ile Arg Thr Lys Asn Asn
    530                 535                 540

Ile Tyr Ala Thr Tyr Tyr Asp Ala Ser Val Lys Asp Arg Phe Thr Ile
545                 550                 555                 560

Ser Arg Asp Asp Ser Glu Ser Met Leu Tyr Leu Gln Met Asn Asn Leu
                565                 570                 575

Lys Thr Glu Asp Thr Ala Met Tyr Tyr Cys Val Arg Gln Gly Asp Glu
            580                 585                 590

Leu Arg Gly Tyr Ala Leu Asp Tyr Trp Gly Gln Gly Thr Ser Val Thr
```

```
                595                 600                 605
Val Ser Ser His Leu Glu Gln Lys Leu Ile Ser Glu Glu Asp Leu Asn
    610                 615                 620

Ser Ala Val Asp His His His His His His
625                 630

<210> SEQ ID NO 3
<211> LENGTH: 522
<212> TYPE: PRT
<213> ORGANISM: Artificial Sequence
<220> FEATURE:
<223> OTHER INFORMATION: Protein sequence for bispecific scFv 3E10-3G5
      chimeric antibody derived from Mus musculus, Homo sapiens, and
      synthetic sequence from no known organism with increased
      solubility peptide but without signal sequence or epitope tag.
<220> FEATURE:
<221> NAME/KEY: MISC_FEATURE
<222> LOCATION: (1)..(4)
<223> OTHER INFORMATION: AGIH peptide for increased solubility
<220> FEATURE:
<221> NAME/KEY: MISC_FEATURE
<222> LOCATION: (5)..(522)
<223> OTHER INFORMATION: 3E10-3G5 bispecific scFv chimeric antibody with
      enhanced cell penetration mutation but no secretory signal or
      epitope tag
<220> FEATURE:
<221> NAME/KEY: MISC_FEATURE
<222> LOCATION: (5)..(5)
<223> OTHER INFORMATION: Start of 3E10 kappa light (Vk) chain from Mus
      musculus
<220> FEATURE:
<221> NAME/KEY: MISC_FEATURE
<222> LOCATION: (5)..(252)
<223> OTHER INFORMATION: 3E10 Fv fragment with enhanced cell penetration
      mutation (D31N mutation at CDR1 of 3E10 VH chain)
<220> FEATURE:
<221> NAME/KEY: MISC_FEATURE
<222> LOCATION: (5)..(121)
<223> OTHER INFORMATION: anti-DNA monoclonal antibody 3E10 kappa light
      (Vk) chain polypeptide sequence from Mus musculus
<220> FEATURE:
<221> NAME/KEY: MISC_FEATURE
<222> LOCATION: (39)..(42)
<223> OTHER INFORMATION: 3E10 kappa light (Vk) chain complementarity
      determining region 1 (CDR1) amino acid sequence from Mus musculus
<220> FEATURE:
<221> NAME/KEY: MISC_FEATURE
<222> LOCATION: (59)..(64)
<223> OTHER INFORMATION: monoclonal antibody 3E10 kappa light (Vk) chain
      CDR2 amino acid sequence from Mus musculus
<220> FEATURE:
<221> NAME/KEY: MISC_FEATURE
<222> LOCATION: (97)..(105)
<223> OTHER INFORMATION: 3E10 kappa light (Vk) chain CDR3 amino acid
      sequence from Mus musculus
<220> FEATURE:
<221> NAME/KEY: MISC_FEATURE
<222> LOCATION: (121)..(121)
<223> OTHER INFORMATION: End of 3E10 kappa light (Vk) chain from Mus
      musculus
<220> FEATURE:
<221> NAME/KEY: MISC_FEATURE
<222> LOCATION: (122)..(136)
<223> OTHER INFORMATION: (GGGGS)3 peptide linker sequence
<220> FEATURE:
<221> NAME/KEY: MISC_FEATURE
<222> LOCATION: (137)..(252)
<223> OTHER INFORMATION: anti-DNA monoclonal antibody 3E10 variable
      heavy (VH) chain polypeptide sequence from Mus Musculus with
      enhanced cell penetration mutation (D31N mutation at CDR1 of 3E10
      VH chain)
<220> FEATURE:
<221> NAME/KEY: MISC_FEATURE
<222> LOCATION: (137)..(137)
<223> OTHER INFORMATION: Start of 3E10 variable heavy (VH) chain from
      Mus musculus
```

```
<220> FEATURE:
<221> NAME/KEY: MISC_FEATURE
<222> LOCATION: (167)..(171)
<223> OTHER INFORMATION: 3E10 variable heavy (VH) chain CDR1 amino acid
      sequence from Mus musculus with D31N mutation for enhanced cell
      penetration
<220> FEATURE:
<221> NAME/KEY: MISC_FEATURE
<222> LOCATION: (167)..(167)
<223> OTHER INFORMATION: Asn amino acid; D31N mutation in CDR1 of 3E10
      variable heavy (VH) chain for enhanced cell penetration
<220> FEATURE:
<221> NAME/KEY: MISC_FEATURE
<222> LOCATION: (186)..(202)
<223> OTHER INFORMATION: 3E10 variable heavy (VH) chain CDR2 amino acid
      sequence from Mus musculus
<220> FEATURE:
<221> NAME/KEY: MISC_FEATURE
<222> LOCATION: (235)..(241)
<223> OTHER INFORMATION: 3E10 variable heavy (VH) chain CDR3 amino acid
      sequence from Mus musculus
<220> FEATURE:
<221> NAME/KEY: MISC_FEATURE
<222> LOCATION: (252)..(252)
<223> OTHER INFORMATION: End of 3E10 variable heavy (VH) chain from Mus
      musculus
<220> FEATURE:
<221> NAME/KEY: MISC_FEATURE
<222> LOCATION: (253)..(265)
<223> OTHER INFORMATION: Human constant heavy chain 1 (CH1) linker
      sequence
<220> FEATURE:
<221> NAME/KEY: MISC_FEATURE
<222> LOCATION: (266)..(271)
<223> OTHER INFORMATION: Swivel sequence
<220> FEATURE:
<221> NAME/KEY: MISC_FEATURE
<222> LOCATION: (272)..(522)
<223> OTHER INFORMATION: 3G5 Fv fragment polypeptide sequence
<220> FEATURE:
<221> NAME/KEY: MISC_FEATURE
<222> LOCATION: (272)..(384)
<223> OTHER INFORMATION: anti-MDM2 monoclonal antibody 3G5 kappa light
      (Vk) chain polypeptide sequence from Mus musculus
<220> FEATURE:
<221> NAME/KEY: MISC_FEATURE
<222> LOCATION: (272)..(272)
<223> OTHER INFORMATION: Start of 3G5 kappa light (Vk) chain from Mus
      musculus
<220> FEATURE:
<221> NAME/KEY: MISC_FEATURE
<222> LOCATION: (295)..(305)
<223> OTHER INFORMATION: 3G5 kappa light (Vk) chain complementarity
      determining region 1 (CDR1) amino acid sequence from Mus musculus
<220> FEATURE:
<221> NAME/KEY: MISC_FEATURE
<222> LOCATION: (321)..(327)
<223> OTHER INFORMATION: 3G5 kappa light (Vk) chain CDR2 amino acid
      sequence from Mus musculus
<220> FEATURE:
<221> NAME/KEY: MISC_FEATURE
<222> LOCATION: (360)..(368)
<223> OTHER INFORMATION: 3G5 kappa light (Vk) chain CDR3 amino acid
      sequence from Mus musculus
<220> FEATURE:
<221> NAME/KEY: MISC_FEATURE
<222> LOCATION: (384)..(384)
<223> OTHER INFORMATION: End of 3G5 kappa light (Vk) chain from Mus
      musculus
<220> FEATURE:
<221> NAME/KEY: MISC_FEATURE
<222> LOCATION: (385)..(399)
<223> OTHER INFORMATION: (GGGGS)3 peptide linker sequence
<220> FEATURE:
<221> NAME/KEY: MISC_FEATURE
<222> LOCATION: (400)..(522)
<223> OTHER INFORMATION: anti-MDM2 monoclonal antibody 3G5 variable
      heavy (VH) chain polypeptide sequence from Mus musculus
<220> FEATURE:
```

```
<221> NAME/KEY: MISC_FEATURE
<222> LOCATION: (400)..(400)
<223> OTHER INFORMATION: Start of 3G5 variable heavy (VH) chain from Mus
      musculus
<220> FEATURE:
<221> NAME/KEY: MISC_FEATURE
<222> LOCATION: (430)..(434)
<223> OTHER INFORMATION: 3G5 variable heavy (VH) chain CDR1 amino acid
      sequence from Mus musculus
<220> FEATURE:
<221> NAME/KEY: MISC_FEATURE
<222> LOCATION: (449)..(467)
<223> OTHER INFORMATION: 3G5 variable heavy (VH) chain CDR2 amino acid
      sequence from Mus musculus
<220> FEATURE:
<221> NAME/KEY: MISC_FEATURE
<222> LOCATION: (500)..(511)
<223> OTHER INFORMATION: 3G5 variable heavy (VH) chain CDR3 amino acid
      sequence from Mus musculus
<220> FEATURE:
<221> NAME/KEY: MISC_FEATURE
<222> LOCATION: (522)..(522)
<223> OTHER INFORMATION: End of 3G5 variable heavy (VH) chain from Mus
      musculus

<400> SEQUENCE: 3

Ala Gly Ile His Asp Ile Val Leu Thr Gln Ser Pro Ala Ser Leu Ala
1               5                   10                  15

Val Ser Leu Gly Gln Arg Ala Thr Ile Ser Cys Arg Ala Ser Lys Ser
            20                  25                  30

Val Ser Thr Ser Ser Tyr Ser Tyr Met His Trp Tyr Gln Lys Pro
        35                  40                  45

Gly Gln Pro Pro Lys Leu Leu Ile Lys Tyr Ala Ser Tyr Leu Glu Ser
    50                  55                  60

Gly Val Pro Ala Arg Phe Ser Gly Ser Gly Ser Gly Thr Asp Phe Thr
65                  70                  75                  80

Leu Asn Ile His Pro Val Glu Glu Asp Ala Ala Thr Tyr Tyr Cys
                85                  90                  95

Gln His Ser Arg Glu Phe Pro Trp Thr Phe Gly Gly Gly Thr Lys Leu
                100                 105                 110

Glu Ile Lys Arg Ala Asp Ala Ala Pro Gly Gly Gly Ser Gly Gly
            115                 120                 125

Gly Gly Ser Gly Gly Gly Ser Glu Val Gln Leu Val Glu Ser Gly
    130                 135                 140

Gly Gly Leu Val Lys Pro Gly Gly Ser Arg Lys Leu Ser Cys Ala Ala
145                 150                 155                 160

Ser Gly Phe Thr Phe Ser Asn Tyr Gly Met His Trp Val Arg Gln Ala
                165                 170                 175

Pro Glu Lys Gly Leu Glu Trp Val Ala Tyr Ile Ser Ser Gly Ser Ser
                180                 185                 190

Thr Ile Tyr Tyr Ala Asp Thr Val Lys Gly Arg Phe Thr Ile Ser Arg
            195                 200                 205

Asp Asn Ala Lys Asn Thr Leu Phe Leu Gln Met Thr Ser Leu Arg Ser
        210                 215                 220

Glu Asp Thr Ala Met Tyr Tyr Cys Ala Arg Arg Gly Leu Leu Leu Asp
225                 230                 235                 240

Tyr Trp Gly Gln Gly Thr Thr Leu Thr Val Ser Ser Ala Ser Thr Lys
                245                 250                 255

Gly Pro Ser Val Phe Pro Leu Ala Pro Leu Glu Ser Ser Gly Ser Asp
                260                 265                 270

Ile Gln Met Thr Gln Ser Pro Ala Ser Leu Ser Val Ser Val Gly Glu
```

```
                    275                 280                 285
Thr Val Thr Ile Thr Cys Arg Ala Ser Glu Asn Ile Tyr Ser Asn Leu
    290                 295                 300
Ala Trp Tyr Gln Gln Lys Gln Gly Lys Ser Pro Gln Leu Leu Val Tyr
305                 310                 315                 320
Gly Ala Thr Asn Leu Ala Asp Gly Val Pro Ser Arg Phe Ser Gly Ser
                325                 330                 335
Gly Ser Gly Thr Gln Tyr Ser Leu Lys Ile Asn Ser Leu Gln Ser Glu
            340                 345                 350
Asp Phe Gly Ser Tyr Tyr Cys Gln His Phe Trp Gly Thr Pro Pro Thr
        355                 360                 365
Phe Gly Gly Gly Thr Lys Leu Glu Leu Lys Arg Ala Asp Ala Ala Pro
    370                 375                 380
Gly Gly Gly Gly Ser Gly Gly Gly Ser Gly Gly Gly Gly Ser Glu
385                 390                 395                 400
Val Gln Leu Val Glu Ser Gly Gly Gly Leu Val Gln Pro Lys Gly Ser
                405                 410                 415
Leu Lys Leu Ser Cys Ala Ala Ser Gly Phe Thr Phe Asn Thr Tyr Gly
            420                 425                 430
Met Asn Trp Val Arg Gln Ala Pro Gly Lys Gly Leu Glu Trp Val Gly
        435                 440                 445
Arg Ile Arg Thr Lys Asn Asn Ile Tyr Ala Thr Tyr Tyr Asp Ala Ser
    450                 455                 460
Val Lys Asp Arg Phe Thr Ile Ser Arg Asp Asp Ser Glu Ser Met Leu
465                 470                 475                 480
Tyr Leu Gln Met Asn Asn Leu Lys Thr Glu Asp Thr Ala Met Tyr Tyr
                485                 490                 495
Cys Val Arg Gln Gly Asp Glu Leu Arg Gly Tyr Ala Leu Asp Tyr Trp
            500                 505                 510
Gly Gln Gly Thr Ser Val Thr Val Ser Ser
        515                 520

<210> SEQ ID NO 4
<211> LENGTH: 12
<212> TYPE: DNA
<213> ORGANISM: Mus musculus
<220> FEATURE:
<221> NAME/KEY: CDS
<222> LOCATION: (1)..(12)
<223> OTHER INFORMATION: anti-DNA monoclonal antibody 3E10 kappa light
      (Vk) chain complementarity determining region 1 (CDR1) coding
      sequence

<400> SEQUENCE: 4 agt tac atg cac                                                       12
Ser Tyr Met His
1

<210> SEQ ID NO 5
<211> LENGTH: 4
<212> TYPE: PRT
<213> ORGANISM: Mus musculus

<400> SEQUENCE: 5

Ser Tyr Met His
1

<210> SEQ ID NO 6
<211> LENGTH: 18
```

```
<212> TYPE: DNA
<213> ORGANISM: Mus musculus
<220> FEATURE:
<221> NAME/KEY: CDS
<222> LOCATION: (1)..(18)
<223> OTHER INFORMATION: anti-DNA monoclonal antibody 3E10 kappa light
      (Vk) chain complementarity determining region 2 (CDR2) coding
      sequence

<400> SEQUENCE: 6 gca tcc tac cta gaa tct                                              18
Ala Ser Tyr Leu Glu Ser
1               5

<210> SEQ ID NO 7
<211> LENGTH: 6
<212> TYPE: PRT
<213> ORGANISM: Mus musculus

<400> SEQUENCE: 7

Ala Ser Tyr Leu Glu Ser
1               5

<210> SEQ ID NO 8
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION: anti-DNA monoclonal antibody 3E10 kappa light
      (Vk) chain complementarity determining region 3 (CDR3) coding
      sequence

<400> SEQUENCE: 8 cag cac agt agg gag ttt ccg tgg acg                                  27
Gln His Ser Arg Glu Phe Pro Trp Thr
1               5

<210> SEQ ID NO 9
<211> LENGTH: 9
<212> TYPE: PRT
<213> ORGANISM: Mus musculus

<400> SEQUENCE: 9

Gln His Ser Arg Glu Phe Pro Trp Thr
1               5

<210> SEQ ID NO 10
<211> LENGTH: 15
<212> TYPE: DNA
<213> ORGANISM: Mus musculus
<220> FEATURE:
<221> NAME/KEY: CDS
<222> LOCATION: (1)..(15)
<223> OTHER INFORMATION: anti-DNA monoclonal antibody 3E10 variable
      heavy (VH) chain complementarity determining region 1 (CDR1)
      coding sequence with D31N mutation at the first amino acid
      position of CDR1 for enhanced cell penetration

<400> SEQUENCE: 10 aac tat gga atg cac                                                  15
Asn Tyr Gly Met His
1               5

<210> SEQ ID NO 11
<211> LENGTH: 5
<212> TYPE: PRT
<213> ORGANISM: Mus musculus
```

```
<400> SEQUENCE: 11

Asn Tyr Gly Met His
1               5

<210> SEQ ID NO 12
<211> LENGTH: 51
<212> TYPE: DNA
<213> ORGANISM: Mus musculus
<220> FEATURE:
<221> NAME/KEY: CDS
<222> LOCATION: (1)..(51)
<223> OTHER INFORMATION: anti-DNA monoclonal antibody 3E10 variable
      heavy (VH) chain complementarity determining region 2 (CDR2)
      coding sequence

<400> SEQUENCE: 12 tac att agt agt ggc agt agt acc atc tac tat gca gac aca gtg aag    48
Tyr Ile Ser Ser Gly Ser Ser Thr Ile Tyr Tyr Ala Asp Thr Val Lys
1               5                   10                  15 ggc                                                                51
Gly

<210> SEQ ID NO 13
<211> LENGTH: 17
<212> TYPE: PRT
<213> ORGANISM: Mus musculus

<400> SEQUENCE: 13

Tyr Ile Ser Ser Gly Ser Ser Thr Ile Tyr Tyr Ala Asp Thr Val Lys
1               5                   10                  15

Gly

<210> SEQ ID NO 14
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION: anti-DNA monoclonal antibody 3E10 variable
      heavy (VH) chain complementarity determining region 3 (CDR3)
      coding sequence

<400> SEQUENCE: 14 cgg ggg tta cta ctt gac tac                                        21
Arg Gly Leu Leu Leu Asp Tyr
1               5

<210> SEQ ID NO 15
<211> LENGTH: 7
<212> TYPE: PRT
<213> ORGANISM: Mus musculus

<400> SEQUENCE: 15

Arg Gly Leu Leu Leu Asp Tyr
1               5

<210> SEQ ID NO 16
<211> LENGTH: 33
<212> TYPE: DNA
<213> ORGANISM: Mus musculus
<220> FEATURE:
<221> NAME/KEY: CDS
<222> LOCATION: (1)..(33)
<223> OTHER INFORMATION: anti-MDM2 monoclonal antibody 3G5 kappa light
      (Vk) chain complementarity determining region 1 (CDR1) coding
``` sequence

<400> SEQUENCE: 16

```
cga gca agt gag aat att tac agt aat tta gca                    33
Arg Ala Ser Glu Asn Ile Tyr Ser Asn Leu Ala
1               5                   10
```

<210> SEQ ID NO 17
<211> LENGTH: 11
<212> TYPE: PRT
<213> ORGANISM: Mus musculus

<400> SEQUENCE: 17

```
Arg Ala Ser Glu Asn Ile Tyr Ser Asn Leu Ala
1               5                   10
```

<210> SEQ ID NO 18
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION: anti-MDM2 monoclonal antibody 3G5 kappa light
      (Vk) chain complementarity determining region 2 (CDR2) coding
      sequence

<400> SEQUENCE: 18

```
ggt gca aca aac tta gca gat                                    21
Gly Ala Thr Asn Leu Ala Asp
1               5
```

<210> SEQ ID NO 19
<211> LENGTH: 7
<212> TYPE: PRT
<213> ORGANISM: Mus musculus

<400> SEQUENCE: 19

```
Gly Ala Thr Asn Leu Ala Asp
1               5
```

<210> SEQ ID NO 20
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION: anti-MDM2 monoclonal antibody 3G5 kappa light
      (Vk) chain complementarity determining region 3 (CDR3) coding
      sequence

<400> SEQUENCE: 20

```
caa cat ttt tgg ggt act cct ccg acg                            27
Gln His Phe Trp Gly Thr Pro Pro Thr
1               5
```

<210> SEQ ID NO 21
<211> LENGTH: 9
<212> TYPE: PRT
<213> ORGANISM: Mus musculus

<400> SEQUENCE: 21

```
Gln His Phe Trp Gly Thr Pro Pro Thr
1               5
```

<210> SEQ ID NO 22

-continued

```
<211> LENGTH: 15
<212> TYPE: DNA
<213> ORGANISM: Mus musculus
<220> FEATURE:
<221> NAME/KEY: CDS
<222> LOCATION: (1)..(15)
<223> OTHER INFORMATION: anti-MDM2 monoclonal antibody 3G5 variable
      heavy (VH) chain complementarity determining region 1 (CDR1)
      coding sequence

<400> SEQUENCE: 22 acc tac ggc atg aac                                              15
Thr Tyr Gly Met Asn
1               5

<210> SEQ ID NO 23
<211> LENGTH: 5
<212> TYPE: PRT
<213> ORGANISM: Mus musculus

<400> SEQUENCE: 23

Thr Tyr Gly Met Asn
1               5

<210> SEQ ID NO 24
<211> LENGTH: 57
<212> TYPE: DNA
<213> ORGANISM: Mus musculus
<220> FEATURE:
<221> NAME/KEY: CDS
<222> LOCATION: (1)..(57)
<223> OTHER INFORMATION: anti-MDM2 monoclonal antibody 3G5 variable
      heavy (VH) chain complementarity determining region 2 (CDR2)
      coding sequence

<400> SEQUENCE: 24 cgc ata aga act aaa aat aat att tat gca aca tat tat gac gct tca   48
Arg Ile Arg Thr Lys Asn Asn Ile Tyr Ala Thr Tyr Tyr Asp Ala Ser
1               5                   10                  15 gtg aaa gac                                                      57
Val Lys Asp

<210> SEQ ID NO 25
<211> LENGTH: 19
<212> TYPE: PRT
<213> ORGANISM: Mus musculus

<400> SEQUENCE: 25

Arg Ile Arg Thr Lys Asn Asn Ile Tyr Ala Thr Tyr Tyr Asp Ala Ser
1               5                   10                  15

Val Lys Asp

<210> SEQ ID NO 26
<211> LENGTH: 36
<212> TYPE: DNA
<213> ORGANISM: Mus musculus
<220> FEATURE:
<221> NAME/KEY: CDS
<222> LOCATION: (1)..(36)
<223> OTHER INFORMATION: anti-MDM2 monoclonal antibody 3G5 variable
      heavy (VH) chain complementarity determining region 3 (CDR3)
      coding sequence

<400> SEQUENCE: 26 caa ggg gac gaa tta cga ggt tat gct ctg gac tac                  36
Gln Gly Asp Glu Leu Arg Gly Tyr Ala Leu Asp Tyr
1               5                   10
```

<210> SEQ ID NO 27
<211> LENGTH: 12
<212> TYPE: PRT
<213> ORGANISM: Mus musculus

<400> SEQUENCE: 27

Gln Gly Asp Glu Leu Arg Gly Tyr Ala Leu Asp Tyr
1               5                   10

<210> SEQ ID NO 28
<211> LENGTH: 1899
<212> TYPE: DNA
<213> ORGANISM: Artificial Sequence
<220> FEATURE:
<223> OTHER INFORMATION: Coding sequences for full length unprocessed
      bispecific scFv 3E10-PAb421 chimeric antibody derived from Mus
      musculus, Homo sapiens, Saccharomyces cerevisiae, and synthetic
      sequence from no known organism
<220> FEATURE:
<221> NAME/KEY: CDS
<222> LOCATION: (1)..(1899)
<223> OTHER INFORMATION: Coding sequences for full length unprocessed
      bispecific scFv 3E10-PAb421 chimeric antibody with secretory
      signal, protease cleavage sites, solubility enhancing peptide and
      epitope tags produced using pPicZalpha A expression vector in
      Pichia pastoris
<220> FEATURE:
<221> NAME/KEY: misc_feature
<222> LOCATION: (1)..(3)
<223> OTHER INFORMATION: ATG, start site of translation provided by
      pPicZalpha A expression vector
<220> FEATURE:
<221> NAME/KEY: misc_feature
<222> LOCATION: (1)..(267)
<223> OTHER INFORMATION: Saccharomyces cerevisiae -factor secretory
      signal coding sequence for secretion of fusion protein, provided
      by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing alpha-factor
      secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing alpha-factor
      secretory signal
<220> FEATURE:
<221> NAME/KEY: misc_feature
<222> LOCATION: (265)..(270)
<223> OTHER INFORMATION: Ste13 signal cleavage site between Ala-Ala
      encoded by nucleotide positions 265-270 for removing alpha-factor
      secretory signal
<220> FEATURE:
<221> NAME/KEY: misc_feature
<222> LOCATION: (268)..(279)
<223> OTHER INFORMATION: Ala-Gly-Ile-His peptide coding sequence for
      increasing solubility of scFv bispecific antibody
<220> FEATURE:
<221> NAME/KEY: misc_feature
<222> LOCATION: (272)..(277)
<223> OTHER INFORMATION: EcoRI restriction enzyme site, recreated after
      insertion of 3E10-PAb421 scFVc EcoRI-XbaI cDNA fragment into
      EcoRI-XbaI sites of pPicZ A expression vector
<220> FEATURE:
<221> NAME/KEY: misc_feature
<222> LOCATION: (280)..(1827)
<223> OTHER INFORMATION: 3E10-PAb421 bispecific scFv antibody coding
      sequence with enhanced cell penetration mutation
<220> FEATURE:
<221> NAME/KEY: misc_feature
<222> LOCATION: (280)..(1023)
<223> OTHER INFORMATION: 3E10 Fv fragment coding sequence with enhanced
      cell penetration mutation -continued

```
<220> FEATURE:
<221> NAME/KEY: misc_feature
<222> LOCATION: (280)..(630)
<223> OTHER INFORMATION: anti-DNA monoclonal antibody 3E10 kappa light
      (Vk) chain coding sequence from Mus musculus
<220> FEATURE:
<221> NAME/KEY: misc_feature
<222> LOCATION: (382)..(393)
<223> OTHER INFORMATION: 3E10 kappa light (Vk) chain complementarity
      determining region 1 (CDR1) coding sequence from Mus musculus
<220> FEATURE:
<221> NAME/KEY: misc_feature
<222> LOCATION: (442)..(459)
<223> OTHER INFORMATION: 3E10 kappa light (Vk) chain CDR2 coding
      sequence from Mus musculus
<220> FEATURE:
<221> NAME/KEY: misc_feature
<222> LOCATION: (556)..(582)
<223> OTHER INFORMATION: 3E10 kappa light (Vk) chain CDR3 coding
      sequence from Mus musculus
<220> FEATURE:
<221> NAME/KEY: misc_feature
<222> LOCATION: (631)..(675)
<223> OTHER INFORMATION: (GGGGS)3 peptide linker coding sequence
<220> FEATURE:
<221> NAME/KEY: misc_feature
<222> LOCATION: (766)..(780)
<223> OTHER INFORMATION: 3E10 variable heavy (VH) chain CDR1 coding
      sequence from Mus musculus with D31N mutation for enhanced cell
      penetration
<220> FEATURE:
<221> NAME/KEY: misc_feature
<222> LOCATION: (766)..(768)
<223> OTHER INFORMATION: Asn amino acid coding sequence; D31N mutation
      in the first amino acid of CDR1 of 3E10 variable heavy for
      enhanced cell penetration (VH) chain
<220> FEATURE:
<221> NAME/KEY: misc_feature
<222> LOCATION: (823)..(873)
<223> OTHER INFORMATION: 3E10 variable heavy (VH) chain CDR2 coding
      sequence from Mus musculus
<220> FEATURE:
<221> NAME/KEY: misc_feature
<222> LOCATION: (970)..(990)
<223> OTHER INFORMATION: 3E10 variable heavy (VH) chain CDR3 coding
      sequence from Mus musculus
<220> FEATURE:
<221> NAME/KEY: misc_feature
<222> LOCATION: (1024)..(1062)
<223> OTHER INFORMATION: Human constant heavy chain 1 (CH1) linker
      coding sequence
<220> FEATURE:
<221> NAME/KEY: misc_feature
<222> LOCATION: (1063)..(1080)
<223> OTHER INFORMATION: Swivel coding sequence
<220> FEATURE:
<221> NAME/KEY: misc_feature
<222> LOCATION: (1081)..(1827)
<223> OTHER INFORMATION: PAb421 Fv fragment coding sequence
<220> FEATURE:
<221> NAME/KEY: misc_feature
<222> LOCATION: (1081)..(1434)
<223> OTHER INFORMATION: anti-p53 monoclonal antibody PAb421 kappa light
      (Vk) chain coding sequence from Mus musculus
<220> FEATURE:
<221> NAME/KEY: misc_feature
<222> LOCATION: (1150)..(1197)
<223> OTHER INFORMATION: PAb421 kappa light (Vk) chain complementarity
      determining region 1 (CDR1) coding sequence from Mus musculus
<220> FEATURE:
<221> NAME/KEY: misc_feature
<222> LOCATION: (1243)..(1263)
<223> OTHER INFORMATION: PAb421 kappa light (Vk) chain complementarity
      determining region 2 (CDR2) coding sequence from Mus musculus
<220> FEATURE:
<221> NAME/KEY: misc_feature
<222> LOCATION: (1360)..(1386)
<223> OTHER INFORMATION: PAb421 kappa light (Vk) chain complementarity
      determining region 3 (CDR3) coding sequence from Mus musculus
```

```
<220> FEATURE:
<221> NAME/KEY: misc_feature
<222> LOCATION: (1435)..(1479)
<223> OTHER INFORMATION: (GGGGS)3 peptide linker coding sequence
<220> FEATURE:
<221> NAME/KEY: misc_feature
<222> LOCATION: (1480)..(1827)
<223> OTHER INFORMATION: anti-p53 monoclonal antibody PAb421 variable
      heavy (VH) chain coding sequence from Mus musculus
<220> FEATURE:
<221> NAME/KEY: misc_feature
<222> LOCATION: (1570)..(1584)
<223> OTHER INFORMATION: PAb421 variable heavy (VH) chain
      complementarity determining region 1 (CDR1) coding sequence from
      Mus musculus
<220> FEATURE:
<221> NAME/KEY: misc_feature
<222> LOCATION: (1627)..(1677)
<223> OTHER INFORMATION: PAb421 variable heavy (VH) chain
      complementarity determining region 2 (CDR2) coding sequence from
      Mus musculus
<220> FEATURE:
<221> NAME/KEY: misc_feature
<222> LOCATION: (1774)..(1794)
<223> OTHER INFORMATION: PAb421 variable heavy (VH) chain
      complementarity determining region 3 (CDR3) coding sequence from
      Mus musculus
<220> FEATURE:
<221> NAME/KEY: misc_feature
<222> LOCATION: (1830)..(1835)
<223> OTHER INFORMATION: XbaI restriction enzyme site, recreated after
      insertion of 3E10-PAb421 scFVc EcoRI-XbaI cDNA fragment into
      EcoRI-XbaI sites of pPicZalpha A expression vector
<220> FEATURE:
<221> NAME/KEY: misc_feature
<222> LOCATION: (1834)..(1863)
<223> OTHER INFORMATION: Myc epitope tag, EQKLISEEDL, coding sequence
      provided by pPicZalpha A expression vector
<220> FEATURE:
<221> NAME/KEY: misc_feature
<222> LOCATION: (1879)..(1896)
<223> OTHER INFORMATION: (His)6 epitope tag coding sequence, provided by
      pPicZalpha A expression vector
<220> FEATURE:
<221> NAME/KEY: misc_feature
<222> LOCATION: (1897)..(1899)
<223> OTHER INFORMATION: TGA, stop codon provided by pPicZ A expression
      vector

<400> SEQUENCE: 28 atg aga ttt cct tca att ttt act gct gtt tta ttc gca gca tcc tcc      48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gag aaa aga gag gct gaa gct gca gga att cac gac att gtc     288
Ser Leu Glu Lys Arg Glu Ala Glu Ala Ala Gly Ile His Asp Ile Val
                85                  90                  95 ctg aca cag tct cct gct tcc tta gct gta tct ctg ggg cag agg gcc     336
Leu Thr Gln Ser Pro Ala Ser Leu Ala Val Ser Leu Gly Gln Arg Ala
            100                 105                 110
```

| | | |
|---|---|---|
| acc atc tcc tgc agg gcc agc aaa agt gtc agt aca tct agc tat agt<br>Thr Ile Ser Cys Arg Ala Ser Lys Ser Val Ser Thr Ser Ser Tyr Ser<br>          115                      120                    125 | | 384 |
| tac atg cac tgg tac caa cag aaa cca gga cag cca ccc aaa ctc ctc<br>Tyr Met His Trp Tyr Gln Gln Lys Pro Gly Gln Pro Pro Lys Leu Leu<br>130                      135                      140 | | 432 |
| atc aag tat gca tcc tac cta gaa tct ggg gtt cct gcc agg ttc agt<br>Ile Lys Tyr Ala Ser Tyr Leu Glu Ser Gly Val Pro Ala Arg Phe Ser<br>145                      150                      155                    160 | | 480 |
| ggc agt ggg tct ggg aca gac ttc acc ctc aac atc cat cct gtg gag<br>Gly Ser Gly Ser Gly Thr Asp Phe Thr Leu Asn Ile His Pro Val Glu<br>                      165                      170                    175 | | 528 |
| gag gag gat gct gca aca tat tac tgt cag cac agt agg gag ttt ccg<br>Glu Glu Asp Ala Ala Thr Tyr Tyr Cys Gln His Ser Arg Glu Phe Pro<br>                180                      185                    190 | | 576 |
| tgg acg ttc ggt gga ggc acc aag ctg gaa atc aaa cgg gct gat gct<br>Trp Thr Phe Gly Gly Gly Thr Lys Leu Glu Ile Lys Arg Ala Asp Ala<br>            195                      200                    205 | | 624 |
| gca ccc ggg ggt ggc ggt tct ggc ggt ggc ggt tct gga ggc ggt ggc<br>Ala Pro Gly Gly Gly Gly Ser Gly Gly Gly Gly Ser Gly Gly Gly Gly<br>210                      215                      220 | | 672 |
| tct gag gtg cag ctg gtg gag tct ggg gga ggc tta gtg aag cct gga<br>Ser Glu Val Gln Leu Val Glu Ser Gly Gly Gly Leu Val Lys Pro Gly<br>225                      230                      235                    240 | | 720 |
| ggg tcc cgg aaa ctc tcc tgt gca gcc tct gga ttc act ttc agt aac<br>Gly Ser Arg Lys Leu Ser Cys Ala Ala Ser Gly Phe Thr Phe Ser Asn<br>                      245                      250                    255 | | 768 |
| tat gga atg cac tgg gtc cgt cag gct cca gag aag ggg ctg gag tgg<br>Tyr Gly Met His Trp Val Arg Gln Ala Pro Glu Lys Gly Leu Glu Trp<br>                260                      265                    270 | | 816 |
| gtt gca tac att agt agt ggc agt agt acc atc tac tat gca gac aca<br>Val Ala Tyr Ile Ser Ser Gly Ser Ser Thr Ile Tyr Tyr Ala Asp Thr<br>            275                      280                    285 | | 864 |
| gtg aag ggc cga ttc acc atc tcc aga gac aat gcc aag aac acc ctg<br>Val Lys Gly Arg Phe Thr Ile Ser Arg Asp Asn Ala Lys Asn Thr Leu<br>290                      295                      300 | | 912 |
| ttc ctg caa atg acc agt cta agg tct gag gac aca gcc atg tat tac<br>Phe Leu Gln Met Thr Ser Leu Arg Ser Glu Asp Thr Ala Met Tyr Tyr<br>305                      310                      315                    320 | | 960 |
| tgt gca agg cgg ggg tta cta ctt gac tac tgg ggc caa ggc acc act<br>Cys Ala Arg Arg Gly Leu Leu Leu Asp Tyr Trp Gly Gln Gly Thr Thr<br>                      325                      330                    335 | | 1008 |
| ctc aca gtc tcc tca gct tcc acc aag ggc cca tcc gtc ttc ccc ctg<br>Leu Thr Val Ser Ser Ala Ser Thr Lys Gly Pro Ser Val Phe Pro Leu<br>                340                      345                    350 | | 1056 |
| gcg ccc ctg gag tct tcc gga tcc gat gtt gtg atg acc cag act cca<br>Ala Pro Leu Glu Ser Ser Gly Ser Asp Val Val Met Thr Gln Thr Pro<br>            355                      360                    365 | | 1104 |
| ctc act ttg tcg gtt acc att gga caa cca gcc tcc atc tct tgc aag<br>Leu Thr Leu Ser Val Thr Ile Gly Gln Pro Ala Ser Ile Ser Cys Lys<br>370                      375                      380 | | 1152 |
| tca agt cag agc ctc ttg gat agt gat gga aag aca tac ttg aat tgg<br>Ser Ser Gln Ser Leu Leu Asp Ser Asp Gly Lys Thr Tyr Leu Asn Trp<br>385                      390                      395                    400 | | 1200 |
| ttg tta cag agg cca ggc cag tct cca aag cgc cta atc tat ctg gtg<br>Leu Leu Gln Arg Pro Gly Gln Ser Pro Lys Arg Leu Ile Tyr Leu Val<br>                      405                      410                    415 | | 1248 |
| tct aaa ctg gac tct gga gtc cct gac agg ttc act ggc agt gga tca<br>Ser Lys Leu Asp Ser Gly Val Pro Asp Arg Phe Thr Gly Ser Gly Ser<br>                420                      425                    430 | | 1296 |

```
ggg aca gat ttc aca ctg aaa atc aac aga gtg gag gct gag gat ttg    1344
Gly Thr Asp Phe Thr Leu Lys Ile Asn Arg Val Glu Ala Glu Asp Leu
            435                 440                 445 gga gtt tat tat tgc tgg caa ggt aca cat tct ccg ctc acg ttc ggt    1392
Gly Val Tyr Tyr Cys Trp Gln Gly Thr His Ser Pro Leu Thr Phe Gly
    450                 455                 460 gct ggc acc aag ctg gaa att aaa cgg gct gac gct gca ccc ggg gga    1440
Ala Gly Thr Lys Leu Glu Ile Lys Arg Ala Asp Ala Ala Pro Gly Gly
465                 470                 475                 480 ggg gga tct ggt ggc ggc gga tca ggt gga ggt gga tct cag gtg cag    1488
Gly Gly Ser Gly Gly Gly Gly Ser Gly Gly Gly Gly Ser Gln Val Gln
                485                 490                 495 ctg cag cag tct ggg gca gag ctt gtg agg tca ggg gcc tca gtc aag    1536
Leu Gln Gln Ser Gly Ala Glu Leu Val Arg Ser Gly Ala Ser Val Lys
            500                 505                 510 ttg tcc tgc aca gct tct ggc ttc aac att aaa gac tac tat atg cac    1584
Leu Ser Cys Thr Ala Ser Gly Phe Asn Ile Lys Asp Tyr Tyr Met His
    515                 520                 525 tgg gtg aag cag agg cct gaa cag ggc ctg gag tgg att gga tgg att    1632
Trp Val Lys Gln Arg Pro Glu Gln Gly Leu Glu Trp Ile Gly Trp Ile
530                 535                 540 gat cct gag aat ggt gat act gaa tat gcc ccg aag ttc cag ggc aag    1680
Asp Pro Glu Asn Gly Asp Thr Glu Tyr Ala Pro Lys Phe Gln Gly Lys
545                 550                 555                 560 gcc act atg act gca gac aca tcc tcc gat aca gcc tac ctg cag ctc    1728
Ala Thr Met Thr Ala Asp Thr Ser Ser Asp Thr Ala Tyr Leu Gln Leu
            565                 570                 575 agc agc ctg gca tct gag gac act gcc gtc tat tat tgt aat ttt tac    1776
Ser Ser Leu Ala Ser Glu Asp Thr Ala Val Tyr Tyr Cys Asn Phe Tyr
    580                 585                 590 ggg gat gct ttg gac tac tgg ggt caa gga acc tcg gtc acc gtc tcc    1824
Gly Asp Ala Leu Asp Tyr Trp Gly Gln Gly Thr Ser Val Thr Val Ser
595                 600                 605 tct cat cta gaa caa aaa ctc atc tca gaa gag gat ctg aat agc gcc    1872
Ser His Leu Glu Gln Lys Leu Ile Ser Glu Glu Asp Leu Asn Ser Ala
            610                 615                 620 gtc gac cat cat cat cat cat cat tga                                1899
Val Asp His His His His His His
625                 630
```

<210> SEQ ID NO 29
<211> LENGTH: 632
<212> TYPE: PRT
<213> ORGANISM: Artificial Sequence
<220> FEATURE:
<223> OTHER INFORMATION: Synthetic Construct

<400> SEQUENCE: 29

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Ala Gly Ile His Asp Ile Val
```

-continued

```
                85                  90                  95
Leu Thr Gln Ser Pro Ala Ser Leu Ala Val Ser Leu Gly Gln Arg Ala
            100                 105                 110
Thr Ile Ser Cys Arg Ala Ser Lys Ser Val Ser Thr Ser Ser Tyr Ser
            115                 120                 125
Tyr Met His Trp Tyr Gln Gln Lys Pro Gly Gln Pro Pro Lys Leu Leu
            130                 135                 140
Ile Lys Tyr Ala Ser Tyr Leu Glu Ser Gly Val Pro Ala Arg Phe Ser
145                 150                 155                 160
Gly Ser Gly Ser Gly Thr Asp Phe Thr Leu Asn Ile His Pro Val Glu
                165                 170                 175
Glu Glu Asp Ala Ala Thr Tyr Tyr Cys Gln His Ser Arg Glu Phe Pro
                180                 185                 190
Trp Thr Phe Gly Gly Gly Thr Lys Leu Glu Ile Lys Arg Ala Asp Ala
                195                 200                 205
Ala Pro Gly Gly Gly Gly Ser Gly Gly Gly Gly Ser Gly Gly Gly Gly
            210                 215                 220
Ser Glu Val Gln Leu Val Glu Ser Gly Gly Gly Leu Val Lys Pro Gly
225                 230                 235                 240
Gly Ser Arg Lys Leu Ser Cys Ala Ala Ser Gly Phe Thr Phe Ser Asn
                245                 250                 255
Tyr Gly Met His Trp Val Arg Gln Ala Pro Glu Lys Gly Leu Glu Trp
            260                 265                 270
Val Ala Tyr Ile Ser Ser Gly Ser Ser Thr Ile Tyr Tyr Ala Asp Thr
            275                 280                 285
Val Lys Gly Arg Phe Thr Ile Ser Arg Asp Asn Ala Lys Asn Thr Leu
            290                 295                 300
Phe Leu Gln Met Thr Ser Leu Arg Ser Glu Asp Thr Ala Met Tyr Tyr
305                 310                 315                 320
Cys Ala Arg Arg Gly Leu Leu Leu Asp Tyr Trp Gly Gln Gly Thr Thr
                325                 330                 335
Leu Thr Val Ser Ser Ala Ser Thr Lys Gly Pro Ser Val Phe Pro Leu
                340                 345                 350
Ala Pro Leu Glu Ser Ser Gly Ser Asp Val Val Met Thr Gln Thr Pro
            355                 360                 365
Leu Thr Leu Ser Val Thr Ile Gly Gln Pro Ala Ser Ile Ser Cys Lys
            370                 375                 380
Ser Ser Gln Ser Leu Leu Asp Ser Asp Gly Lys Thr Tyr Leu Asn Trp
385                 390                 395                 400
Leu Leu Gln Arg Pro Gly Gln Ser Pro Lys Arg Leu Ile Tyr Leu Val
                405                 410                 415
Ser Lys Leu Asp Ser Gly Val Pro Asp Arg Phe Thr Gly Ser Gly Ser
                420                 425                 430
Gly Thr Asp Phe Thr Leu Lys Ile Asn Arg Val Glu Ala Glu Asp Leu
            435                 440                 445
Gly Val Tyr Tyr Cys Trp Gln Gly Thr His Ser Pro Leu Thr Phe Gly
            450                 455                 460
Ala Gly Thr Lys Leu Glu Ile Lys Arg Ala Asp Ala Ala Pro Gly Gly
465                 470                 475                 480
Gly Gly Ser Gly Gly Gly Gly Ser Gly Gly Gly Gly Ser Gln Val Gln
                485                 490                 495
Leu Gln Gln Ser Gly Ala Glu Leu Val Arg Ser Gly Ala Ser Val Lys
                500                 505                 510
```

```
Leu Ser Cys Thr Ala Ser Gly Phe Asn Ile Lys Asp Tyr Tyr Met His
            515                 520                 525

Trp Val Lys Gln Arg Pro Glu Gln Gly Leu Glu Trp Ile Gly Trp Ile
        530                 535                 540

Asp Pro Glu Asn Gly Asp Thr Glu Tyr Ala Pro Lys Phe Gln Gly Lys
545                 550                 555                 560

Ala Thr Met Thr Ala Asp Thr Ser Ser Asp Thr Ala Tyr Leu Gln Leu
                565                 570                 575

Ser Ser Leu Ala Ser Glu Asp Thr Ala Val Tyr Tyr Cys Asn Phe Tyr
            580                 585                 590

Gly Asp Ala Leu Asp Tyr Trp Gly Gln Gly Thr Ser Val Thr Val Ser
        595                 600                 605

Ser His Leu Glu Gln Lys Leu Ile Ser Glu Glu Asp Leu Asn Ser Ala
    610                 615                 620

Val Asp His His His His His His
625                 630

<210> SEQ ID NO 30
<211> LENGTH: 520
<212> TYPE: PRT
<213> ORGANISM: Artificial Sequence
<220> FEATURE:
<223> OTHER INFORMATION: Protein sequence for bispecific scFv 3E10-
      PAb421 chimeric antibody derived from Mus musculus, Homo sapiens,
      and synthetic sequence from no known organism with increased
      solubility peptide but without signal sequence or epitope tag.
<220> FEATURE:
<221> NAME/KEY: MISC_FEATURE
<222> LOCATION: (1)..(4)
<223> OTHER INFORMATION: AGIH peptide for increased solubility
<220> FEATURE:
<221> NAME/KEY: MISC_FEATURE
<222> LOCATION: (5)..(520)
<223> OTHER INFORMATION: 3E10-PAb4215 bispecific scFv chimeric antibody
      with enhanced cell penetration mutation but no secretory signal or
      epitope tag
<220> FEATURE:
<221> NAME/KEY: MISC_FEATURE
<222> LOCATION: (5)..(5)
<223> OTHER INFORMATION: Start of 3E10 kappa light (Vk) chain from Mus
      musculus
<220> FEATURE:
<221> NAME/KEY: MISC_FEATURE
<222> LOCATION: (5)..(252)
<223> OTHER INFORMATION: 3E10 Fv fragment with enhanced cell penetration
      mutation (D31N mutation at CDR1 of 3E10 VH chain)
<220> FEATURE:
<221> NAME/KEY: MISC_FEATURE
<222> LOCATION: (5)..(121)
<223> OTHER INFORMATION: anti-DNA monoclonal antibody 3E10 kappa light
      (Vk) chain polypeptide sequence from Mus musculus
<220> FEATURE:
<221> NAME/KEY: MISC_FEATURE
<222> LOCATION: (39)..(42)
<223> OTHER INFORMATION: 3E10 kappa light (Vk) chain complementarity
      determining region 1 (CDR1) amino acid sequence from Mus musculus
<220> FEATURE:
<221> NAME/KEY: MISC_FEATURE
<222> LOCATION: (59)..(64)
<223> OTHER INFORMATION: 3E10 kappa light (Vk) chain CDR2 amino acid
      sequence from Mus musculus
<220> FEATURE:
<221> NAME/KEY: MISC_FEATURE
<222> LOCATION: (97)..(105)
<223> OTHER INFORMATION: 3E10 kappa light (Vk) chain CDR3 amino acid
      sequence from Mus musculus
<220> FEATURE:
<221> NAME/KEY: MISC_FEATURE
<222> LOCATION: (121)..(121)
<223> OTHER INFORMATION: End of 3E10 kappa light (Vk) chain from Mus
```

```
                     musculus
<220> FEATURE:
<221> NAME/KEY: MISC_FEATURE
<222> LOCATION: (122)..(136)
<223> OTHER INFORMATION: (GGGGS)3 peptide linker sequence
<220> FEATURE:
<221> NAME/KEY: MISC_FEATURE
<222> LOCATION: (137)..(252)
<223> OTHER INFORMATION: anti-DNA monoclonal antibody 3E10 variable
      heavy (VH) chain polypeptide sequence from Mus musculus with
      enhanced cell penetration mutation (D31N mutation at CDR1 of 3E10
      VH chain)
<220> FEATURE:
<221> NAME/KEY: MISC_FEATURE
<222> LOCATION: (137)..(137)
<223> OTHER INFORMATION: Start of 3E10 variable heavy (VH) chain from
      Mus musculus
<220> FEATURE:
<221> NAME/KEY: MISC_FEATURE
<222> LOCATION: (167)..(171)
<223> OTHER INFORMATION: 3E10 variable heavy (VH) chain CDR1 amino acid
      sequence from Mus musculus with D31N mutation for enhanced cell
      penetration
<220> FEATURE:
<221> NAME/KEY: MISC_FEATURE
<222> LOCATION: (167)..(167)
<223> OTHER INFORMATION: Asn amino acid; D31N mutation in first amino
      acid of CDR1 of 3E10 variable heavy (VH) chain for enhanced cell
      penetration
<220> FEATURE:
<221> NAME/KEY: MISC_FEATURE
<222> LOCATION: (186)..(202)
<223> OTHER INFORMATION: 3E10 variable heavy (VH) chain CDR2 amino acid
      sequence from Mus musculus
<220> FEATURE:
<221> NAME/KEY: MISC_FEATURE
<222> LOCATION: (235)..(241)
<223> OTHER INFORMATION: 3E10 variable heavy (VH) chain CDR3 amino acid
      sequence from Mus musculus
<220> FEATURE:
<221> NAME/KEY: MISC_FEATURE
<222> LOCATION: (252)..(252)
<223> OTHER INFORMATION: End of 3E10 variable heavy (VH) chain from Mus
      musculus
<220> FEATURE:
<221> NAME/KEY: MISC_FEATURE
<222> LOCATION: (253)..(265)
<223> OTHER INFORMATION: Human constant heavy chain 1 (CH1) linker
      sequence
<220> FEATURE:
<221> NAME/KEY: MISC_FEATURE
<222> LOCATION: (266)..(271)
<223> OTHER INFORMATION: Swivel sequence
<220> FEATURE:
<221> NAME/KEY: MISC_FEATURE
<222> LOCATION: (272)..(520)
<223> OTHER INFORMATION: PAb421 Fv fragment polypeptide sequence
<220> FEATURE:
<221> NAME/KEY: MISC_FEATURE
<222> LOCATION: (272)..(389)
<223> OTHER INFORMATION: anti-p53 monoclonal antibody PAb421 kappa light
      (Vk) chain polypeptide sequence from Mus musculus
<220> FEATURE:
<221> NAME/KEY: MISC_FEATURE
<222> LOCATION: (272)..(272)
<223> OTHER INFORMATION: Start of PAb421 kappa light (Vk) chain from Mus
      musculus
<220> FEATURE:
<221> NAME/KEY: MISC_FEATURE
<222> LOCATION: (295)..(310)
<223> OTHER INFORMATION: PAb421 kappa light (Vk) chain complementarity
      determining region 1 (CDR1) amino acid sequence from Mus musculus
<220> FEATURE:
<221> NAME/KEY: MISC_FEATURE
<222> LOCATION: (326)..(332)
<223> OTHER INFORMATION: PAb421 kappa light (Vk) chain CDR2 amino acid
      sequence from Mus musculus
<220> FEATURE:
<221> NAME/KEY: MISC_FEATURE
```

```
<222> LOCATION: (365)..(373)
<223> OTHER INFORMATION: PAb421 kappa light (Vk) chain CDR3 amino acid
      sequence from Mus musculus
<220> FEATURE:
<221> NAME/KEY: MISC_FEATURE
<222> LOCATION: (389)..(389)
<223> OTHER INFORMATION: End of PAb421 kappa light (Vk) chain from Mus
      musculus
<220> FEATURE:
<221> NAME/KEY: MISC_FEATURE
<222> LOCATION: (390)..(404)
<223> OTHER INFORMATION: (GGGGS)3 peptide linker sequence
<220> FEATURE:
<221> NAME/KEY: MISC_FEATURE
<222> LOCATION: (405)..(520)
<223> OTHER INFORMATION: anti-p53 monoclonal antibody PAb421 variable
      heavy (VH) chain polypeptide sequence from Mus musculus
<220> FEATURE:
<221> NAME/KEY: MISC_FEATURE
<222> LOCATION: (405)..(405)
<223> OTHER INFORMATION: Start of PAb421 variable heavy (VH) chain from
      Mus musculus
<220> FEATURE:
<221> NAME/KEY: MISC_FEATURE
<222> LOCATION: (435)..(439)
<223> OTHER INFORMATION: PAb421 variable heavy (VH) chain CDR1 amino
      acid sequence from Mus musculus
<220> FEATURE:
<221> NAME/KEY: MISC_FEATURE
<222> LOCATION: (454)..(470)
<223> OTHER INFORMATION: PAb421 variable heavy (VH) chain CDR2 amino
      acid sequence from Mus musculus
<220> FEATURE:
<221> NAME/KEY: MISC_FEATURE
<222> LOCATION: (503)..(509)
<223> OTHER INFORMATION: PAb421 variable heavy (VH) chain CDR3 amino
      acid sequence from Mus musculus
<220> FEATURE:
<221> NAME/KEY: MISC_FEATURE
<222> LOCATION: (520)..(520)
<223> OTHER INFORMATION: End of PAb421 variable heavy (VH) chain from
      Mus musculus

<400> SEQUENCE: 30

Ala Gly Ile His Asp Ile Val Leu Thr Gln Ser Pro Ala Ser Leu Ala
1               5                   10                  15

Val Ser Leu Gly Gln Arg Ala Thr Ile Ser Cys Arg Ala Ser Lys Ser
            20                  25                  30

Val Ser Thr Ser Ser Tyr Ser Tyr Met His Trp Tyr Gln Gln Lys Pro
        35                  40                  45

Gly Gln Pro Pro Lys Leu Leu Ile Lys Tyr Ala Ser Tyr Leu Glu Ser
    50                  55                  60

Gly Val Pro Ala Arg Phe Ser Gly Ser Gly Ser Gly Thr Asp Phe Thr
65                  70                  75                  80

Leu Asn Ile His Pro Val Glu Glu Glu Asp Ala Ala Thr Tyr Tyr Cys
                85                  90                  95

Gln His Ser Arg Glu Phe Pro Trp Thr Phe Gly Gly Gly Thr Lys Leu
            100                 105                 110

Glu Ile Lys Arg Ala Asp Ala Ala Pro Gly Gly Gly Gly Ser Gly Gly
        115                 120                 125

Gly Gly Ser Gly Gly Gly Gly Ser Glu Val Gln Leu Val Glu Ser Gly
    130                 135                 140

Gly Gly Leu Val Lys Pro Gly Gly Ser Arg Lys Leu Ser Cys Ala Ala
145                 150                 155                 160

Ser Gly Phe Thr Phe Ser Asn Tyr Gly Met His Trp Val Arg Gln Ala
                165                 170                 175

Pro Glu Lys Gly Leu Glu Trp Val Ala Tyr Ile Ser Ser Gly Ser Ser
```

```
            180             185             190
Thr Ile Tyr Tyr Ala Asp Thr Val Lys Gly Arg Phe Thr Ile Ser Arg
        195                 200                 205
Asp Asn Ala Lys Asn Thr Leu Phe Leu Gln Met Thr Ser Leu Arg Ser
210                 215                 220
Glu Asp Thr Ala Met Tyr Tyr Cys Ala Arg Arg Gly Leu Leu Leu Asp
225                 230                 235                 240
Tyr Trp Gly Gln Gly Thr Thr Leu Thr Val Ser Ser Ala Ser Thr Lys
                245                 250                 255
Gly Pro Ser Val Phe Pro Leu Ala Pro Leu Glu Ser Ser Gly Ser Asp
                260                 265                 270
Val Val Met Thr Gln Thr Pro Leu Thr Leu Ser Val Thr Ile Gly Gln
            275                 280                 285
Pro Ala Ser Ile Ser Cys Lys Ser Ser Gln Ser Leu Leu Asp Ser Asp
            290                 295                 300
Gly Lys Thr Tyr Leu Asn Trp Leu Leu Gln Arg Pro Gly Gln Ser Pro
305                 310                 315                 320
Lys Arg Leu Ile Tyr Leu Val Ser Lys Leu Asp Ser Gly Val Pro Asp
                325                 330                 335
Arg Phe Thr Gly Ser Gly Ser Gly Thr Asp Phe Thr Leu Lys Ile Asn
                340                 345                 350
Arg Val Glu Ala Glu Asp Leu Gly Val Tyr Tyr Cys Trp Gln Gly Thr
            355                 360                 365
His Ser Pro Leu Thr Phe Gly Ala Gly Thr Lys Leu Glu Ile Lys Arg
            370                 375                 380
Ala Asp Ala Ala Pro Gly Gly Gly Ser Gly Gly Gly Ser Gly
385                 390                 395                 400
Gly Gly Gly Ser Gln Val Gln Leu Gln Gln Ser Gly Ala Glu Leu Val
                405                 410                 415
Arg Ser Gly Ala Ser Val Lys Leu Ser Cys Thr Ala Ser Gly Phe Asn
                420                 425                 430
Ile Lys Asp Tyr Tyr Met His Trp Val Lys Gln Arg Pro Glu Gln Gly
            435                 440                 445
Leu Glu Trp Ile Gly Trp Ile Asp Pro Glu Asn Gly Asp Thr Glu Tyr
            450                 455                 460
Ala Pro Lys Phe Gln Gly Lys Ala Thr Met Thr Ala Asp Thr Ser Ser
465                 470                 475                 480
Asp Thr Ala Tyr Leu Gln Leu Ser Ser Leu Ala Ser Glu Asp Thr Ala
                485                 490                 495
Val Tyr Tyr Cys Asn Phe Tyr Gly Asp Ala Leu Asp Tyr Trp Gly Gln
                500                 505                 510
Gly Thr Ser Val Thr Val Ser Ser
                515                 520

<210> SEQ ID NO 31
<211> LENGTH: 48
<212> TYPE: DNA
<213> ORGANISM: Mus musculus
<220> FEATURE:
<221> NAME/KEY: CDS
<222> LOCATION: (1)..(48)
<223> OTHER INFORMATION: anti-p53 monoclonal antibody PAb421 kappa light
      (Vk) chain complementarity determining region 1 (CDR1) amino acid
      sequence from Mus musculus

<400> SEQUENCE: 31
```

```
aag tca agt cag agc ctc ttg gat agt gat gga aag aca tac ttg aat        48
Lys Ser Ser Gln Ser Leu Leu Asp Ser Asp Gly Lys Thr Tyr Leu Asn
1               5                   10                  15
```

<210> SEQ ID NO 32
<211> LENGTH: 16
<212> TYPE: PRT
<213> ORGANISM: Mus musculus

<400> SEQUENCE: 32

```
Lys Ser Ser Gln Ser Leu Leu Asp Ser Asp Gly Lys Thr Tyr Leu Asn
1               5                   10                  15
```

<210> SEQ ID NO 33
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION: anti-p53 monoclonal antibody PAb421 kappa light
      (Vk) chain complementarity determining region 2 (CDR2) amino acid
      sequence from Mus musculus

<400> SEQUENCE: 33

```
ctg gtg tct aaa ctg gac tct                                            21
Leu Val Ser Lys Leu Asp Ser
1               5
```

<210> SEQ ID NO 34
<211> LENGTH: 7
<212> TYPE: PRT
<213> ORGANISM: Mus musculus

<400> SEQUENCE: 34

```
Leu Val Ser Lys Leu Asp Ser
1               5
```

<210> SEQ ID NO 35
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION: anti-p53 monoclonal antibody PAb421 kappa light
      (Vk) chain complementarity determining region 3 (CDR3) amino acid
      sequence from Mus musculus

<400> SEQUENCE: 35

```
tgg caa ggt aca cat tct ccg ctc acg                                    27
Trp Gln Gly Thr His Ser Pro Leu Thr
1               5
```

<210> SEQ ID NO 36
<211> LENGTH: 9
<212> TYPE: PRT
<213> ORGANISM: Mus musculus

<400> SEQUENCE: 36

```
Trp Gln Gly Thr His Ser Pro Leu Thr
1               5
```

<210> SEQ ID NO 37
<211> LENGTH: 15
<212> TYPE: DNA
<213> ORGANISM: Mus musculus
<220> FEATURE:

```
<221> NAME/KEY: CDS
<222> LOCATION: (1)..(15)
<223> OTHER INFORMATION: anti-p53 monoclonal antibody PAb421 variable
      heavy (VH) chain complementarity determining region 1 (CDR1)
      coding sequence

<400> SEQUENCE: 37 gac tac tat atg cac                                              15
Asp Tyr Tyr Met His
1               5

<210> SEQ ID NO 38
<211> LENGTH: 5
<212> TYPE: PRT
<213> ORGANISM: Mus musculus

<400> SEQUENCE: 38

Asp Tyr Tyr Met His
1               5

<210> SEQ ID NO 39
<211> LENGTH: 51
<212> TYPE: DNA
<213> ORGANISM: Mus musculus
<220> FEATURE:
<221> NAME/KEY: CDS
<222> LOCATION: (1)..(51)
<223> OTHER INFORMATION: anti-p53 monoclonal antibody PAb421 variable
      heavy (VH) chain complementarity determining region 2 (CDR2)
      coding sequence

<400> SEQUENCE: 39 tgg att gat cct gag aat ggt gat act gaa tat gcc ccg aag ttc cag    48
Trp Ile Asp Pro Glu Asn Gly Asp Thr Glu Tyr Ala Pro Lys Phe Gln
1               5                   10                  15 ggc                                                              51
Gly

<210> SEQ ID NO 40
<211> LENGTH: 17
<212> TYPE: PRT
<213> ORGANISM: Mus musculus

<400> SEQUENCE: 40

Trp Ile Asp Pro Glu Asn Gly Asp Thr Glu Tyr Ala Pro Lys Phe Gln
1               5                   10                  15

Gly

<210> SEQ ID NO 41
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION: anti-p53 monoclonal antibody PAb421 variable
      heavy (VH) chain complementarity determining region 3 (CDR3)
      coding sequence

<400> SEQUENCE: 41 tac ggg gat gct ttg gac tac                                      21
Tyr Gly Asp Ala Leu Asp Tyr
1               5

<210> SEQ ID NO 42
<211> LENGTH: 7
<212> TYPE: PRT
```

```
<213> ORGANISM: Mus musculus

<400> SEQUENCE: 42

Tyr Gly Asp Ala Leu Asp Tyr
1               5
```

TARGETING INTRACELLULAR TARGET-BINDING DETERMINANTS WITH INTRACELLULAR ANTIBODIES

CROSS-REFERENCE TO RELATED APPLICATIONS

This patent application is a continuation of U.S. application Ser. No. 15/042,106, filed Feb. 11, 2016 (now U.S. Pat. No. 10,686,363), which is a divisional of U.S. of application Ser. No. 13/844,318, filed Mar. 15, 2013 (now U.S. Pat. No. 9,283,272), and which claims the benefit of the filing date of U.S. Ser. No. 61/618,613, filed Mar. 30, 2012. The content of these earlier filed applications is hereby incorporated herein by reference in its entirety.

SEQUENCE LISTING

The present application contains a Sequence Listing that has been submitted via EFS-Web in the parent application (U.S. application Ser. No. 5/042,106, now U.S. Pat. No. 10,686,363), and Applicant requests that the U.S. Patent and Trademark Office transfer a copy of that Sequence Listing to the present application. The Sequence Listing is hereby incorporated by reference into the present application in its entirety pursuant to 37 C.F.R. § 1.52(e)(5).

Throughout this application various publications are referenced. The disclosures of these publications in their entireties are hereby incorporated by reference into this application in order to more fully describe the state of the art to which this invention pertains.

BACKGROUND OF THE INVENTION

Current therapies are largely based on the use of small molecules to target intracellular sites, because cells are impervious to large molecules such as proteins. However, small molecule inhibitors are prone to have undesirable side effects as a result of binding unintended targets. By contrast, antibodies have excellent binding specificity, but most do not penetrate living cells. Thus, the current use of therapeutic antibodies is limited to targeting molecules that are secreted or located on the cell membrane. Intracellular antibodies can be generated by gene therapy, but the potential dangers have not justified its use. Cell-penetrating peptides (CPPs) also referred to as protein transduction domains (PTDs) are currently used to transport proteins into cells (Chugh A, Eudes F, Shim Y-S. Cell-penetrating peptides: Nanocarrier for macromolecule delivery in living cells. IUBMB Life, 62: 183-193, 2010). However, an important limitation of these intracellular transporters is that they may be targeted to endosomes through lipid rafts. In addition, some are highly cationic peptides that have been shown to be toxic to normal cells (Toborek, M; Lee, Y W; Pu, H; Malecki, A; Flora, G; Garrido, R; Hennig, B; Bauer, H C; Nath, A. HIV-Tat protein induces oxidative and inflammatory pathways in brain endothelium. *J. Neurochem.* 2003; 84(1), 169-179; Pu, H; Tian, J; Flora, G; Lee, Y W; Nath, A; Hennig, B; Toborek, M. HIV-1 Tat protein upregulates inflammatory mediators and induces monocyte invasion into the brain. *Mol. Cell. Neurosci.* 2003). We identified a unique monoclonal anti-DNA antibody, mAb 3E10 described (Weisbart R H, et al. *J Immunol.* 1990 144(7): 2653-2658; ATCC Accession No. PTA 2439 hybridoma), which penetrates living cells and localizes in the nucleus without apparent harm (Zack, D. J., Stempniak, M., Wong, A. L., Taylor, C., Weisbart, R. H.: Mechanisms of cellular penetration and nuclear localization of an anti-double strand DNA autoantibody. J. Immunol., 157:2082-2088, 1996). In contrast to CCPs, mAb 3E10 and its single-chain Fv fragment (scFv) are internalized through hENT2, an equilibrative nucleoside salvage pathway (Hansen J E, Tse C M, Chan G, Heinze E R, Nishimura R N, Weisbart R H. Intranuclear protein transduction through a nucleoside salvage pathway. J Biol Chem. 2007 Jul. 20; 282(29):20790-3. Epub 2007 May 24). hENT2 is expressed in most cells, but its expression is increased in muscle and cancer cells. On the basis of these findings, we developed the Fv fragment of 3E10 as an intracellular delivery system for large molecules (Weisbart, R. H., Stempniak, M., Harris, S., Zack, D. J., and Ferreri, K.: An autoantibody is modified for use as a delivery system to target the cell nucleus: Therapeutic implications. J. Autoimmun., 11:539-546, 1998; Weisbart, R. H., Baldwin, R., Huh, B., Zack, D. J., and Nishimura, R.: Novel protein transfection of primary rat cortical neurons utilizing an antibody that penetrates living cells. J. Immunol., 164:6020-6026, 2000; Weisbart, R. H., Wakelin, R., Chan, G., Miller, C. W. and Koeffler, P. H. Construction and expression of a bispecific single-chain antibody that penetrates mutant p53 colon cancer cells and binds p53. International Journal of Oncology, Int. J. Onc. 25:1113-1118, 2004; Weisbart, R. H., Hansen, J., Chan, G., Wakellin, R., Chang, S., Heinze, E., Miller, C. W., Koeffler, H. P., Yang, F., Cole, G. M., Min, Y., and Nishimura, R. Antibody-mediated transduction of p53 into cancer cells. Int. J. Onc. 25:1867-1873, 2004; Hansen J E, Sohn W., Kim C, Chang S S, Huang N C, Santos D G, Chan G, Weisbart R H, Nishimura R N. Antibody-mediated Hsp70 protein therapy. Brain Res. 2006 1088:187-96; Hansen, J E; Fischer, L K; Chan, G; Chang, S S; Baldwin, S W; Aragon, R J; Carter, J J; Lilly, M; Nishimura, R N; Reeves, M E; Weisbart, R H. Antibody-mediated p53 protein therapy prevents liver metastasis in vivo. Cancer Res. 2007; 67(4); Heinze E, Baldwin S, Chan G, Hansen J, Song J, Clements D, Aragon R, Nishimura R, Reeves M, Weisbart R. Antibody-mediated FOXP3 protein therapy induces apoptosis in cancer cells in vitro and inhibits metastasis in vivo. Int J Oncol. 2009 July; 35(1):167-73; Heinze E, Chan G, Mory R, Khavari R, Alavi A, Chung S Y, Nishimura R N, Weisbart R H. Tumor suppressor and T-regulatory functions of Foxp3 are mediated through separate signaling pathways. Oncology Letters. Published online May, 2011). After localizing in the cell nucleus, 3E10 scFv is largely degraded within 4 hours, thus minimizing potential toxicity.

The exquisite specificity of antibody-antigen interactions is ideal for therapeutic applications, but the therapeutic use of antibodies is limited to extracellular targets because of limited access of antibodies into cells. We developed a method to deliver antibodies into cells as bispecific single-chain Fv fragments constructed with the Fv fragment of a cell-penetrating monoclonal antibody, 3E10, which localizes to the nucleus. Since Mdm2 is an important cancer target, we selected an anti-Mdm2 monoclonal antibody, mAb 3G5, for intracellular transport to target Mdm2-dependent cancer cells. 3G5 was shown previously to bind critical residues L66, Y67, and E69 at the N-terminus of Mdm2 required for binding to p53, and was, therefore, an excellent candidate to serve as a competitive inhibitor of Mdm2 (Chen J, Marechal V, and Levine, A J. Mapping of the p53 and mdm-2 Interaction Domains. Molecular and Cellular Biology, 13:4107-4114, 1993; Bottger A, Bottger V, Garcia-Echeverria C, Chene P, Hochkeppel H K, Sampson W, Ang K., Howard, S F., Picksley S M, Lane D P. Molecular characterization of the hdm2-p53 interaction. J. Mol. Biol. 269: 744-56, 2007; Elizabeth Rayburn, Ruiwen Zhang, Jie He and Hui Wang. MDM2 and Human Malignancies: Expression, Clinical Pathology, Prognostic Markers, and Implications for Chemotherapy. Current Cancer Drug Targets, 5:27-41, 2005; Shangary S and Wang S. Small-molecule inhibitors of the MDM2-p53 protein-protein interaction to reactivate p53 function: a novel approach for cancer therapy. Annu. Rev. Pharmacol. Toxicol. 49:223-41, 2009; Lane, D P. New insights into p53 based therapy. Discovery Medicine. Published online, Aug. 18, 2011). Mdm2 is an E3 ubiquitin ligase that down-regulates p53 function, but it also has p53-independent growth-inhibitory functions.

Our invention demonstrates the feasibility of transporting antibodies into cells for therapeutic regulation of intracellular targets and the possibility for enhanced or synergistic inhibition of the growth of tumor cells when multiple components of a regulatory pathway are targeted with more than one therapeutic agent; furthermore, our invention provides novel reagents for treatment of tumors, cancers, diseases and disregulated processes along with a rationale for their combined use in targeting a regulatory pathway disregulated in tumor cells, or alternatively, components of any number of pathways that might be disregulated within tumors, cancers, diseases or conditions.

SUMMARY OF THE INVENTION

The invention provides bispecific antibodies having Fv fragments with a cell-penetrating determinant and a second Fv fragment with an intracellular target-binding determinant. In one embodiment, the intracellular target-binding determinant is an E3 ubiquitin-protein ligase, or tumor suppressor-interacting protein, such as MDM2. In one embodiment, the intracellular target-binding determinant may target an oncoprotein such as a myc or ras oncoprotein. In another embodiment, the intracellular target-binding determinant may target DNA repair proteins such as a RAD52 protein, ataxia telangiectasia mutated protein (ATM), CHK2 or CHK1 proteins, BCL2 protein. Additional examples of proteins associated with DNA repair include but are not limited BRCA1, MDC1, 53BP1, p53, ATR, and p21.

In one embodiment, the Fv fragment with the cell penetrating determinant is a 3E10 Fv. Additionally, in one embodiment the second Fv fragment with an intracellular target-binding determinant is a 3G5 Fv.

The 3E10 bispecific antibodies of the invention may further comprise one or more amino acid sequence comprising Ala-Gly-Ile-His (AGIH) at the amino terminus of one or both of the Fv region.

The 3E10 bispecific antibodies of the invention may be joined or attached to localizing signals so as to direct the scFvs to intracellular compartments such as endoplasmic reticulum and mitochondria. Further, the 3E10 bispecific antibodies of the invention may incorporate enzyme cleavage sites to separate the scFvs once they are transported into cells. Additionally, the 3E10 bispecific antibodies of the invention may be joined to produce bispecific scFvs that bind peptides attached to siRNAs as a method to use bispecific scFvs to transport siRNA into cells.

The invention provides method for regulating intracellular targets with a bispecific antibody comprising contacting a cell with a bispecific antibody having a Fv fragment with a cell-penetrating determinant and a second Fv fragment with an intracellular target-binding determinant.

The invention provides a method for inhibiting an intracellular target in a cell with a bispecific antibody comprising contacting the cell with a bispecific antibody having a first recombinant variable region of an immunoglobulin molecule with a cell-penetrating determinant (e.g. Fv fragment of mAb 3E10). Preferably the first recombinant variable region causes the bispecific antibody to enter the cell. Additionally, the bispecific antibody has a second recombinant variable region of an immunoglobulin molecule with an intracellular target-binding determinant (e.g. Fv fragment of mAb 3G5) under suitable conditions so that it binds the intracellular target in the cell so that the bispecific antibody inhibits the intracellular target.

The invention provides a method for inhibiting an intracellular target in a cell with a bispecific antibody comprising contacting the cell with a bispecific antibody having a first Fv fragment with a cell-penetrating determinant and a second Fv fragment with an intracellular target-binding determinant under suitable conditions so that the first Fv fragment causes the bispecific antibody to enter the cell and the second Fv fragment binds the intracellular target in the cell and thereby inhibiting the intracellular target.

The invention also provides a method for increasing p53 tumor suppressor protein levels in a tumor or cancer cell by exposing the cancer cell with a bispecific antibody having a first Fv fragment with a cell-penetrating determinant and a second Fv fragment with an intracellular target-binding determinant, thereby increasing the level of p53 tumor suppressor protein levels in a tumor or cancer cell.

The invention further provides a method for inhibiting the growth of MDM2-addicted tumor or cancer cells in a subject by exposing the tumor or cancer cell to a bispecific antibody comprising a Fv fragment with a cell-penetrating determinant of anti-DNA monoclonal antibody 3E10 and a second Fv fragment with an intracellular target-binding determinant for MDM2, thereby inhibiting the growth of tumor or cancer cells in the subject.

The invention also provides a method for regulating activity of MDM2-interacting proteins with a bispecific antibody comprising contacting a cell with a bispecific antibody having a Fv fragment with a cell-penetrating determinant and a second Fv fragment with a binding determinant for MDM2.

The invention further provides a method for increasing therapeutic effectiveness of treating tumor, cancer or a dis-regulated intracellular process comprising the use of combination therapy with a bispecific antibody comprising: (a) a Fv fragment with a cell-penetrating determinant and a second Fv fragment with an intracellular target-binding determinant, and (b) a second bispecific antibody comprising a Fv fragment with a cell-penetrating determinant and an additional second Fv fragment with an intracellular target-binding determinant for a second protein of the same biochemical pathway, intracellular signaling pathway, or regulatory network.

In one embodiment, the invention provides a bispecific antibody comprising a first Fv fragment with a cell-penetrating determinant from an anti-DNA monoclonal antibody 3E10 or an antibody which competes with monoclonal antibody 3E10 and a second Fv fragment with an intracellular target-binding determinant that inhibits the biological activity, biochemical activity, regulatory activity or cellular signal associated with the determinant or a macromolecule to which the determinant is attached.

In one embodiment, the invention provides a bispecific antibody having the amino acid sequence of SEQ ID NO:2.

In another embodiment, the invention provides a bispecific antibody encoded by nucleic acid sequence, as shown in SEQ ID NO:1.

In yet another embodiment, the invention provides a bispecific antibody comprising one or more of amino acid sequence of SEQ ID NOS:3, 5, 7, 9, 11, 13, 15, 17, 19, 21, 23, 25, or 27.

In a further embodiment, the invention provides a bispecific antibody encoded by a nucleic acid sequence, comprising nucleic acid sequence as shown in SEQ ID NO:1 from nucleotide position 268 to 1833, or SEQ ID NOS:4, 6, 8, 10, 12, 14, 16, 18, 20, 22, 24, or 26.

In one embodiment, the invention provides a second bispecific antibody having the amino acid sequence of SEQ ID NO:29.

In another embodiment, the invention provides a second bispecific antibody encoded by nucleic acid sequence, as shown in SEQ ID NO:28.

In yet another embodiment, the invention provides a bispecific antibody comprising one or more of amino acid sequence of SEQ ID NOS:30, 5, 7, 9, 11, 13, 15, 32, 34, 36, 38, 40, or 42.

In a further embodiment, the invention provides a bispecific antibody encoded by a nucleic acid sequence, comprising nucleic acid sequence as shown in SEQ ID NO:28 from nucleotide position 268 to 1827, or SEQ ID NOS:4, 6, 8, 10, 12, 14, 31, 33, 35, 37, 39, or 41.

In additional embodiment, the invention contemplates disclosed amino acid sequence of a bispecific antibody comprising conservative amino acid substitution or substitutions.

In additional embodiment, the invention contemplates disclosed nucleic acid sequence for a bispecific antibody comprising silent mutation or mutations.

The invention also provides a bispecific antibody or a single chain antibody comprising one or more of gly-gly-gly-gly-serine repeat(s), human CH1 linker, and a swivel sequence.

BRIEF DESCRIPTION OF THE FIGURES

FIGS. 1A-D show that the 3E10-3G5 bispecific antibody retains the MDM2-binding activity of 3G5 and the cell-penetrating activity of 3E10. FIG. 1A is a schematic of the 3E10-3G5 bispecific antibody. FIG. 1B shows purified 3E10-3G5 visualized by SDS-PAGE and GelCode Blue® staining. A single band is observed at the expected molecular weight of ~60 kDa. FIG. 1C shows Western blots of MC-7 cell lysates probed with control, 3G5, or 3E10-3G5 demonstrate that both 3G5 and 3E10-3G5 recognize and bind MDM2. FIG. 1D shows that 3E10-3G5 penetrates COS-7 cells and localizes to the nucleus similar to 3E10 scFv alone as evidenced by anti-myc staining.

FIGS. 2A-C show that 3E10-3G5 impairs the growth of MDM2-addicted melanoma cells. FIG. 2A shows the dose-response effect of 3E10-3G5 on growth of UACC-257 cells. Shown is mean response±S.D. of duplicate determinations. There was no effect of 3E10 or 3G5 alone. FIG. 2B shows that the growth of human melanoma cells (SK-MEL-103, SK-MEL-147, UACC-62, UACC-257) was inhibited at day 3 by 10 µM 3E10-3G5 compared to medium alone. Results are representative of 3 independent experiments and are shown as mean±S.D. 3T3 are transformed mouse fibroblasts, and BJ is a culture of normal human primary fibroblasts. FIG. 2C shows microscopy images demonstrating the differences in cell population and morphology of melanoma cells 3 days after treatment with 3E10-3G5 compared to control buffer, 3E10 alone, and 3G5 alone.

FIGS. 3A-D show that 3E10-3G5 inhibits human melanoma xenograft growth in vivo. Nude mice were injected subcutaneously with $1 \times 10^6$ UACC-257 cells on day 1 and then observed (FIG. 3A) control group or (FIG. 3B) treated by i.p. administration of 1.0 mg 3E10-3G5 on days 1-4. FIG. 3C shows the mean tumor volume±SEM after injection of cells into control and treated mice. FIG. 3D shows that tumors in mice treated with 3E10-3G5 exhibit increased levels of p53 and MDM2 as demonstrated by Western blotting for p53 and MDM2 in tumors from three control and three 3E10-3G5-treated mice.

FIG. 4 shows the sequence of 3E10-3G5 bispecific scFv cloned between EcoRI and XbaI in pPicZαA. FIG. 4 shows the nucleic acid sequence provided in SEQ ID NO: 1 and the encoded polypeptide sequence in SEQ ID NO: 2.

FIG. 5 shows the nucleic acid sequence provided in SEQ ID NO: 28 and the encoded polypeptide sequence in SEQ ID NO: 29.

FIGS. 7A-D show bar graphs of (FIG. 7A) HT-29 cells on day 4; (FIG. 7B) HT-29 cells on day 7; (FIG. 7C) U-251 cells on day 4; and (FIG. 7D) LN319 cells on day 7 in which combined 3E10-3G5 and 3E10-PAb421 bispecific antibody treatment results in enhanced or synergistic inhibition on growth of human cancer cells in vitro.

Figure 5:
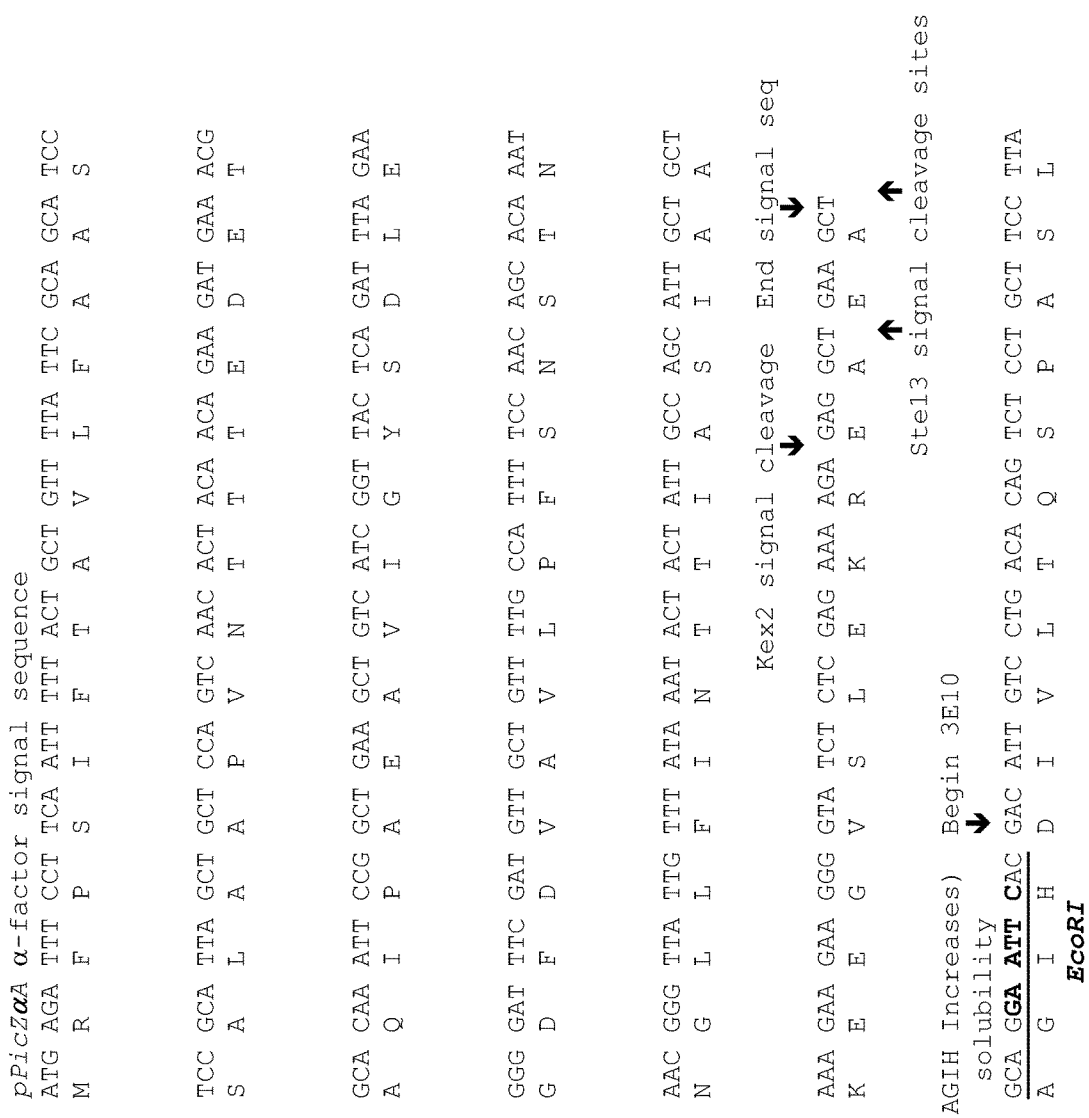
FIG. 5 shows the sequence of 3E10-PAb421 bispecific scFv cloned between EcoRI and XbaI in pPicZαA.

| Summary Table of SEQ ID NO and Description | |
|---|---|
| SEQ ID NO: | DESCRIPTION |
| 1 | 3E10-3G5 coding sequence with initiator and epitope tags nucleic and amino acid |
| 2 | 3E10-3G5 coding sequence with initiator and epitope tags amino acid |
| 3 | 3E10-3G5 bispecific antibody with AGIH and no initiator or epitope tags amino acid |
| 4 | 3E10 kappa light chain CDR1 nucleic and amino acid |
| 5 | 3E10 kappa light chain CDR1 amino acid |
| 6 | 3E10 kappa light chain CDR2 nucleic and amino acid |
| 7 | 3E10 kappa light chain CDR2 amino acid |
| 8 | 3E10 kappa light chain CDR3 nucleic and amino acid |
| 9 | 3E10 kappa light chain CDR3 amino acid |
| 10 | 3E10 VH chain CDR1 with D31N mutation nucleic and amino acid |
| 11 | 3E10 VH chain CDR1 with D31N mutation amino acid |
| 12 | 3E10 VH chain CDR2 nucleic and amino acid |
| 13 | 3E10 VH chain CDR2 amino acid |
| 14 | 3E10 VH chain CDR3 nucleic and amino acid |
| 15 | 3E10 VH chain CDR3 amino acid |
| 16 | 3G5 kappa light chain CDR1 nucleic and amino acid |
| 17 | 3G5 kappa light chain CDR1 amino acid |
| 18 | 3G5 kappa light chain CDR2 nucleic and amino acid |
| 19 | 3G5 kappa light chain CDR2 amino acid |
| 20 | 3G5 kappa light chain CDR3 nucleic and amino acid |
| 21 | 3G5 kappa light chain CDR3 amino acid |
| 22 | 3G5 VH chain CDR1 nucleic and amino acid |
| 23 | 3G5 VH chain CDR1 amino acid |
| 24 | 3G5 VH chain CDR2 nucleic and amino acid |
| 25 | 3G5 VH chain CDR2 amino acid |

-continued

Summary Table of SEQ ID NO and Description

| SEQ ID NO: | DESCRIPTION |
|---|---|
| 26 | 3G5 VH chain CDR3 nucleic and amino acid |
| 27 | 3G5 VH chain CDR3 amino acid |
| 28 | 3E10-PAb421 complete coding sequence with initiator and epitope tags nucleic and amino acid |
| 29 | 3E10-PAb421 complete coding sequence with initiator and epitope tags amino acid |
| 30 | 3E10-PAb421 bispecific antibody with AGIH and no initiator or epitope tag amino acid |
| 31 | PAb421 kappa light chain CDR1 nucleic and amino acid |
| 32 | PAb421 kappa light chain CDR1 amino acid |
| 33 | PAb421 kappa light chain CDR2 nucleic and amino acid |
| 34 | PAb421 kappa light chain CDR2 amino acid |
| 35 | PAb421 kappa light chain CDR3 nucleic and amino acid |
| 36 | PAb421 kappa light chain CDR3 amino acid |
| 37 | PAb421 VH chain CDR1 nucleic and amino acid |
| 38 | PAb421 VH chain CDR1 amino acid |
| 39 | PAb421 VH chain CDR2 nucleic and amino acid |
| 40 | PAb421 VH chain CDR2 amino acid |
| 41 | PAb421 VH chain CDR3 nucleic and amino acid |
| 42 | PAb421 VH chain CDR3 amino acid |

DETAILED DESCRIPTION OF THE INVENTION

Definitions

To facilitate understanding of the invention, a number of terms are defined below.

As used herein, a "bispecific antibody" means any immunologically reactive molecule which specifically recognizes and binds at least two different targets at alternate times or at the same time. The immunologically reactive molecule may be a single polypeptide chain as for example in bispecific antibody comprising two or more single chain FIT (scFv) fragments. The immunologically reactive molecule may consist of more than one polypeptide chains such as bispecific antibodies created from two antibodies with differing antigen specificity held together by disulfide bonds, chemical crosslinkers, or bridging agents which function to bring the two different antibodies together.

Typically, a "bispecific antibody" will contain the variable region of a heavy chain and a light chain or portions thereof to permit recognition of a target as well as a second variable region of a heavy chain and a light chain or portions thereof of an antibody to permit recognition of a second target.

The "bispecific antibody" may also include a constant region of heavy and/or light chain. However, a constant region is optional. Also, when the bispecific antibody includes a constant region of a heavy and/or light chain, it may be the entire constant region or a portion thereof.

A "bispecific antibody" also includes its equivalent, in which at least one determinant of the "bispecific antibody" is replaced with a non immunoglobulin sequence-related polypeptide or agent that recognizes one or more of the targets. Such non immunoglobulin sequence-related peptide or agent could be discovered through screening of phage display libraries, peptide libraries, cDNA libraries or non-peptide libraries, such as cell penetrating peptides or aptamers. In addition to peptides or aptamers, non immunoglobulin sequence-related agent could include nucleic acid, RNA or DNA, as well as carbohydrate or lipid and their derivatives.

A "bispecific antibody" includes heteroconjugates with binding specificities for at least two different targets. For example a heteroconjugates includes a hybrid antibody created from linking two different antibodies or antibody fragments or a hybrid of an antibody or antibody fragment linked to a lectin or lectin fragment or another determinant with an intracellular binding specificity or a cell penetrating ability, so long as the heteroconjugates have binding specificities for at least two targets.

A "bispecific antibody" includes heteroconjugates in which a "bispecific antibody" is coupled to a therapeutic agent (e.g., chemotherapeutic agent or toxin) or an imaging agent (e.g., radioisotope).

A "bispecific antibody" may be produced by recombinant DNA methods in which coding sequences of immunoglobulin genes are manipulated to produce the "bispecific antibody." The coding sequences of the immunoglobulin genes may be used in its entirety, mutated at specific sequences or codons, or used partially by truncating the coding sequences to produce the "bispecific antibody" or components that results in production of a "bispecific antibody."

A "bispecific antibody" includes an intact antibody or a Fv fragment, Fab, Fab' or F(ab')2 fragment coupled chemically, disulphide bridges or by other means to a second determinant which specifically recognizes at least a different target than the target recognized by the intact antibody or the Fv, Fab, Fab' or F(ab')2 fragment. The second determinant includes an second intact antibody different from the binding specificity of the first antibody or the Fv, Fab, Fab' or F(ab')2 fragment of the second antibody.

A "bispecific antibody" of the invention includes antibodies with not only binding specificities for two targets but also include antibodies with additional determinants, which may be derived from immunoglobulin sequences or non-immunoglubulin sequences, with specificities for other target(s).

A "bispecific antibody" includes recombinant variable regions of an immunoglobulin molecule. The F(ab') from two different antibodies may be linked under oxidative condition to form disulphide bonds or may be linked by chemical coupling or through recombinant DNA methods.

A "bispecific antibody" includes chimeric antibodies, recombinant antibodies, humanized antibodies or human antibodies or their derivatives.

A "bispecific antibody" includes antibodies of the invention in which one or more of the complementarity determining region (CDR) of the invention is used to screen for additional antibodies or agents that can compete with the binding of the 3E10, 3G5 or PAb421 antibodies. Peptide, phage display, cDNA, or chemical libraries may be used for such a screen.

As used herein, "anti-DNA monoclonal antibody 3E10" (also referred to herein as 3E10 antibody or mAb 3E10) refers to an antibody produced by ATCC PTA 2439 or a functional fragment or variant thereof or an antibody having the specificity of mAb 3E10. The full 3E10 antibody has been previously described (Weisbart R H, et al. J Immunol. 1990 144(7): 2653-2658; ATCC Accession No. PTA 2439 hybridoma).

As used herein "recombinant variable regions of immunoglobulin molecules" refers to variable regions of Ig molecules which are produced by molecular biological means. Sequences encoding variable domain of the heavy and light chains may be isolated from T-cells, B-cells, leukemic cells, lymphoma cells, or immunoglobulin gene expressing cells, cloned into expression vector systems, and introduced into a host cell to produce "recombinant variable regions of immunoglobulin molecules." Alternatively, the sequences may be recombinantly produced or obtained from genomic DNA. Recombinant antibodies produced in this manner consists of an antibody or antibody fragment with the antigen binding specificity dependent on the variable region, comprising framework sequences and CDRs. Such recombinant antibodies may be formed from a polypeptide chain containing a variable region from a light chain and a polypeptide chain containing a variable region from a heavy chain or alternatively both the light chain and heavy chain variable regions could be found within a polypeptide in which a linker is used to link by recombinant DNA methods the coding sequences for the two variable chain regions, such as in the case of single chain Fv fragment (scFv).

When "recombinant variable regions of immunoglobulin molecules" are formed from two separate polypeptides, one for the light chain variable region and other for the heavy chain variable region, the recombinant Ig molecules may be an intact antibody as is normally produced by an organism from which the coding sequences were isolated or it could be a fragment. Antibody fragments could be produced either by recombinant DNA methods allowing tailored antibodies not dependent on specific protease cleavage sites or by proteolytic cleavage of the recombinant antibodies such as by IdeS, pepsin, or papain to produce Fab, F(ab') or F(ab')2 fragments. The "recombinant variable regions of immunoglobulin molecules" may include the entire constant region or a portion of the constant region. In addition, the constant region of one antibody may be replaced by recombinant DNA method with the constant region of a different antibody if desired.

"Single-chain antibodies" or "Fv" consist of an antibody light chain variable domain or region ("$V_L$") and heavy chain variable region ("$V_H$") connected by a short peptide linker. The peptide linker allows the structure to assume a conformation which is capable of binding to antigen [Bird et al., (1988) Science 242:423 and Huston et al. (1988) Proc. Natl. Acad. Sci. USA 85:5879].

As used herein, a "conservative amino acid substitution" is the replacement of one amino acid with another of a similar type such that the binding specificity of the antibody is preserved. Amino acids of a similar type can be classified into several groups in which one amino acid within a group may be able to substitute for another member of the group:

(1) non-polar aliphatic amino acids, such as alanine, glycine, isoleucine, leucine and valine with alanine and glycine more related to each other and isoleucine, leucine and valine more related to each other based on size;
(2) neutral polar amino acids, such as serine, cysteine, threonine, glutamine and asparagines, and to a lesser extent methionine;
(3) cyclic amino acid, such as proline;
(4) aromatic amino acids, such as phenylalanine, tyrosine, and tryptophan;
(5) basic amino acids, such as histidine, lysine and arginine;
(6) acidic amino acids, such as aspartic acid, glutamic acid, asparagine and glutamine;
(7) aspartic acid and asparagines;
(8) glutamic acid and glutamine; and
(9) alanine, glycine, serine and cysteine Discussions of conservative amino acid substitution may be found in the patent literature as well as in U.S. Pat. Nos. 5,264,558 and 7,700,544.

Moreover, the present invention includes nucleic acids with "silent mutation" or "silent mutations." A silent mutation is a mutation in the DNA which does not result in a change to the amino acid sequence of a protein or results in a change to the amino acid sequence of a protein but not its functionality. Degeneracy of the genetic code allows multiple codons to code for the same amino acid, allowing silent mutations to occur without changing the protein sequence. Such silent mutations are well-known and may be recited readily from publically available and accepted codon tables. In the case of silent mutations in which the amino acid sequence is changed but not the function of the protein, such silent mutations are generally mutations in which one amino acid of a certain chemical/physical characteristics is substituted with another of a similar type. Such mutations may involve conservative amino acid substitutions and may be detected through evolutionary changes but is best determine empirically.

Administration is preferably by methods including, but not limited to, intramuscular injection, subcutaneous injection, nasal spray and other mucosal delivery, intradermal injection with electroporation, electroincorporation, ultrasound, jet injector, and topical patches.

According to the present invention, where administration includes a pharmaceutical formulation, preferably the formulation is a unit dosage containing a daily dose or unit, daily sub-dose or an appropriate fraction thereof, of the active ingredient.

The compositions of the invention can be administered by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, compositions of the invention may be administered alone but may generally be administered in admixture with a suitable pharmaceutical excipient diluent or carrier selected with regard to the intended route of administration and standard pharmaceutical practice.

In embodiments of the present invention in which polypeptides or polynucleotides of the invention are administered parenterally, such administration can be, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Methods of the Invention

The invention provides a method for inhibiting an intracellular target in a cell with a bispecific antibody comprising contacting the cell with a bispecific antibody having a first recombinant variable region of an immunoglobulin molecule with a cell-penetrating determinant (e.g. Fv fragment of mAb 3E10). Preferably the first recombinant variable region causes the bispecific antibody to enter the cell. Additionally, the bispecific antibody has a second recombinant variable region of an immunoglobulin molecule with an intracellular target-binding determinant (e.g. Fv fragment of mAb 3G5) under suitable conditions so that it binds the intracellular target in the cell so that the bispecific antibody inhibits the intracellular target.

In one embodiment, the bispecific antibody is a chimeric, human or humanized antibody. In another embodiment, the bispecific antibody comprises a chimeric, human or humanized bispecific single-chain Fv fragment.

In one embodiment, the first recombinant variable region with a cell-penetrating determinant (e.g. Fv fragment of mAb 3E10) is derived from an anti-DNA antibody. The anti-DNA antibody may be a monoclonal antibody. In one embodiment, the monoclonal antibody is a mAb 3E10 or an antibody that competes with monoclonal antibody 3E10 and is internalizing.

In another embodiment, the first recombinant variable region with a cell-penetrating determinant (e.g. Fv fragment of mAb 3E10) is derived from an antibody transported into a cell through a salvage pathway. The salvage pathway may be a nucleoside salvage pathway which may be mediated by equilibrative nucleoside transporters (ENTs) or SLC29 family of integral membrane proteins. The equilibrative nucleoside transporter (ENT) or a member of the SLC29 family of integral membrane proteins may be a transporter for purine and pyrimidine nucleosides and nucleobases or a metabolite thereof. Further, the transporter for purine and pyrimidine nucleosides and nucleobases or a metabolite thereof may be a human equilibrative nucleoside transporter ENT2.

In yet another embodiment, the antibody transported into a cell through a salvage pathway may be a monoclonal antibody.

In one embodiment, the first Fv fragment comprises one or more complementarity determining regions (CDRs) of mAb 3E10, as specified in SEQ ID NOS:5, 7, 9, 11, 13, and 15.

In another embodiment, the first Fv fragment comprises a CDR with at least 50% amino acid sequence identity or homology to SEQ ID NOS: 5, 7, 9, 11, 13, or 15.

In another embodiment, the first recombinant variable region with a cell-penetrating determinant (e.g. Fv fragment) comprises an anti-DNA monoclonal antibody 3E10 idiotype or an idiotype that competes with monoclonal antibody 3E10 and is internalizing.

In one embodiment, the bispecific antibody is a chimeric, human or humanized antibody that competes with anti-DNA monoclonal antibody 3E10. The antibody that competes with monoclonal antibody 3E10 may be a chimeric, human or humanized antibody that competes with the uptake of anti-DNA monoclonal antibody 3E10 into a cell.

In another embodiment, the uptake of anti-DNA monoclonal antibody 3E10 into a cell is through the equilibrative nucleoside transporter (ENTs) or a member of the SLC29 family of integral membrane proteins expressed by the cell. The equilibrative nucleoside transporter (ENTs) or a member of the SLC29 family of integral membrane proteins is human ENT2.

In one embodiment, the cell with a bispecific antibody is from a mammal. Mammals may include but are not limited to mouse, rat, hamster, cat, dog, rabbit, bovine, pig, sheep, goat, horse, monkey and human.

In one embodiment, the second recombinant variable region with an intracellular target-binding determinant (e.g. Fv fragment of mAb 3G5 or mAb PAb421) is derived from an antibody directed against a cytosolic, nuclear, mitochondrial, endoplasmic reticulum, membrane, and/or organelle macromolecule.

In another embodiment, the second recombinant variable region with an intracellular target-binding determinant (e.g. Fv fragment of mAb 3G5 or mAb PAb421) is derived from an anti-idiotypic antibody directed against an idiotope, a set of idiotopes or an idiotype of an antibody directed against cytosolic, nuclear, mitochondrial, endoplasmic reticulum, membrane, and/or organelle macromolecule. The macromolecule may be a protein, lipid, DNA, or RNA. Further, the protein, lipid, DNA, or RNA macromolecule is modified with a carbohydrate, phosphate group, carboxylic acid group, methyl group, sulfate group, lipid, hydroxyl group, amide group, amino acid, modified amino acid, selenium, ubiquitin, or SUMO protein, or contains a modified base or oxidized base, and combinations thereof.

In yet another embodiment, the macromolecule is a human protein associated with control of cell growth and proliferation, cell cycle, DNA repair, DNA integrity, transcription, replication, translation, or intracellular transport. Examples of protein include but are not limited to Mdm2, BRCA1, MDC1, 53BP1, p53, ATM, ATR, CHK1, CHK2, WT1 (Dao, T. et al., Sci Transl Med, 2013, 5(176):176ra33) or p21.

In another embodiment, the second recombinant variable region with an intracellular target-binding determinant (e.g. Fv fragment) is derived from an anti-oncoprotein antibody or an anti-idiotypic antibody of an anti-oncoprotein antibody. In one embodiment, the anti-oncoprotein antibody or the anti-idiotypic antibody may be a monoclonal antibody and the monoclonal antibody may be directed to the Mdm2 oncoprotein (e.g. mAb 3G5). In an embodiment, the monoclonal antibody is directed to the WT1 oncoprotein (e.g., mAb ESK1).

In another embodiment, the monoclonal antibody is directed to a binding partner of a tumor suppressor protein. In one embodiment, the binding partner of a tumor suppressor protein is Mdm2 oncoprotein. In another embodiment, the tumor suppressor protein is p53 protein.

In one embodiment, the monoclonal antibody is directed to an E3 ubiquitin ligase. In another embodiment, the monoclonal antibody disrupts the binding of an oncoprotein to a tumor suppressor protein. The binding of an oncoprotein to a tumor suppressor protein is the binding of Mdm2 to p53, respectively.

In one embodiment, the bispecific antibody is largely degraded within 4 hours.

The invention also provides a method for increasing p53 tumor suppressor protein levels in a tumor or cancer cell by exposing the cancer cell with a bispecific antibody having a first recombinant variable region with a cell-penetrating determinant (e.g. Fv fragment of mAb 3E10) and a second recombinant variable region with an intracellular target-binding determinant (e.g. Fv fragment of mAb 3G5), thereby increasing the level of p53 tumor suppressor protein levels in a tumor or cancer cell.

In one embodiment, the tumor or cancer is a melanoma, soft tissue tumors, sarcomas, Ewing's sarcoma, leiomyosarcomas, lipomas, liposarcomas, malignant fibrous histiocytomas, malignant Schwannomas, rhabdomyosarcomas, osteosarcomas, brain tumors, central nervous system gliomas, neuroblastoma, glioblastomas, astrocytomas, oligodendrogliomas, soft tissue sarcomas, osteosarcomas, breast cancer, cervical carcinomas, ovarian carcinomas, testicular tumors, urothelial carcinomas, esophageal carcinomas, lung cancers, non-small cell lung carcinoma (NSCLC), nasopharyngeal carcinomas, colorectal cancer, or colon cancer.

The invention further provides a method for inhibiting the growth of tumor or cancer cells in a subject by exposing the tumor or cancer cell to a bispecific antibody of the invention.

The invention also provides a method for inhibiting the growth of MDM2-addicted tumor or cancer cells in a subject by exposing the tumor or cancer cell to a bispecific antibody comprising a first recombinant variable region with a cell-penetrating determinant (e.g. Fv fragment) of anti-DNA monoclonal antibody 3E10 and a second recombinant variable region with an intracellular target-binding determinant for MDM2 (e.g. Fv fragment of mAb 3G5), thereby inhibiting the growth of tumor or cancer cells in the subject. In one embodiment, the tumor or cancer is a melanoma, colon adenocarcinoma, colorectal cancer, glioblastoma or astrocytoma.

The invention further provides a method for regulating activity of MDM2-interacting proteins with a bispecific antibody comprising contacting a cell with a bispecific antibody having a Fv fragment with a cell-penetrating determinant and a second Fv fragment with a binding determinant for MDM2.

In accordance with the invention, the MDM2-interacting proteins may comprise one or more of ABL1, APEX1, AR, ARF/P14, ARRB1, ARRB2, ATM, c-abl, CCNG1, CDKN2AIP, CK2, CTBP1, CTBP2, DAXX, DHFR, DNA pol. ε, DYRK2, E2F/DP1, E1A-associated protein EP300, FKBP3, ERBB4, FOXO4, GLN3, HDAC1, HIF-la, HIV-1 Tat, HTATIP, IGF1R, L5/RNA, L11, MDM4, MTBP, Numb, p16, p53/TP53, P63, p73/TP73, p300/CBP, PCAF, PI3K/AKT, PML, PSMA3PSMD10, PSME3, PYHIN1, RB, RB1, RBBP6, RBL5, RFWD3, RNA, RP11, RPL5, RPL11, RPL26, RRM2B, RYBP, Sp1, Sumo1, TAFII250, TBGR1, TBP/TFIIE, TRIM13, TRIM28, Tsg101, UBC, UBXN6, USP2, USP7, and human homologs.

In one embodiment, the bispecific antibody comprises bispecific single-chain Fv fragments derived from cell-penetrating monoclonal antibody, mAb 3E10, and anti-MDM2 monoclonal antibody, mAb 3G5.

In another embodiment, the bispecific antibody is a recombinant antibody, chimeric antibody, humanized antibody, or human antibody, or derivatives thereof.

The invention further provides a method for increasing therapeutic effectiveness of treating tumor, cancer or a dis-regulated intracellular process comprising the use of combination therapy with a bispecific antibody comprising: (a) a recombinant variable region with a cell-penetrating determinant (e.g. Fv fragment of mAb 3E10) and a second recombinant variable region with an intracellular target-binding determinant (e.g. Fv fragment of mAb 3G5), and (b) a second bispecific antibody comprising a recombinant variable region with a cell-penetrating determinant (e.g. Fv fragment of mAb 3E10) and an additional second recombinant variable region with an intracellular target-binding determinant (e.g. Fv fragment of mAb PAb421) for a second protein of the same biochemical pathway, intracellular signaling pathway, or regulatory network.

In one embodiment, the Fv fragment with a cell-penetrating determinant is derived from an antibody transported into a cell through a salvage pathway or derived from an anti-DNA antibody. The second Fv fragment with an intracellular target-binding determinant is derived from an anti-oncoprotein antibody. Further, the additional second Fv fragment is derived from a monoclonal antibody directed to the C-terminus of p53 tumor suppressor protein with ability to restore DNA-binding capability of the mutant p53 protein.

In one embodiment, the antibody transported into the cell through a salvage pathway or the antibody derived from an anti-DNA antibody is mAb 3E10. In another embodiment, the antibody derived from an anti-oncoprotein antibody is mAb 3G5.

In another embodiment, the monoclonal antibody directed to the C-terminus of p53 tumor suppressor protein is PAb421 (EMD Millipore catalog Number OP03).

In one embodiment, the bispecific antibody has amino acid sequence of SEQ ID NO:2. In another embodiment, the bispecific antibody is encoded by nucleic acid sequence, as shown in SEQ ID NO:1. In another embodiment, the bispecific antibody comprises one or more of amino acid sequence of SEQ ID NOS:3, 5, 7, 9, 11, 13, 15, 17, 19, 21, 23, 25, or 27. In yet another embodiment, the bispecific antibody is encoded by a nucleic acid sequence, comprising nucleic acid sequence as shown in SEQ ID NO:1 from nucleotide position 268 to 1833, or SEQ ID NOS:4, 6, 8, 10, 12, 14, 16, 18, 20, 22, 24, or 26.

In one embodiment, the bispecific antibody additionally comprises conservative amino acid substitution or substitutions.

In another embodiment, the nucleic acid sequence additionally comprises silent mutation or mutations.

In another embodiment, the bispecific antibody is encoded by a nucleic acid sequence, comprising a nucleic acid sequence of SEQ ID NO:1, SEQ ID NO:1 from nucleotide position 268 to 1833, or SEQ ID NOS: 4, 6, 8, 10, 12, 14, 16, 18, 20, 22, 24, or 26 with one or more conservative amino acid substitution(s) and/or silent mutation(s).

In one embodiment, the second bispecific antibody has amino acid sequence of SEQ ID NO:29. In another embodiment, the second bispecific antibody is encoded by nucleic acid sequence, as shown in SEQ ID NO:28. In another embodiment, the second bispecific antibody comprises one or more of amino acid sequence of SEQ ID NOS:30, 5, 7, 9, 11, 13, 15, 32, 34, 36, 38, 40, or 42. In yet another embodiment, the second bispecific antibody is encoded by a nucleic acid sequence, comprising nucleic acid sequence as shown in SEQ ID NO:28 from nucleotide position 268 to 1827, or SEQ ID NOS:4, 6, 8, 10, 12, 14, 31, 33, 35, 37, 39, or 41.

In one embodiment, the bispecific antibody additionally comprises conservative amino acid substitution or substitutions.

In one embodiment, the nucleic acid sequence additionally comprises silent mutation or mutations.

In one embodiment, the bispecific antibody is encoded by a nucleic acid sequence, comprising a nucleic acid sequence of SEQ ID NO:28, SEQ ID NO:28 from nucleotide position 268 to 1827, or SEQ ID NOS:4, 6, 8, 10, 12, 14, 31, 33, 35, 37, 39, or 41 with one or more conservative amino acid substitution(s) and/or silent mutation(s).

The invention also provides a method for producing a bispecific antibody comprising culturing the host vector system under suitable culture conditions so as to produce the bispecific antibody in the host and recovering the bispecific antibody so produced.

Compositions of the Invention

The invention provides a bispecific antibody comprising a first recombinant variable region of an immunoglobulin molecule with a cell-penetrating determinant (e.g., Fv fragment) from an anti-DNA monoclonal antibody 3E10 or a variable region of an immunoglobulin or polypeptide which competes with monoclonal antibody 3E10. The bispecific antibody further comprises a second recombinant variable region of an immunoglobulin molecule with an intracellular target-binding determinant (e.g., Fv fragment of mAb 3G5) that inhibits the biological activity, biochemical activity, regulatory activity or cellular signal associated with the determinant or a macromolecule to which the determinant is attached. The determinant or macromolecule may be human.

The bispecific antibody may be a chimeric antibody, a recombinant antibody, an anti-idiotypic antibody, a humanized antibody, or an affinity matured antibody. In other embodiments, the antibody fragment is a single domain antibody, a diabody, an scfv, an scfv dimer, a dsfv, a (dsfv)$_2$, a dsFv-dsfv', a bispecific ds diabody, a Fv, a Fab, a Fab', or a F(ab')$_2$. In other embodiments, the antibody fragment may be operably attached to a constant region, e.g. wherein the constant region may be a kappa light chain, gamma-1 heavy chain, gamma-2 heavy chain, gamma-3 heavy chain or gamma-4 heavy chain.

In further embodiments of the aspects of the invention, the isolated or bispecific antibody is a monoclonal antibody.

In one embodiment, the first antibody (e.g. Fv) fragment comprises one or more complementarity determining regions (CDRs) of mAb 3E10, as specified in SEQ ID NOS:5, 7, 9, 11, 13, and 15.

In another embodiment, the bispecific antibody comprises a CDR with at least 50% amino acid sequence identity or homology to SEQ ID NOS:5, 7, 9, 11, 13, or 15.

In another embodiment, the first antibody (e.g. Fv) fragment with a cell-penetrating determinant has monoclonal antibody 3E10 idiotype.

In yet another embodiment, the antibody that competes with the monoclonal antibody 3E10 is a chimeric, human or humanized antibody that competes with the uptake of monoclonal antibody 3E10 into the cell. In one embodiment, the uptake of monoclonal antibody 3E10 into the cell is through an equilibrative nucleoside transporter (ENTs) or a member of the SLC29 family of integral membrane proteins expressed by the cell. In another embodiment, the equilibrative nucleoside transporter (ENTs) or a member of the SLC29 family of integral membrane proteins is ENT2.

In one embodiment, the second antibody (e.g. Fv) fragment with an intracellular target-binding determinant is derived from an anti-idiotypic antibody directed against an idiotope, a set of idiotopes or an idiotype of an antibody directed against a human cytosolic, nuclear, mitochondrial, endoplasmic reticulum, membrane, and/or organelle macromolecule.

In one embodiment, the second antibody (e.g. Fv) fragment with an intracellular target-binding determinant is derived from an antibody directed against a cytosolic, nuclear, mitochondrial, endoplasmic reticulum, membrane, and/or organelle macromolecule.

In another embodiment, the macromolecule is a human protein, DNA, lipid, or RNA. The protein, lipid, DNA, or RNA macromolecule may be modified with a carbohydrate, phosphate group, carboxylic acid group, methyl group, sulfate group, lipid, hydroxyl group, amide group, amino acid, modified amino acid, selenium, ubiquitin, or SUMO protein, or contains a modified base or oxidized base, and combinations thereof.

In one embodiment, the macromolecule is a human protein associated with control of cell growth and proliferation, cell cycle, DNA repair, DNA integrity, transcription, replication, translation, or intracellular transport. In accordance with the invention, the protein may be Mdm2, BRCA1, MDC1, 53BP1, p53, ATM, ATR, CHK1, CHK2, WT1 (Dao, T. et al., Sci Transl Med, 2013, 5(176):176ra33) or p21.

In one embodiment, the Fv fragment with an intracellular target-binding determinant is derived from an anti-oncoprotein antibody. In another embodiment, the anti-oncoprotein antibody is directed to the Mdm2 oncoprotein. In a further embodiment, the anti-oncoprotein antibody directed to the Mdm2 oncoprotein is a mAb 3G5. In another embodiment, the monoclonal antibody is directed to the WT1 oncoprotein. In a further embodiment, the monoclonal antibody directed to the WT1 oncoprotein is a mAb ESK1.

In one embodiment, the anti-oncoprotein antibody is directed to a binding partner of a tumor suppressor protein. The binding partner of a tumor suppressor may be Mdm2 oncoprotein. Further, the tumor suppressor protein may be a p53 protein.

In one embodiment, the anti-oncoprotein antibody is directed to an E3 ubiquitin ligase.

In another embodiment, the anti-oncoprotein antibody disrupts the binding of an oncoprotein to a tumor suppressor protein.

The binding of an oncoprotein to a tumor suppressor protein may include the binding of Mdm2 to p53.

In another embodiment, the bispecific antibody further comprises a constant region. In one embodiment, the constant region is a kappa light chain, gamma-1 heavy chain, gamma-2 heavy chain, gamma-3 heavy chain or gamma-4 heavy chain.

In another embodiment, the bispecific antibody is produced as a recombinant protein in a bacterial cell, yeast cell, Chinese hamster ovary (CHO) cell, insect cell, or transgenic animals. The yeast cell may be Pichia pastoris, e.g., a X-33 cell. In one embodiment, the recombinant protein is secreted and post-translationally modified. In another embodiment, the post-translational modification comprises glycosylation, proteolytic processing of signal sequences, disulfide bridge formation, and/or lipid addition.

In one embodiment, the bispecific antibody comprises one or more amino acid sequence comprising Ala-Gly-Ile-His (AGIH) at the amino terminus of one or both of the recombinant variable region of the immunoglobulin molecule with a cell-penetrating determinant (e.g., a scFv fragment of mAb 3E10).

In one embodiment, the bispecific antibody has amino acid sequence of SEQ ID NO:2. In another embodiment, the bispecific antibody is encoded by nucleic acid sequence, as shown in SEQ ID NO:1. In another embodiment, the bispecific antibody comprises one or more of amino acid sequence of SEQ ID NOS:3, 5, 7, 9, 11, 13, 15, 17, 19, 21, 23, 25, or 27. In yet another embodiment, the bispecific antibody is encoded by a nucleic acid sequence, comprising nucleic acid sequence as shown in SEQ ID NO:1 from nucleotide position 268 to 1833, or SEQ ID NOS:4, 6, 8, 10, 12, 14, 16, 18, 20, 22, 24, or 26.

In one embodiment, the bispecific antibody additionally comprises conservative amino acid substitution or substitutions. In another embodiment, the nucleic acid sequence additionally comprises silent mutation or mutations. In yet another embodiment, the bispecific antibody is encoded by a nucleic acid sequence, comprising a nucleic acid sequence of SEQ ID NO:1, SEQ ID NO:1 from nucleotide position 268 to 1833, or SEQ ID NOS: 4, 6, 8, 10, 12, 14, 16, 18, 20, 22, 24, or 26 with one or more conservative amino acid substitution(s) and/or silent mutation(s).

In one embodiment, the bispecific antibody have the amino acid sequence of SEQ ID NO:29. In another embodiment, the bispecific antibody may be encoded by nucleic acid sequence, as shown in SEQ ID NO:28. In another embodiment, the bispecific antibody comprising one or more of amino acid sequence of SEQ ID NOS:30, 5, 7, 9, 11, 13, 15, 32, 34, 36, 38, 40, or 42. In yet another embodiment, the bispecific antibody encoded by a nucleic acid sequence, comprising nucleic acid sequence as shown in SEQ ID NO:28 from nucleotide position 268 to 1827, or SEQ ID NOS:4, 6, 8, 10, 12, 14, 31, 33, 35, 37, 39, or 41.

In one embodiment, the bispecific antibody additionally comprises conservative amino acid substitution or substitutions. In another embodiment, the nucleic acid sequence additionally comprises silent mutation or mutations. In another embodiment, the bispecific antibody is encoded by a nucleic acid sequence, comprising a nucleic acid sequence of SEQ ID NO:28, SEQ ID NO:28 from nucleotide position 268 to 1827, or SEQ ID NOS:4, 6, 8, 10, 12, 14, 31, 33, 35, 37, 39, or 41 with one or more conservative amino acid substitution(s) and/or silent mutation(s).

The invention further provides for a bispecific antibody or a single chain antibody comprising one or more of gly-gly-gly-gly-serine repeat(s), human CH1 linker, and a swivel sequence.

In one embodiment, the gly-gly-gly-gly-serine repeat(s) are three repeats of gly-gly-gly-gly-serine. In another embodiment, the human CH1 linker comprises the amino acid sequence as provided in SEQ ID NO:3 from amino acid position 253 to 265 or conservative amino acid substitution(s) within the sequence as provided in SEQ ID NO:3 from amino acid position 253 to 265. In one embodiment, the swivel sequence comprises the amino acid sequence as provided in SEQ ID NO:3 from amino acid position 266 to 271.

In one embodiment, the human CH1 linker is linked to the amino terminus of the swivel sequence by a peptide bond. In another embodiment, the human CH1 linker is covalently attached through its amino terminus to the carboxyl end of a Fv fragment.

In one embodiment, the nucleic acid molecule encodes the bispecific antibody of the invention. In another embodiment, the nucleic acid molecule is a DNA (e.g., cDNA) encoding the bispecific antibody of the invention.

The invention also provides for a vector which comprises the nucleic acid molecule of the invention. The host vector system comprises a vector of the invention in a suitable host cell. Examples of suitable host cells include but are not limited to bacterial cell and eukaryotic cell.

The invention also provides for a pharmaceutical composition for treating a subject suffering from tumor, cancer or a dis-regulated intracellular process comprising a bispecific antibody of the invention.

The invention further provides for a pharmaceutical composition for treating a subject suffering from tumor, cancer or a dis-regulated intracellular process comprising a bispecific antibody of the invention.

Examples of tumor or cancer include but are not limited to a melanoma, soft tissue tumors, sarcomas, Ewing's sarcoma, leiomyosarcomas, lipomas, liposarcomas, malignant fibrous histiocytomas, malignant Schwannomas, rhabdomyosarcomas, osteosarcomas, brain tumors, central nervous system gliomas, neuroblastoma, glioblastomas, astrocytomas, oligodendrogliomas, soft tissue sarcomas, osteosarcomas, breast cancer, cervical carcinomas, ovarian carcinomas, testicular tumors, urothelial carcinomas, esophageal carcinomas, lung cancers, non-small cell lung carcinoma (NSCLC), nasopharyngeal carcinomas, colorectal cancer, or colon cancer.

In another aspect, the invention contemplates a pharmaceutical composition comprising the bispecific antibodies of the invention in association with a pharmaceutically acceptable carrier. The pharmaceutical compositions preferably include suitable carriers and adjuvants which include any material which when combined with the molecule of the invention retains the molecule's activity and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g. oil/water emulsion), salts or electrolytes such as protamine sulfate, disodium hydrogen phosphate, potassium hydrogen phosphate, sodium chloride, zinc salts, colloidal silica, magnesium tri silicate, polyvinyl pyrrolidone, cellulose-based substances and polyethylene glycol. Other carriers may also include sterile solutions; tablets, including coated tablets and capsules. Typically such carriers contain excipients such as starch, milk, sugar (e.g. sucrose, glucose, maltose), certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods. Such compositions may also be formulated within various lipid compositions, such as, for example, liposomes as well as in various polymeric compositions, such as polymer microspheres.

In a further embodiment, the bispecific antibody is conjugated to the chemotherapeutic agent, a toxin, a radioisotope, or a detectable label.

In another embodiment, the invention provides an article of manufacture comprising a container and a composition of the invention contained therein.

In embodiments of the articles of manufacture of the invention, the article of manufacture comprises a bispecific antibody of the invention or antigen-binding fragment thereof operably attached to a chemotherapeutic agent, a toxin, a radioisotope.

In one embodiment, the compositions of the invention further comprises a therapeutic agent admixed with the bispecific antibody. The therapeutic agent may be an anti-cancer agent which may be lenalidomide, ipilimumab, rituximab, alemtuzumab, ofatumumab, flavopiridol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; amino glutethimide; amsacrine; anastrozole; anthramycin; asparaginase; asperlin; azacitidine; azetepa; azotomycin; batimastat; benzodepa; bicalutamide; bisantrene hydrochloride; bizelesin; bleomycin sulfate; brequinar sodium; bropirimine; busulfan; cactinomycin; calusterone; caracemide; carbetimer; carboplatin; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfmer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfm; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

In another embodiment, the compositions of the invention further comprising a therapeutic agent admixed with the bispecific antibody and the therapeutic agent may be an alkylating agent which includes but are not limited to nitrogen mustards (e.g., bendamustine, mechloroethamine, cyclophosphamide, chlorambucil, melphalan), ethylenimine and methylmelamines (e.g., hexamethlymelamine, thiotepa), alkyl sulfonates (e.g., busulfan), nitrosoureas (e.g., carmustine, lomustine, semustine, streptozocin), or triazenes (decarbazine).

Kits of the Invention

According to another aspect of the invention, kits are provided. Kits according to the invention include package(s) comprising composition of the invention.

The phrase "package" means any vessel containing compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes (including pre-filled syringes), bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of components of the composition herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in therapies as described herein. In certain embodiments, the package(s) is a container for intravenous administration.

The following examples are presented to illustrate the present invention and to assist one of ordinary skill in making and using the same. The examples are not intended in any way to otherwise limit the scope of the invention.

EXAMPLES

Example 1

Materials and Methods

Cell Lines

Cell lines obtained from the American Type Culture Collection (ATCC) include: COS-7 monkey kidney cells; MC-7 human ovarian cancer cells that over-express MDM2; 3T3 transformed mouse fibroblasts; BJ primary human fibroblasts. Human melanoma cells sensitive to MDM2 inhibition were obtained from Maria S. Soengas, Madrid, Spain, and included SK-MEL-103, SK-MEL-147, UACC-62, and UACC-257. These cell lines were not authenticated by our laboratory after receiving them.

Design, Expression, and Purification of the 3E10-3G5 Bispecific Antibody

3G5 hybridoma was obtained from Arnold J. Levine, Princeton University. 3G5 Vk and VH were cloned by RT-PCR from hybridoma RNA with degenerate primers designed to identify mouse immunoglobulin variable region genes, and 3G5 scFv was constructed as described previously (4). Variable region heavy and light chains were attached with a $(GGGGS)_3$ linker. The Fv fragments were connected with a linker composed of CH1 sequences combined with a swivel sequence (6). 3E10-3G5 bispecific scFv cDNA was constructed in pPicZαA (Invitrogen, Carlsbad, Calif.; Catalog No. V195-20) between the EcoRI and XbaI cloning sites in frame with the C-terminal myc-his6 tag. Plasmids were transfected into X-33 cells, and a high-secreting clone was identified as described previously (6). Bispecific antibody was purified from X-33 supernatant by metal chelation chromatography on Ni-NTA-Agarose. The bispecific antibody was shown to be stable at 4° C. for 3 months.

Cell Penetration Assay

COS-7 cells were incubated with control media, media containing 10 μM 3E10 scFv, or media containing 10 μM 3E10-3G5 for one hour. Media was then removed from the cells, and cells were washed, fixed, and stained with an anti-myc antibody as described previously (3).

In Vitro Assays of 3E10-3G5 Cytotoxicity

Cells were grown in DMEM with 10% FCS. Adherent cells were removed with EDTA and distributed in 96-well plates overnight in the presence of medium alone, 3E10, or 3E10-3G5. Growth was evaluated after 3 days by counting cells. Results were expressed as percent total cell number (relative to control)±S.D.

In Vivo Assays of 3E10-3G5 Cytotoxicity

Animal studies were done under a protocol approved by the Veterans Affairs Institutional Animal Care and Use Committee. Nude mice (nu/nu) were obtained from The Jackson Laboratory, Bar Harbor, Me. Six Nude mice were injected subcutaneously with $1 \times 10^6$ UACC-257 cells and observed (control). Six Nude mice were injected subcutaneously with $1 \times 10^6$ UACC-257 cells on day 1 and treated with intraperitoneal injections of 1.0 mg 3E10-3G5 scFv on days 1 through 4. Tumor volume (mm³) was measured in mice that developed tumors, and animals were euthanized when tumors exceeded 2000 mm³ or at the termination of the experiment on day 22.

Western Blot Assays

UACC-257 tumors were excised, and tumor tissue was lysed in 2% SDS. Protein (20 µg) from each tumor was electrophoresed in a 4-20% polyacrylamide gradient gel and then transblotted to a nylon membrane. Western blots were probed with antibodies to p53, MDM2, and actin.

Statistical Analyses

Significant differences in tumor growth were determined by Students t test.

Results

3E10-3G5 Retains the MDM2-Binding Activity of 3G5 and the Cell-Penetrating Activity of 3E10

A 3E10-3G5 bispecific antibody composed of the single chain variable fragments of the cell-penetrating 3E10 antibody and the anti-MDM2 3G5 antibody was produced as a secreted protein by *Pichia pastoris* X-33 cells transfected with pPicZαA containing the bispecific scFv cDNA (FIG. 1A). 3E10-3G5 was purified from yeast supernatant by metal chelation chromatography on Ni-NTA-Agarose as described previously (6) (FIG. 1B). Purified 3E10-3G5 was used as a probe for MDM2 in a Western blot assay on lysates from MC-7 cells over-expressing MDM2, and was found to recognize and bind MDM2 similar to the full 3G5 antibody and with similar binding specificity (FIG. 1C). MC-7 cells were selected as a convenient source of MDM2. Next, 3E10-3G5 was applied to COS-7 cells in culture and was observed to penetrate into the cells and localize in nuclei similar to 3E10 scFv alone (FIG. 1D). COS-7 cells over-express hENT-2 and served as a convenient model cell to demonstrate cellular penetration by the bispecific scFv. These results demonstrate that the 3E10-3G5 bispecific antibody retains the cell-penetrating activity of 3E10 scFv and the MDM2-binding activity of 3G5 scFv.

3E10-3G5 Impairs the Growth of MDM2-Addicted Melanoma Cells

We next investigated the impact of 3E10-3G5 on melanoma cells known to be sensitive to MDM2 inhibition (10). UACC-257 melanoma cells were incubated for 3 days with media containing concentrations of 3E10-3G5 ranging from 0-10 µM. 3E10 and 3G5 alone were used as controls and had no observable effect on the growth or morphology of UACC-257 melanoma cells compared to culture medium (FIG. 2C). However, 3E10-3G5 delayed the growth of the cells in a dose-responsive manner, with significant growth delay observed at a dose of 10 µM (FIG. 2A). A similar effect was observed in additional MDM2-addicted melanoma cell lines, with marked inhibition of growth and distinct morphological changes observed in all of the melanoma cell lines tested (FIGS. 2B and 2C). As expected, 3E10 and 3G5 alone had no apparent effect on any of the melanoma cell lines (FIG. 2). Importantly, 3E10-3G5 had only a mild impact on the growth of murine 3T3 transformed fibroblasts and had no effect on the growth of BJ primary human fibroblasts (FIG. 2B). Taken together these data suggest that 3E10-3G5 successfully inhibited MDM2 in vitro and caused a growth delay specifically in the MDM2-addicted cells.

3E10-3G5 Inhibits Growth of Melanoma Tumors In Vivo

The activity of 3E10-3G5 in vivo was tested in a human melanoma xenograft model. Nude mice were injected subcutaneously with $1 \times 10^6$ UACC-257 cells, and mice were observed or treated for 4 consecutive days with intraperitoneal injections of 1.0 mg 3E10-3G5 beginning at day 1. Four mice in the control group and five mice in the experimental group developed tumors. Mice that developed tumors were then followed closely and tumor volumes were measured. Importantly, treatment with 3E10-3G5 was not associated with any clinical toxicity, as treated mice were indistinguishable from control mice with respect to their appearance and activity. However, treatment with 3E10-3G5 significantly inhibited tumor growth at day 20 (p=0.041) and at the termination of the experiment on day 22 (p=0.026) (FIG. 3A-3C). In order to probe the mechanism responsible for tumor growth inhibition, we evaluated the relative levels of p53 and MDM2 in representative tumors from three untreated mice and three mice treated with 3E10-3G5. Treatment with 3E10-3G5 increased the expression of MDM2 and p53 as shown in Western blots of tumor lysates probed with antibodies to p53 and MDM2 (FIG. 3D). Actin served as a loading control. These results are similar to changes in MDM2 and p53 levels observed in cells and tumors treated with small molecule inhibitors of MDM2 (10) and further suggest that 3E10-3G5 successfully inhibited MDM2 in vivo.

Discussion

We have demonstrated that treatment with a 3E10-3G5 bispecific antibody impairs the growth of melanoma cells in vitro and in vivo. This growth delay is likely the result of increased levels of activated p53 that have been freed from inhibition by MDM2 by the action of the 3G5 antibody fragment. In keeping with this hypothesis, elevated levels of p53 were observed in tumors in mice treated with the bispecific antibody. We also noted that these tumors exhibited increased levels of MDM2, which is consistent with results obtained by others with MDM2 inhibitors such as Nutlin-3, and is likely the result of increased levels of p53 driving additional production of MDM2 (10). Since MDM2 has numerous p53-independent effects (10) it is possible that the impact of 3E10-3G5 on the melanoma cells and tumors is the result of an effect on diverse metabolic pathways in addition to its impact on p53 function. Although we administered micromolar amounts of 3E10-3G5 to mice, only nanomolar amounts are internalized intracellularly consistent with antigen-binding specific effects.

We previously constructed and demonstrated efficacy of a cell-penetrating bispecific antibody composed of 3E10 scFv and the scFv fragment of mAb PAb421, an antibody that binds and restores the function of some p53 mutants (6). In the present study we have extended our cell-penetrating bispecific antibody technology by demonstrating the effectiveness of this approach in modulating MDM2 activity in vivo. Since p53 activity can be inhibited by mutation and/or over-expression of MDM2, combination therapy with 3E10-3G5 and 3E10-PAb421 may prove particularly useful in select tumor cells.

Our studies establish proof-of-principle for the use of the cell-penetrating antibody 3E10 as a transport vehicle to deliver therapeutic antibody fragments directed to intracellular and intranuclear targets. The exquisite antigen-binding specificity of antibodies delivered into intracellular compartments will likely result in improved therapeutic indices by avoiding off-target binding responsible for toxic side effects of small molecule inhibitors. In addition, cell-penetrating bispecific antibodies can be designed that bind intracellular epitopes such as transcription factors and DNA repair proteins that cannot presently be targeted with small molecule inhibitors and are currently considered undruggable. The use of cell-penetrating bispecific antibodies in targeted molecular therapy will significantly broaden the spectrum of accessible intracellular targets and may have a profound impact in cancer therapy.

Example 2

3E10-PAb421 Inhibits Growth of HT29 Cells in vitro and in vivo

Figure 6A:
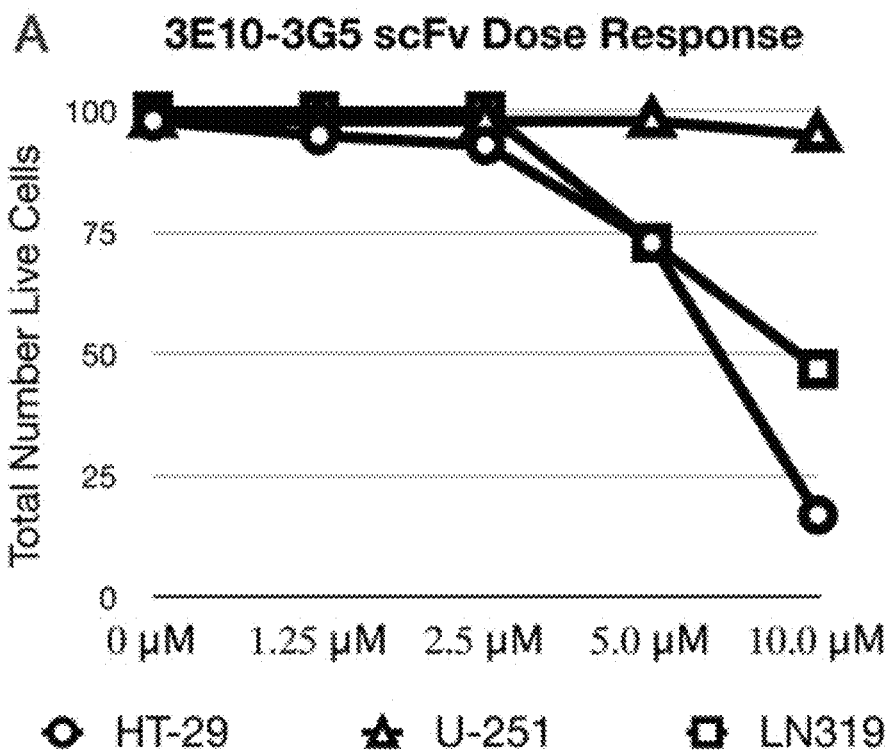
FIGS. 6A-B show line graphs of (FIG. 6A) 3E10-3G5 scFv dose response and (FIG. 6B) 3E10-Pab421 scFv dose response on growth of a human colon cancer cell line (HT29), a human glioblastoma cell line (U251) and a human astrocytoma cell line (LN-319) in vitro.
Figure 6B:
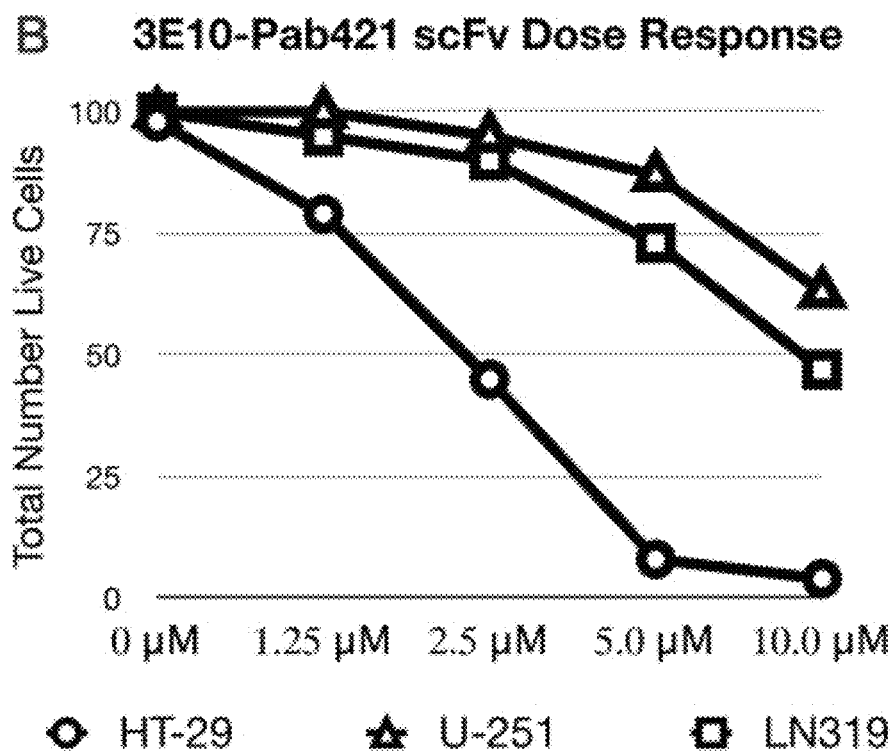
Figures 8A, 8B:
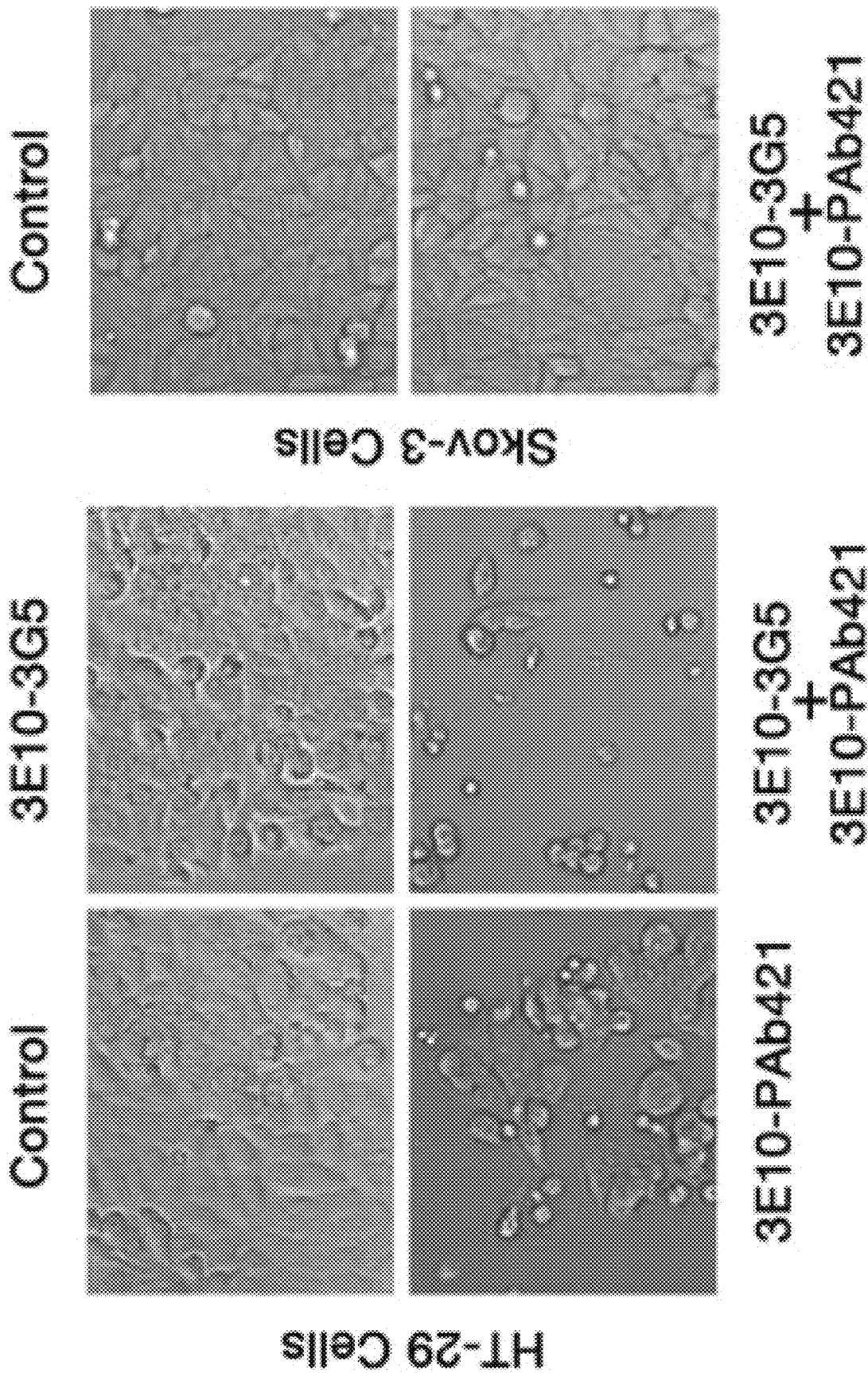
FIGS. 8A-B show photomicrographs of a synergistic cytotoxic effect of 3E10-3G5 and 3E10-PAb421 bispecific antibody treatment on HT-29 cells in vitro. Unlike HT-29 (FIG. 8A), a human ovarian cell line, Skov-3 (FIG. 8B), does not appear to be affected morphologically by the combined treatment; Skov-3 does not express p53 protein.
Figure 9A:
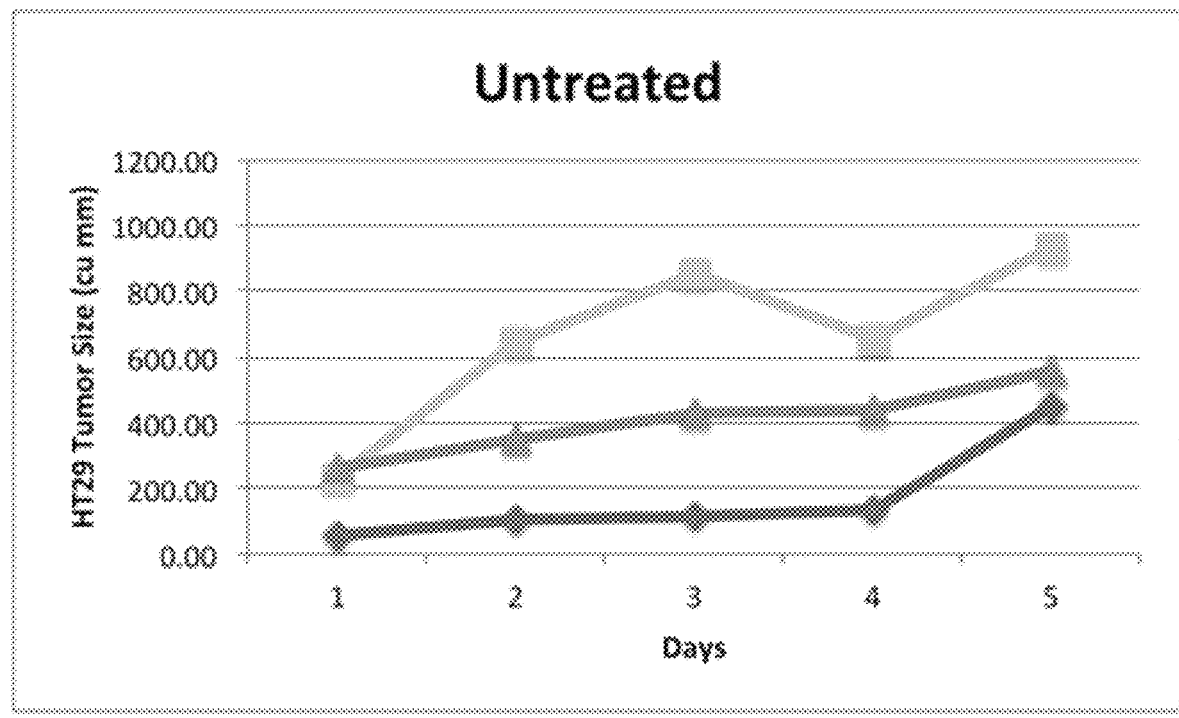
FIGS. 9A-B show line graphs of untreated HT-29 tumor (FIG. 9A) and HT-29 tumor treated with 3E10-PAb421 (FIG. 9B) in vivo in a nude mouse xenograft model.
Figure 9B:
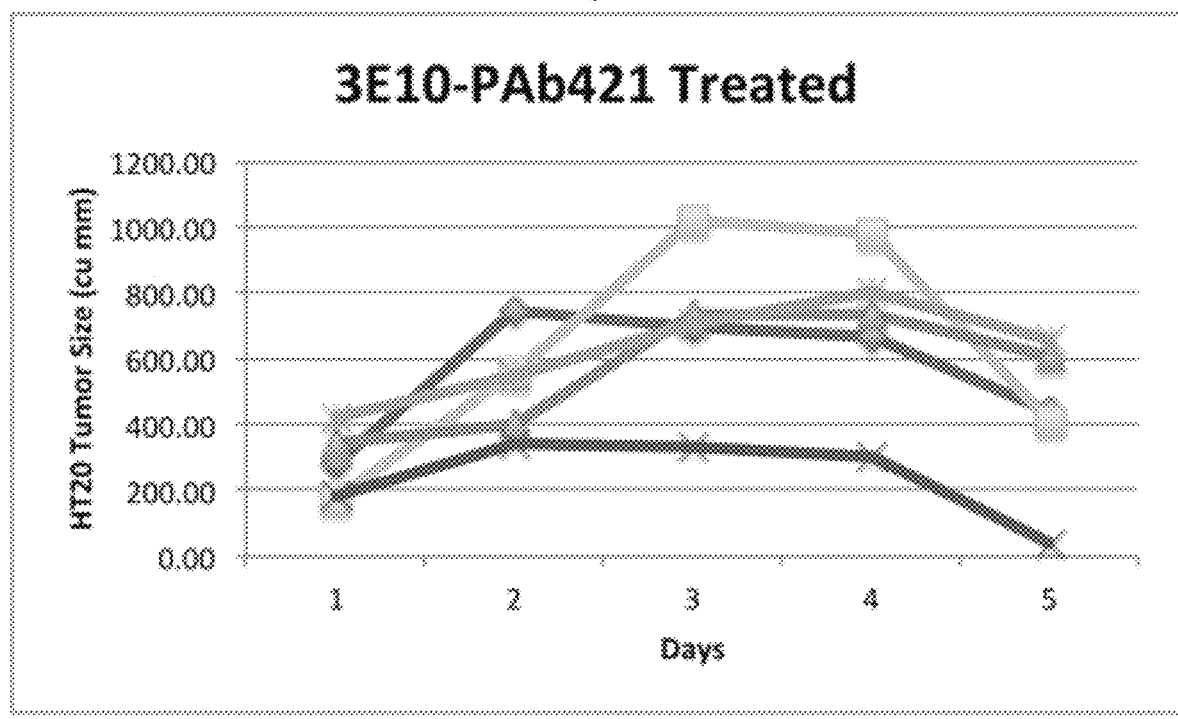

3E10-PAb421 bispecific single-chain antibody was assayed in vitro for cytotoxicity against the colon cancer cell line, HT29 and glioblastoma cell line, U251 both containing p53 mutation R273H. Also tested was the astrocytoma cell line, LN319 containing p53 mutation R175H. All of the cell lines showed dose-response inhibition of growth in response to 3E10-PAb421 (FIG. 6). Moreover, 3E10-PAb421 and 3E10-3G5 were synergistic in inhibiting the growth of cancer cells (FIG. 7). Cytotoxicity in vitro is shown in a photomicrograph (FIG. 8). Nude mice were used to study the effect of 3E10-PAb421 on the growth of HT29 cancer cells in vivo. Mice were injected with $2\times10^6$ HT29 cells in the hind flank. When tumors reached 400 mm$^3$, 1.5 mg of 3E10-PAb421 was injected intraperitoneally daily. 3E10-PAb421 inhibited growth of tumors 2 to 3 days following initiation of therapy (FIG. 9).

REFERENCES

1. Zhang J, Yang P L, Gray N S. Targeting cancer with small molecule kinase inhibitors. Nature Reviews Cancer 2009; 9:28-39.
2. Zack D J, Stempniak M, Wong A L, Taylor C, Weisbart R H. Mechanisms of cellular penetration and nuclear localization of an anti-double strand DNA autoantibody. J Immunol 1996; 157:2082-8.
3. Hansen J E, Tse C M, Chan G, Heinze E R, Nishimura R N, Weisbart R H. Intranuclear protein transduction through a nucleoside salvage pathway. J Biol Chem 2007; 282:20790-3.
4. Weisbart R H, Stempniak, M, Harris, S, Zack, D J, Ferreri K. An autoantibody is modified for use as a delivery system to target the cell nucleus: Therapeutic implications. J Autoimmun 1998; 11:539-46.
5. Weisbart R H, Baldwin R, Huh B, Zack D J, Nishimura R. Novel protein transfection of primary rat cortical neurons utilizing an antibody that penetrates living cells. J Immunol 2000; 164:6020-6.
6. Weisbart R H, Wakelin R, Chan G, Miller C W, Koeffler P H. Construction and expression of a bispecific single-chain antibody that penetrates mutant p53 colon cancer cells and binds p53. Int J Onc 2004; 25:1113-8.
7. Hansen J E, Fischer L K, Chan G, Chang S S, Baldwin S W, Aragon R J et al. Antibody-mediated p53 protein therapy prevents liver metastasis in vivo. Cancer Res 2007; 67:1769-74.
8. Heinze E, Baldwin S, Chan G, Hansen J, Song J, Clements D et al. Antibody-mediated FOXP3 protein therapy induces apoptosis in cancer cells in vitro and inhibits metastasis in vivo. Int J Oncol 2009; 35:167-73.
9. Zhan X, Ander B P, Liao I H, Hansen J E, Kim C, Clements D et al. Recombinant Fv-Hsp70 protein mediates neuroprotection after focal cerebral ischemia in rats. Stroke 2010; 3:538-43.
10. Verhaegen M, Checinska A, Riblett M B, Wang S, Soengas M S. E2F1-dependent oncogenic addiction of melanoma cells to MDM2. Oncogene 2012; 7:828-41.
11. Chen J, Marechal V, Levine A J. Mapping of the p53 and mdm-2 Interaction Domains. Mol. & Cell Biol 1993; 13:4107-14.
12. Bottger A, Bottger V, Garcia-Echeverria C, Chene P, Hochkeppel H K, Sampson W et al. Molecular characterization of the hdm2-p53 interaction. 1997; 269:744-56.
13. Rayburn E, Zhang R, He J, Wang H. MDM2 and Human Malignancies: Expression, Clinical Pathology, Prognostic Markers, and Implications for Chemotherapy. Current Cancer Drug Targets 2005; 5:27-41.
14. Shangary S, Wang S. Small-molecule inhibitors of the MDM2-p53 protein-protein interaction to reactivate p53 function: a novel approach for cancer therapy. Annu Rev Pharmacol Toxicol 2009; 49:223-41.
15. Lane D P, Brown C J, Verma C, Cheok C F. New insights into p53 based therapy. Discovery Med 2011; 63:107-17.

What is claimed is:

1. A bispecific antibody comprising a first Fv fragment, wherein the first Fv fragment comprises a heavy chain variable domain comprising: a) a complementarity determining region (CDR) CDRH1 comprising SEQ ID NO: 11, b) a CDRH2 comprising SEQ ID NO: 13 and c) a CDRH3 comprising SEQ ID NO: 15; and, a light chain variable domain comprising: a) a CDRL1 comprising SEQ ID NO: 5, b) a CDRL2 comprising SEQ ID NO: 7, and c) a CDRL3 comprising SEQ ID NO: 9; and a second Fv fragment, wherein the second Fv fragment comprises a heavy chain variable domain comprising: a) a CDRH1 comprising SEQ ID NO: 23, b) CDRH2 comprising SEQ ID NO: 25 and c) CDRH3 comprising SEQ ID NO: 27; and, a light chain variable domain comprising: a) CDRL1 comprising SEQ ID NO: 17, b) CDRL2 comprising SEQ ID NO: 19, and c) CDRL3 comprising SEQ ID NO: 21.

2. The bispecific antibody of claim 1, wherein the bispecific antibody has the amino acid sequence of SEQ ID NO: 3.

* * * * *